US008076312B2

(12) United States Patent
Yedgar

(10) Patent No.: US 8,076,312 B2
(45) Date of Patent: *Dec. 13, 2011

(54) USE OF LIPID CONJUGATES IN THE TREATMENT OF DISEASE

(75) Inventor: Saul Yedgar, Jerusalem (IL)

(73) Assignee: Yissum Research Development Company of the Hebrew University of Jerusalem Ltd, Jerusalem (IL)

( * ) Notice: Subject to any disclaimer, the term of this patent is extended or adjusted under 35 U.S.C. 154(b) by 561 days.

This patent is subject to a terminal disclaimer.

(21) Appl. No.: 11/285,375

(22) Filed: Nov. 23, 2005

(65) Prior Publication Data

US 2006/0293276 A1  Dec. 28, 2006

Related U.S. Application Data

(63) Continuation-in-part of application No. 10/989,606, filed on Nov. 17, 2004, now Pat. No. 7,811,999, and a continuation-in-part of application No. 10/989,607, filed on Nov. 17, 2004, now Pat. No. 7,772,196, which is a continuation-in-part of application No. 10/627,981, filed on Jul. 28, 2003, now Pat. No. 7,101,859, which is a continuation-in-part of application No. 09/756,765, filed on Jan. 10, 2001, now Pat. No. 7,034,006, which is a continuation-in-part of application No. PCT/IL2005/001225, filed on Nov. 17, 2005.

(60) Provisional application No. 60/174,907, filed on Jan. 10, 2000.

(51) Int. Cl.
A61K 31/728 (2006.01)
A61K 31/717 (2006.01)
A61K 31/685 (2006.01)

(52) U.S. Cl. .................. 514/54; 514/56; 514/57; 514/78
(58) Field of Classification Search .................... 514/54, 514/56, 57, 78
See application file for complete search history.

(56) References Cited

U.S. PATENT DOCUMENTS

| 4,604,376 | A |   | 8/1986  | Teng |
| 4,624,919 | A |   | 11/1986 | Kokusho |
| 4,654,327 | A |   | 3/1987  | Teng |
| 5,064,817 | A |   | 11/1991 | Yedgar et al. |
| 5,169,636 | A |   | 12/1992 | Nanba et al. |
| 5,354,853 | A |   | 10/1994 | Staveski |
| 5,401,511 | A |   | 3/1995  | Margalit |
| 5,401,777 | A |   | 3/1995  | Ammon et al. |
| 5,464,942 | A |   | 11/1995 | Sakurai et al. |
| 5,470,578 | A |   | 11/1995 | Aoki et al. |
| 5,512,671 | A |   | 4/1996  | Piantadose |
| 5,587,363 | A |   | 12/1996 | Henderson |
| 5,733,892 | A |   | 3/1998  | Sakurai |
| 5,785,975 | A |   | 7/1998  | Parikh |
| 6,022,866 | A |   | 2/2000  | Falk et al. |
| 6,043,231 | A |   | 3/2000  | Pruzanski et al. |
| 6,071,532 | A | * | 6/2000  | Chaikof et al. ............... 424/450 |
| 6,162,787 | A |   | 12/2000 | Sorgente et al. |
| 6,171,614 | B1|   | 1/2001  | Chaikof et al. |
| 6,180,596 | B1|   | 1/2001  | Tsao |
| 6,325,385 | B1| * | 12/2001 | Iwashita et al. ............... 277/442 |
| 7,101,859 | B2|   | 5/2004  | Yedgar et al. |
| 6,749,813 | B1| * | 6/2004  | David et al. .................... 422/102 |
| 7,141,552 | B2|   | 11/2006 | Yedgar et al. |

FOREIGN PATENT DOCUMENTS

| EP | 0236951    | 9/1987  |
| EP | 0529659    | 3/1993  |
| EP | 0581281    | 2/1994  |
| EP | 0581282 B  | 2/1994  |
| EP | 1046394 A  | 10/2000 |
| JP | 04082893   | 3/1992  |
| JP | 09030970   | 2/1997  |
| JP | 09030979   | 2/1997  |
| JP | 2002345455 | 12/2002 |
| JP | 2003160498 | 3/2003  |
| JP | 2003335801 | 11/2003 |
| JP | 2004018841 | 1/2004  |
| JP | 2004170194 | 6/2004  |
| WO | WO 87/02777| 5/1987  |
| WO | WO 87 02777| 5/1987  |
| WO | WO 91/00289| 1/1991  |
| WO | WO 96/04001| 2/1996  |
| WO | WO 96/11670| 4/1996  |

(Continued)

OTHER PUBLICATIONS

Albini, A, Iwamoto, Y, Kleinman, HK, Martin, GR, Aaronson, SA, Kozlowski, JM and McEwan, RN (1987) "A rapid in vitro assay for quantitating the invasive potential of tumor cells" Cancer Res 47(12):3239-45.

Balsinde, J, Balboa, MA, Yedgar, S and Dennis, EA (2000) "Group V phospholipase A(2)-mediated oleic acid mobilization in lipopolysaccharide-stimulated P388D(1) macrophages" J Biol Chem 275(7):4783-6.

Beck, G, Yard, BA, Schulte, J, Oberacker, R, Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" Br J Pharmacol 135(7):1665-74.

Brenner, T, Arnon, R, Sela, M, Abramsky, O, Meiner, Z, Riven-Kreitman, R, Tarcik, N and Teitelbaum, D (2001) "Humoral and cellular immune responses to Copolymer 1 in multiple sclerosis patients treated with Copaxone" J Neuroimmunol 115(1-2):152-60.

(Continued)

Primary Examiner — Kamal Saeed
(74) Attorney, Agent, or Firm — Pearl Cohen Zedek Latzer, LLP

(57) ABSTRACT

This invention provides a method of preventing asthma, allergic rhinitis, or chronic obstructive pulmonary disease in a subject comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof. This invention also provides a method of treating allergic rhinitis or chronic obstructive pulmonary disease in a subject comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof.

54 Claims, 22 Drawing Sheets

FOREIGN PATENT DOCUMENTS

| | | |
|---|---|---|
| WO | WO 9628544 | 9/1996 |
| WO | WO9628544 | 9/1996 |
| WO | WO9701330 | 1/1997 |
| WO | WO 9701330 | 1/1997 |
| WO | WO 97/48337 | 12/1997 |
| WO | WO9816198 | 4/1998 |
| WO | WO 9816198 | 4/1998 |
| WO | WO 98/51285 | 11/1998 |
| WO | WO 01/51003 | 7/2001 |
| WO | WO 01/91805 | 12/2001 |
| WO | WO 2005/084307 | 9/2005 |

OTHER PUBLICATIONS

Brenner, T, Lisak, RP, Rostami, A, Pleasure, DE and Silberberg, DH (1986) "Astrocytes, oligodendrocytes, and Schwann cells share a common antigenic determinant that cross-reacts with myelin basic protein: identification with monoclonal antibody" *J Neurosci* 6(7):1925-33.

Brenner, T, Poradosu, E, Soffer, D, Sicsic, C, Gazit, A and Levitzki, A (1998) "Suppression of experimental autoimmune encephalomyelitis by tyrphostin AG-556" *Exp Neurol* 154(2):489-98.

Cabanas, C and Hogg, N (1993) "Ligand intercellular adhesion molecule 1 has a necessary role in activation of integrin lymphocyte function-associated molecule 1" *Proc Natl Acad Sci U S A* 90(12):5838-42.

Chen, WM, Soria, J, Soria, C, Krimsky, M and Yedgar, S (2002) "Control of capillary formation by membrane-anchored extracellular inhibitor of phospholipase A(2)" *FEBS Lett* 522(1-3):113-8.

Dan, P, Dagan, A, Krimsky, M, Pruzanski, W, Vadas, P. and Yedgar, S (1998) "Inhibition of type I and type II phospholipase A2 by phosphatidyl-ethanolamine linked to polymeric carriers" *Biochemistry* 37(17):6199-204.

Darville, T, Yedgar, S, Krimsky, M, Andrews, CW, Jr., Jungas, T and Ojcius, DM (2004) "Protection against *Chlamydia trachomatis* infection in vitro and modulation of inflammatory response in vivo by membrane-bound glycosaminoglycans" *Microbes Infect* 6(4):369-76.

Davidson, FF, Dennis, EA, Powell, M and Glenney, JR, Jr. (1987) "Inhibition of phospholipase A2 by "lipocortins" and calpactins. An effect of binding to substrate phospholipids" *J Biol Chem* 262(4):1698-705.

Greaves MW and Camp RD (1988) "Prostaglandins, leukotrienes, phospholipase, platelet activating factor, and cytokines: an integrated approach to inflammation of human skin." *Arch Dermatol Res* 280:S33-41.

Krimsky, M, Dagan, A, Aptekar, L, Ligumsky, M and Yedgar, S (2000) "Assessment of intestinal permeability in rats by permeation of inulin-fluorescein" *J Basic Clin Physiol Pharmacol* 11(2):143-53.

Krimsky, M, Yedgar, S, Aptekar, L, Schwob, O, Goshen, G, Gruzman, A, Sasson, S and Ligumsky, M (2003) "Amelioration of TNBS-induced colon inflammation in rats by phospholipase A2 inhibitor" *Am J Physiol Gastrointest Liver Physiol* 285(3):G586-92.

Margolis-Nunno, H, Ben-Hur, E, Gottlieb, P, Robinson, R, Oetjen, J and Horowitz, B (1996) "Inactivation by phthalocyanine photosensitization of multiple forms of human immunodeficiency virus in red cell concentrates" *Transfusion* 36(8):743-50.

Murthy, SN, Cooper, HS, Shim, H, Shah, RS, Ibrahim, SA and Sedergran, DJ (1993) "Treatment of dextran sulfate sodium-induced murine colitis by intracolonic cyclosporin" *Dig Dis Sci* 38(9):1722-34.

Okayasu, I, Hatakeyama, S, Yamada, M, Ohkusa, T, Inagaki, Y and Nakaya, R (1990) "A novel method in the induction of reliable experimental acute and chronic ulcerative colitis in mice" *Gastroenterology* 98(3):694-702.

Schmiel, DH and Miller, VL (1999) "Bacterial phospholipases and pathogenesis" *Microbes Infect* 1(13):1103-12.

Schnitzer, E, Dagan, A, Krimsky, M, Lichtenberg, D, Pinchuk, I, Shinar, H and Yedgar, S (2000) "Interaction of hyaluronic acid-linked phosphatidylethanolamine (HyPE) with LDL and its effect on the susceptibility of LDL lipids to oxidation" *Chem Phys Lipids* 104(2):149-60.

Schnitzer, E, Yedgar, S, Danino, D, Talmon, Y and Lichtenberg, D (1999) "The Interaction of hyaluronic-phosphatidylethanolamine with low density lipoprotein (LDL) and its effect on copper induced LDL oxidation" *Biophysical Journal* 76(1): Part 2.

Schnitzer, E, Pinchuk, I, Fainaru, M, Lichtenberg, D and Yedgar, S (1998) "LDL-associated phospholipase A does not protect LDL against lipid peroxidation in vitro" *Free Radic Biol Med* 24(7-8):1294-303.

Yard, BA, Yedgar, S, Scheele, M, Van Der Woude, D, Beck, G, Heidrich, B, Krimsky, M, Van Der Woude, FJ and Post, S (2002) "Modulation of IFN-gamma-induced immunogenicity by phosphatidylethanolamine-linked hyaluronic acid" *Transplantation* 73(6):984-92.

Yedgar, S, Lichtenberg, D and Schnitzer, E (2000) "Inhibition of phospholipase A(2) as a therapeutic target" *Biochim Biophys Acta* 1488(1-2):182-7.

Soeda et al (Biochemistry 29:5188-5144) Tissue Plasminogen Activator Catalyzed Lys-Plasminogen Activation on Heparin-Inserted Phospholipid Liposomes.

Parish et al (Int. J. Cancer 40: 511-518, "Evidence that sulphated polysaccharides inhibit tumour metastasis by blocking tumour-cell-derived heparanases."

Wang D.P, Matthias Schuster, Yi Fong Wang, Chi Huey Wong "Synthesis of phospholipid-inhibitor conjugates by enzymic transphosphatidylation with phospholipase", J. Am. Chem. Soc.; 1993; 115(23); 10487-10491.

Carey et al, "Contrasting effects of cycloxygenase-1 (cox-1) and cox-2 deficiency in the host response to influenze, a viral infection". Journ. of Immunology 2005, vol. 15: 175 (10): 6878-84.

Soeda, et al "Tissue Plasminogen Activator Catalyzod Lys-Plasminogen Activation on Heparin-Inserted Pholsholid Liposomes." *Biochemistry* 29: 5188-5194.

Cummings, B.S., "Phospholipase $A_2$ as targets for anti-cancer drugs," Biochemical Pharmacology 74 (2007), pp. 949-959.

Kokotos, G. et al., "Novel 2-Oxoamide Inhibitors of Human Group IVA Phospholipase $A_2$," J. Med. Chem., 2002, 45, pp. 2891-2893.

Teitelbaum D, Arnon R, Sela M, Rabinsohn Y, Shapiro D., "Sphingomyelin specific antibodies elicited by synthetic conjugates," Immunochemistry. Nov. 1973;10(11):735-43.

Weltzien Hu, Matthiessen HP, Meyer-Delius M, Zimmermann F, Rüde E., "Acidic "peptidophospholipids", a new class of hapten-bearing cell surface modifying reagents," Mol Immunol. Sep. 1984;21(9):801-10.

Winger TM, Ludovice PJ, Chaikof EL, "Lipopeptide conjugates: biomolecular building blocks for receptor activating membrane-mimetic structures," Biomaterials. Feb. 1996;17(4):437-41.

Office Action of U.S. Appl. No. 11/220,965 dated Mar. 27, 2008.

Office Action of U.S. Appl. No. 11/598,812 dated Dec. 19, 2008.

Office Action of U.S. Appl. No. 10/989,606 dated Sep. 1, 2009.

Supplementary Search Report of European Application No. 05724186.1 dated Nov. 17, 2009.

Ofice Action of Japanese Application No. 2001-551427 dated Nov. 20, 2009.

\* cited by examiner

Fig. 1.1:
Inhibition of endothelin-1 (ET)-induced contraction of rat tracheal rings by Lipid-conjugates.
A: Contraction of rat trachea by Endothelin-1.
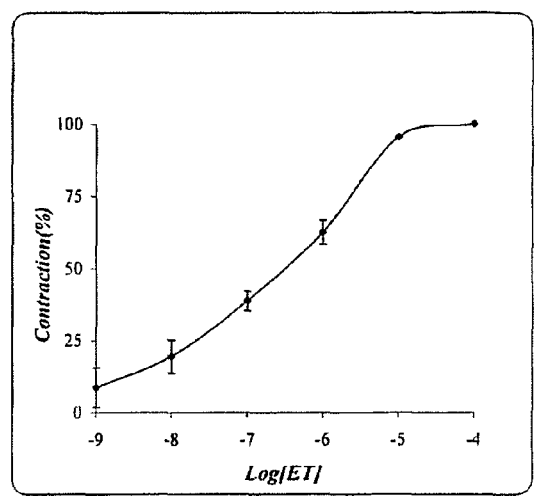
B: Effect of HYPE on ET- induced contraction of rat trachea.
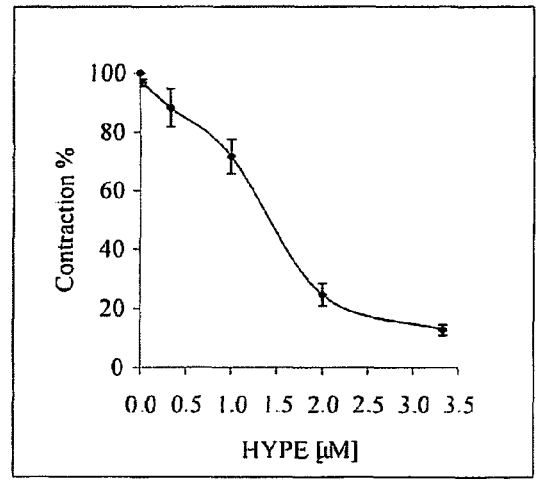

Fig. 1.2:
Effect of HYPE and Hyaluronic acid (HA) on ET-1- induced contraction of rat trachea.
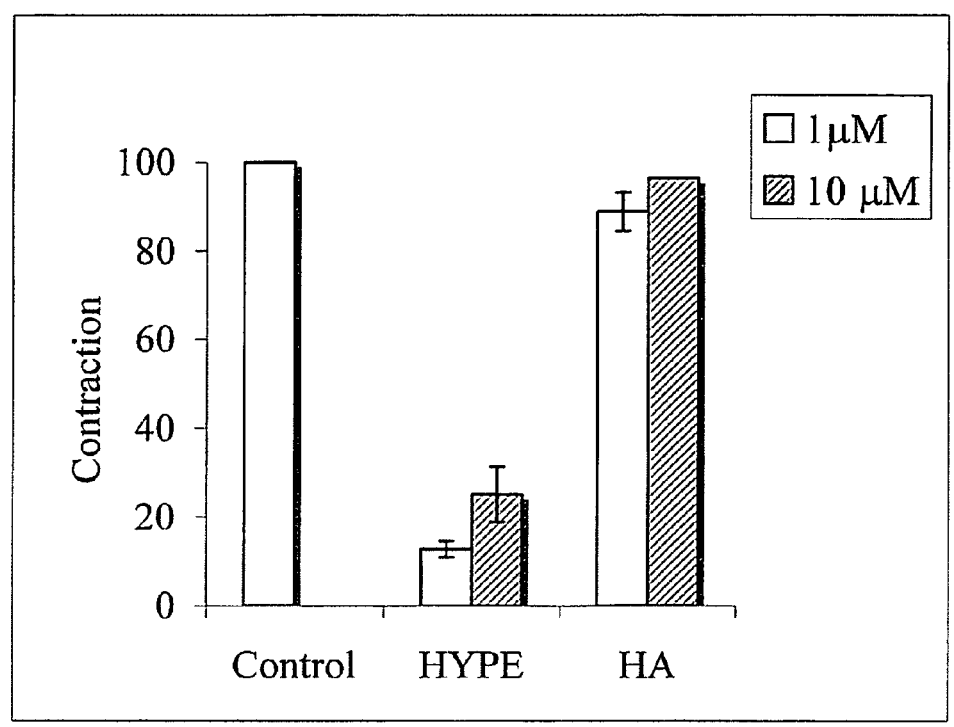

Fig 1.3:
Effect of HYPE and Hyaluronic acid (HA) on Acetylcholine (AcCh) – induced contraction of isolated rat trachea rings.
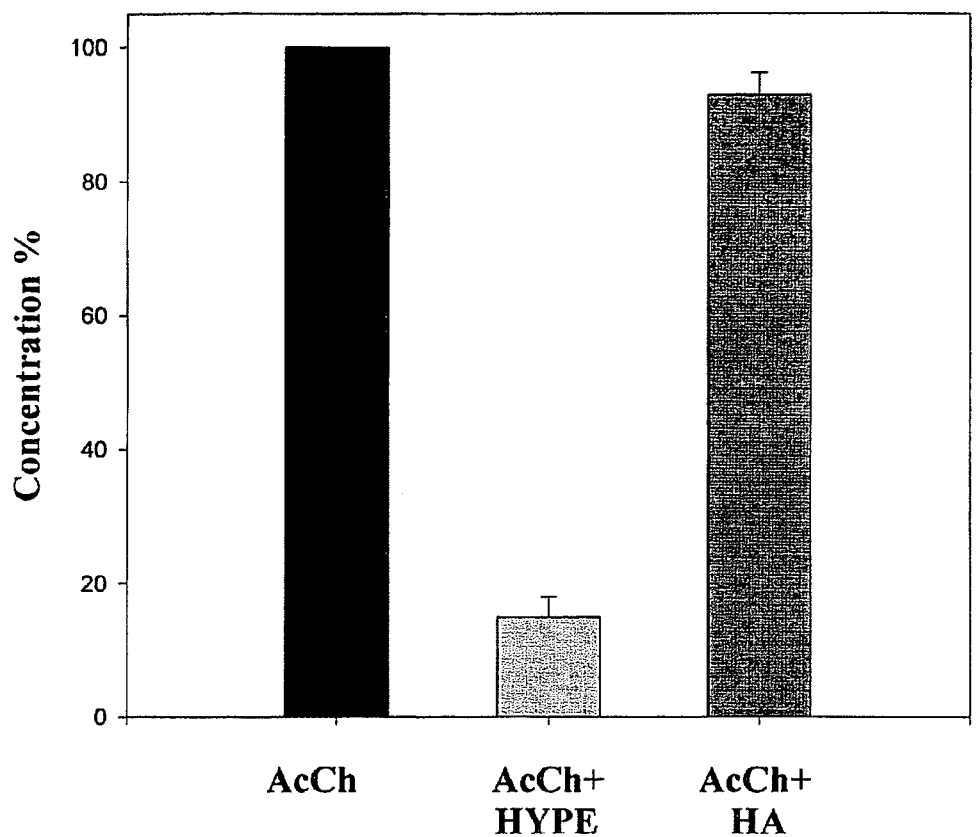

Fig. 1.4:
Effect of HyPE, administered subcutaneously, on early asthmatic reaction (EAR) induced by ovalbumin inhalation
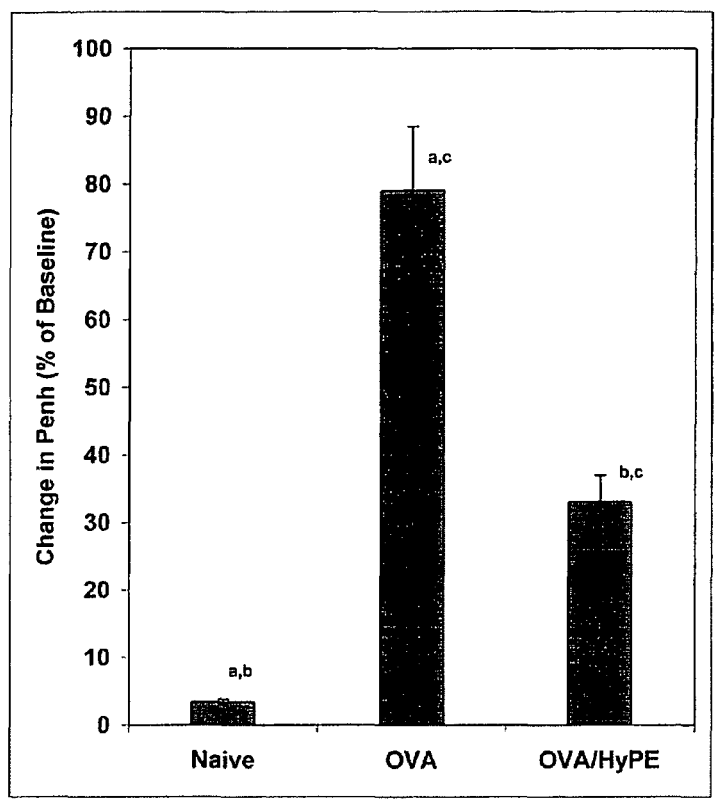

Fig. 1.5:
Effect of HyPE on sPLA$_2$ expression in lung of rats with OVA-induced asthma
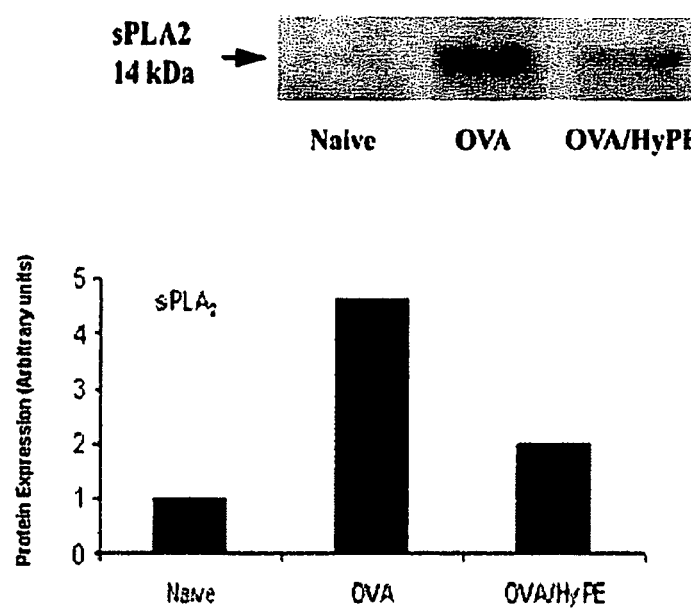

Fig. 1.6:
Effect of HyPE on cysteinyl leukotriens (LTC$_4$, LTD$_4$ and LTE$_4$) level in the BAL of OVA-induced asthmatic rats
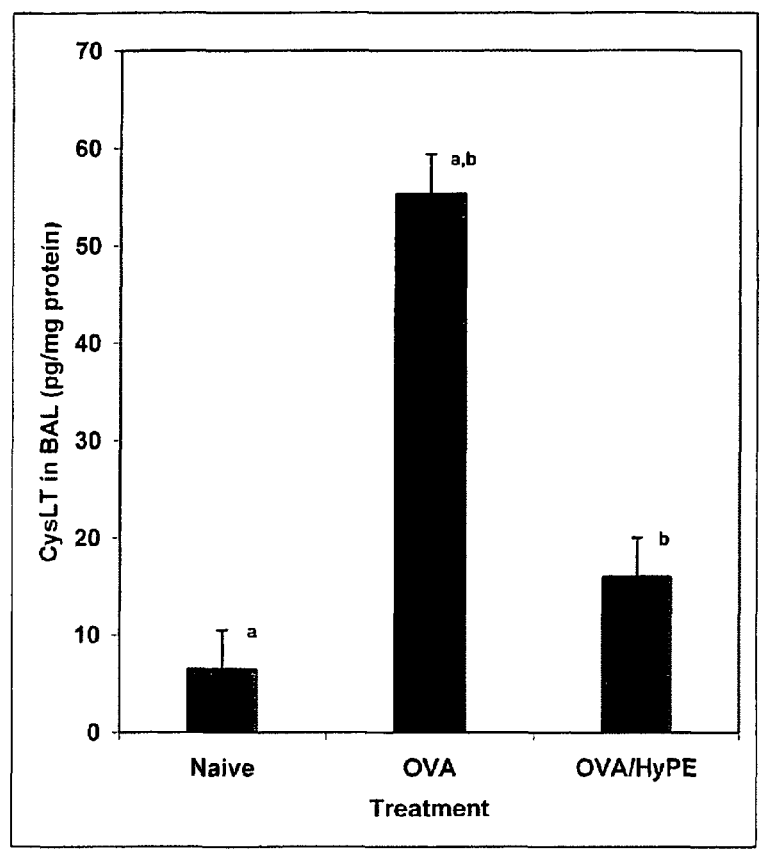

Fig. 1.7:
Effect of HyPE inhalation on early and late asthmatic reaction (EAR and LAR, respectively) in OVA-sensitized asthmatic rats.
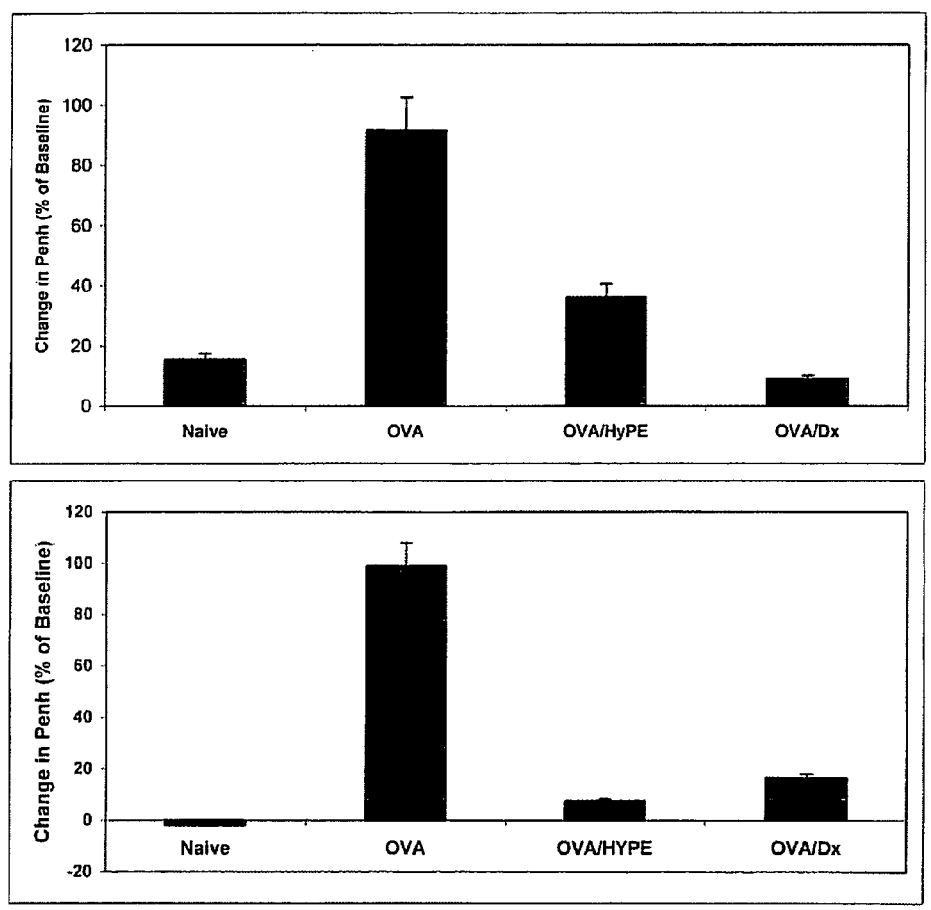

Fig. 1.8:
Effect of HyPE inhalation on cysteinyl leukotriens (LTC4, LTD4 and LTE4) level in the BAL of OVA-sensitized asthmatic rats
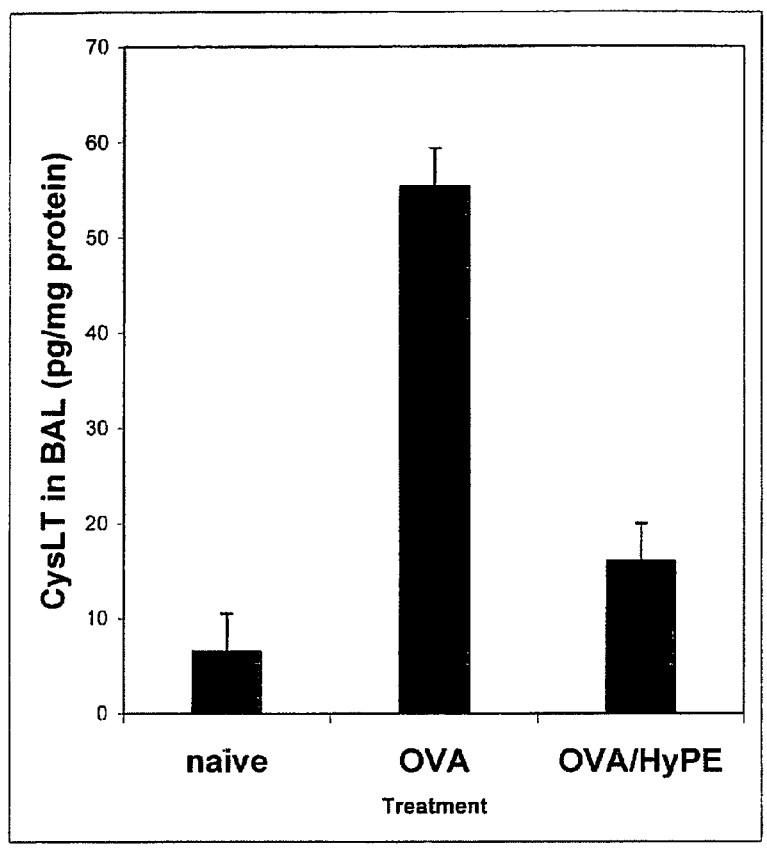

Fig 1.9:
Effect of HyPE inhalation on NO production by macrophages collected from the BAL of OVA-sensitized asthmatic rats.
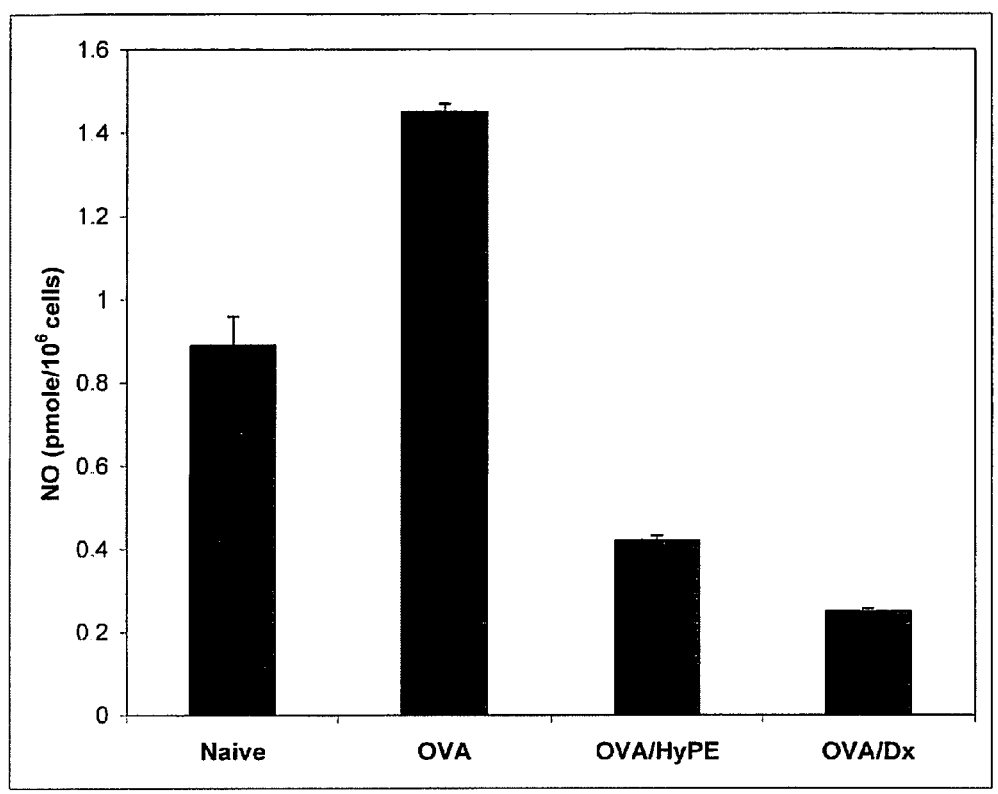

Fig. 1.10:
Effect of HyPE inhalation on structural change in airways (airway remodeling) of OVA sensitized asthmatic rats.
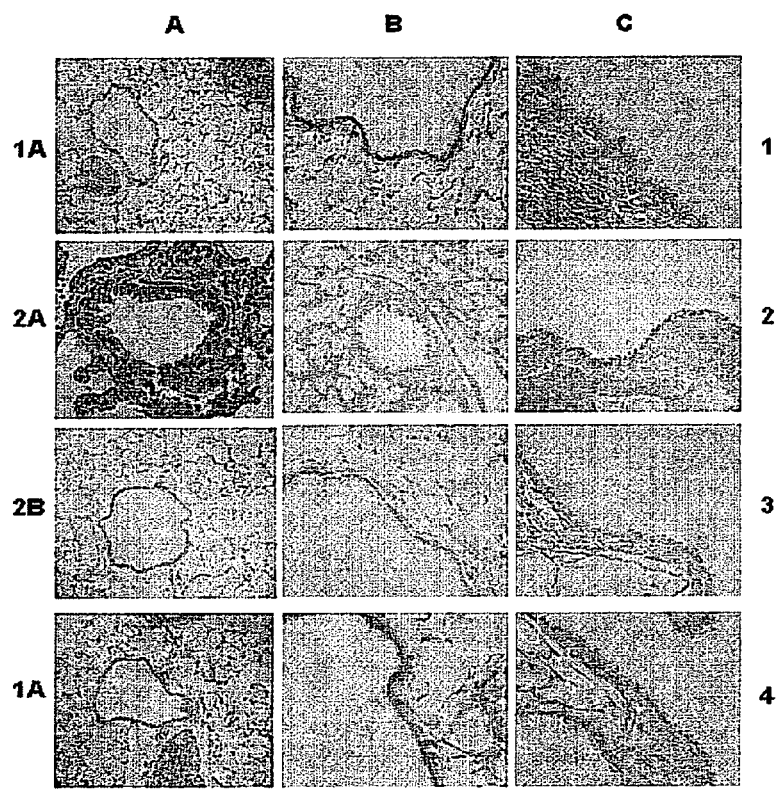

Fig. 1.11:
Effect of HyPE on remodeling of asthmatic rat airway; histological morphometry:
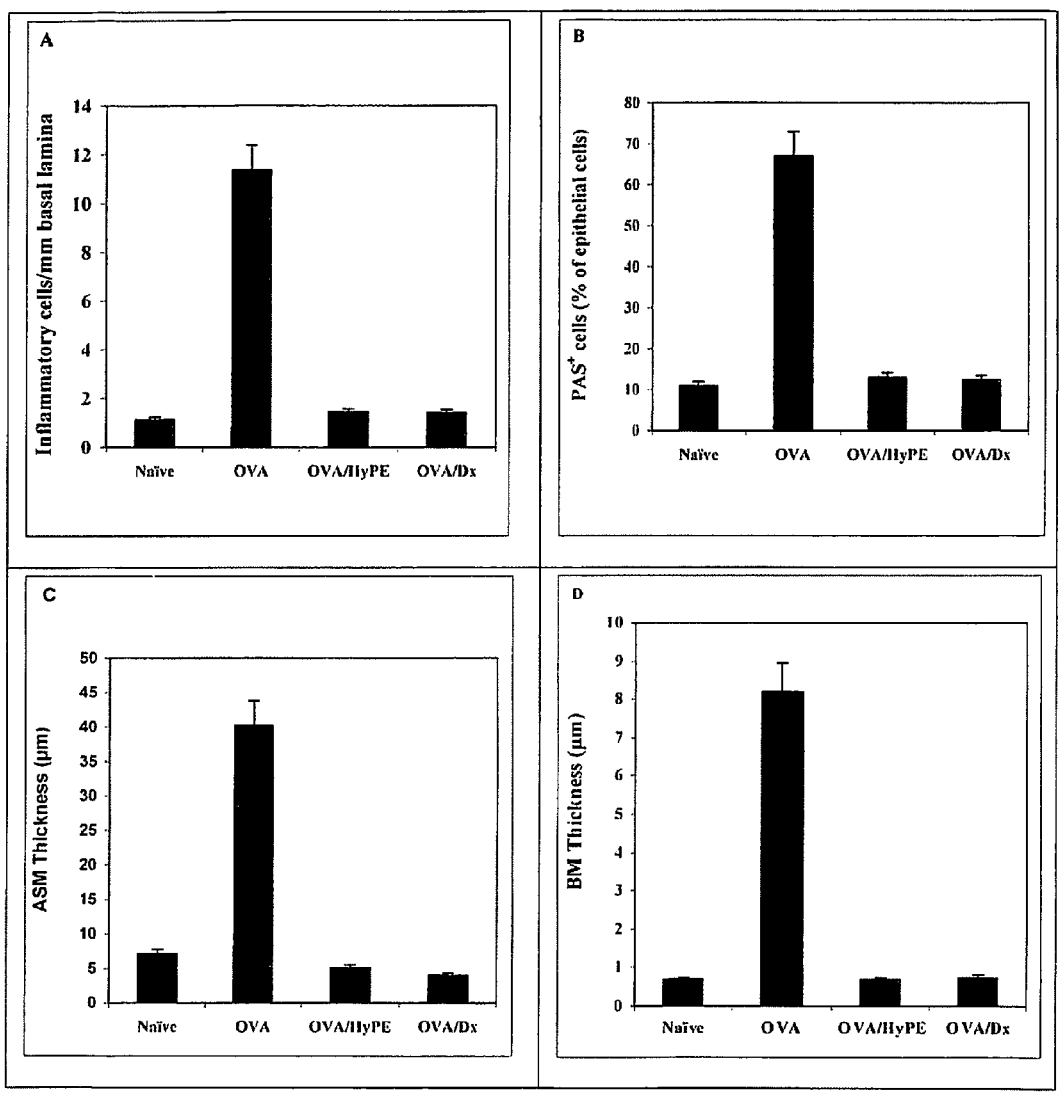

Fig. 1.12:
Effect of HyPE inhalation on TNFα production by macrophages collected from the BAL of OVA-sensitized asthmatic rats (see Methods for details)
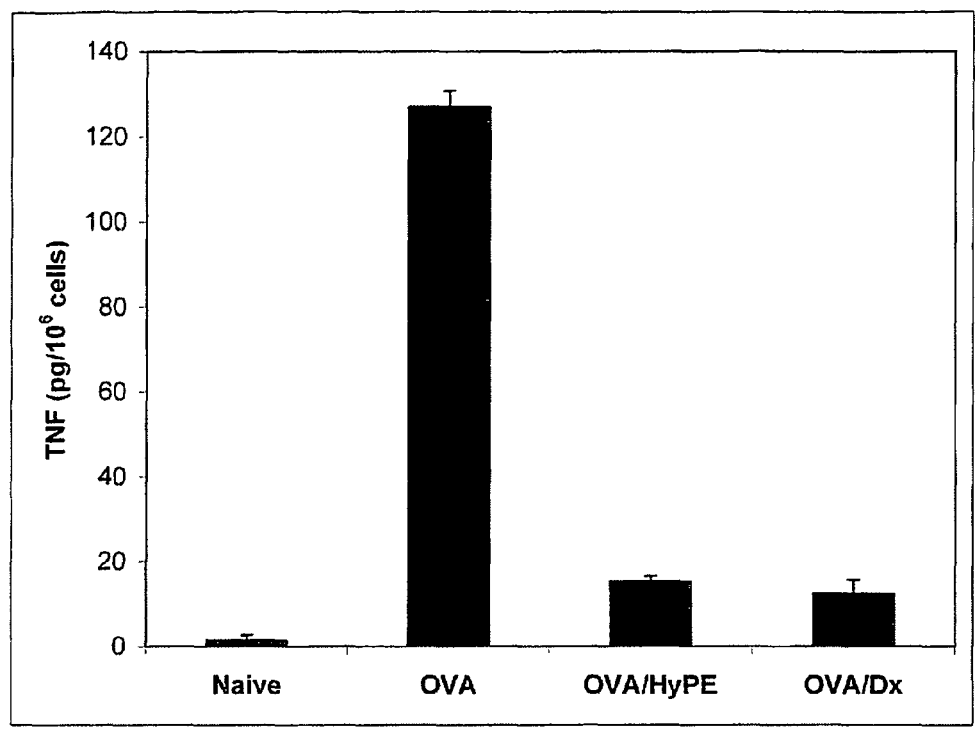

Fig. 1.13:
Amelioration of OVA-induced broncho-constriction by HyPE inhalation before challenge.
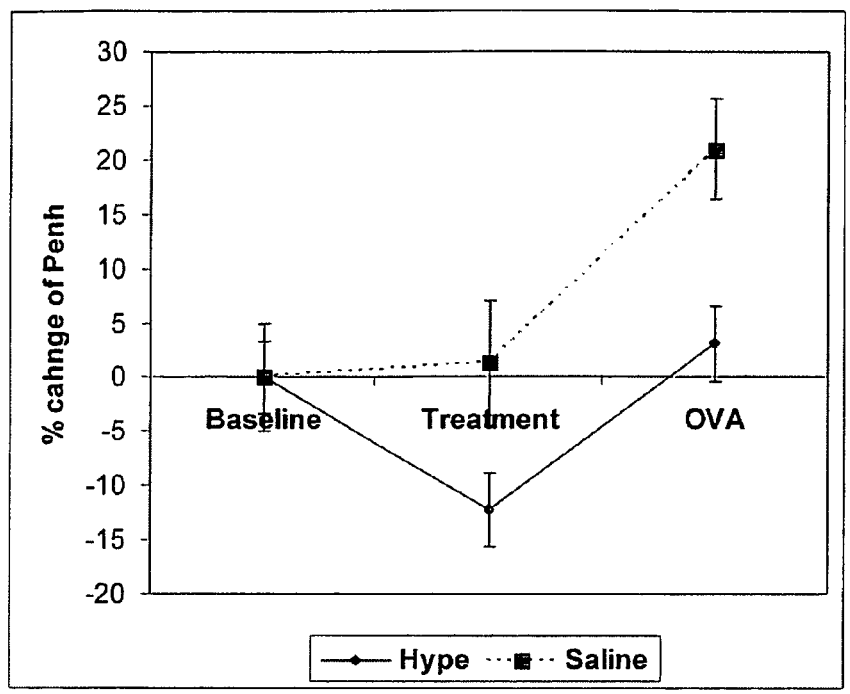

Fig. 1.14:
Amelioration of OVA-induced broncho-constriction by HyPE inhalation after challenge.
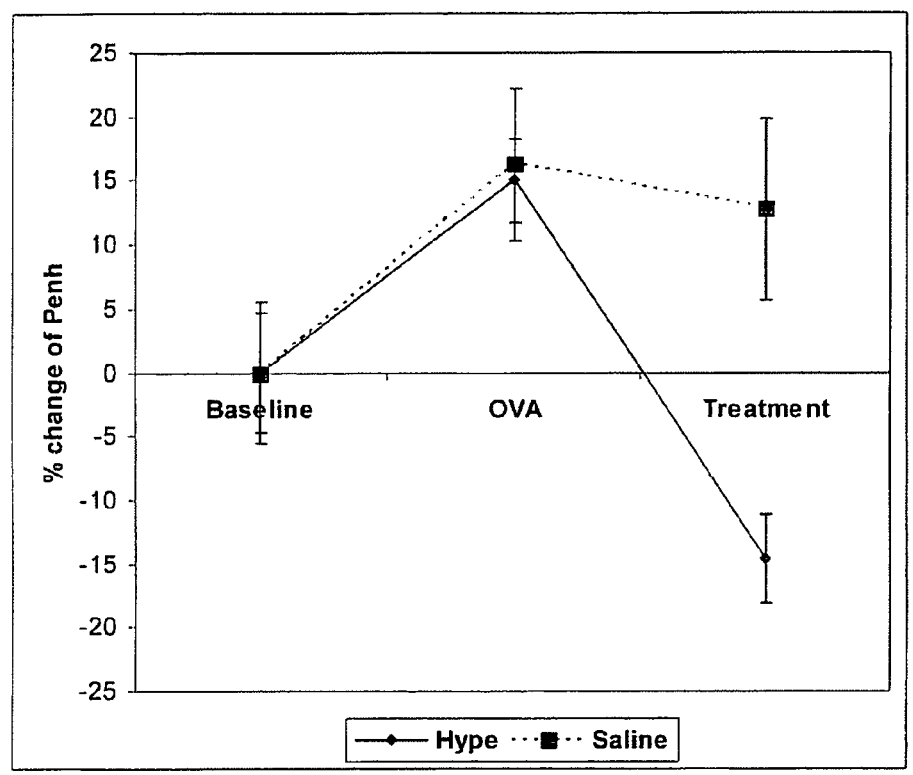

Fig. 2.1: CMPE protects BGM cells from membrane lysis induced by combined action of hydrogen peroxide (produced by glucose oxidase = GO), and exogenous phospholipase A2 (PLA2)
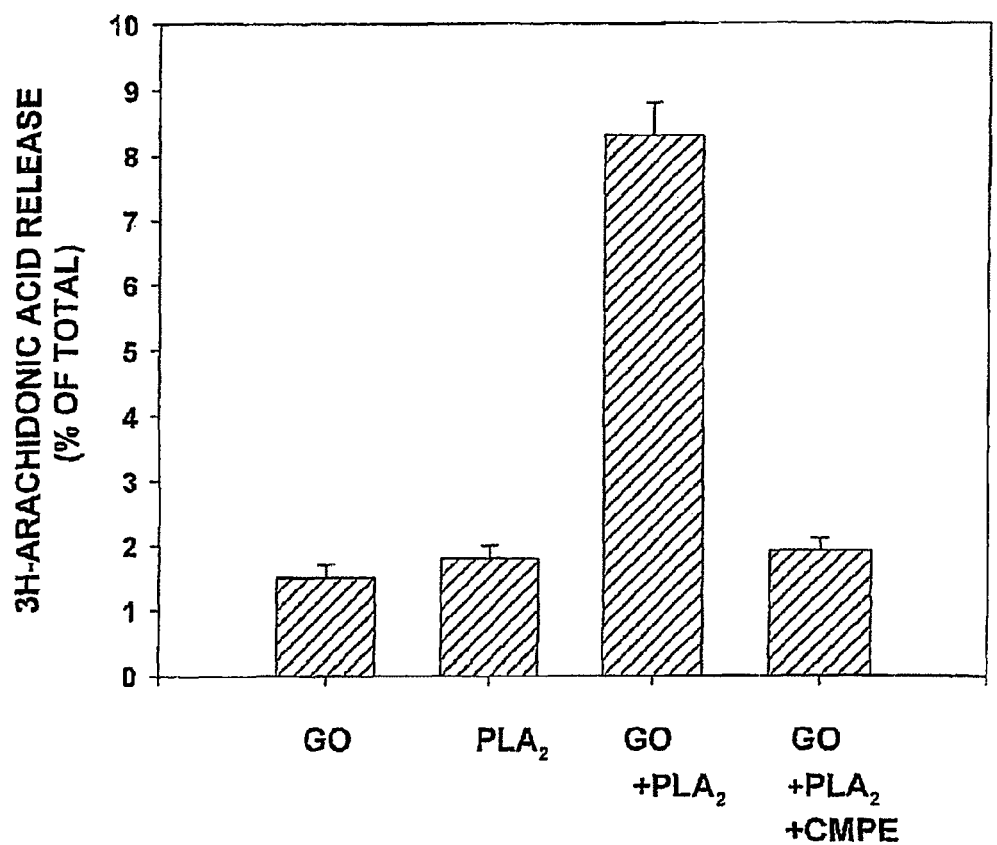

Fig. 2.2: CMPE protects BGM cells from glycosaminoglycan degradation by hydrogen peroxide (produced by glucose oxidase = GO)
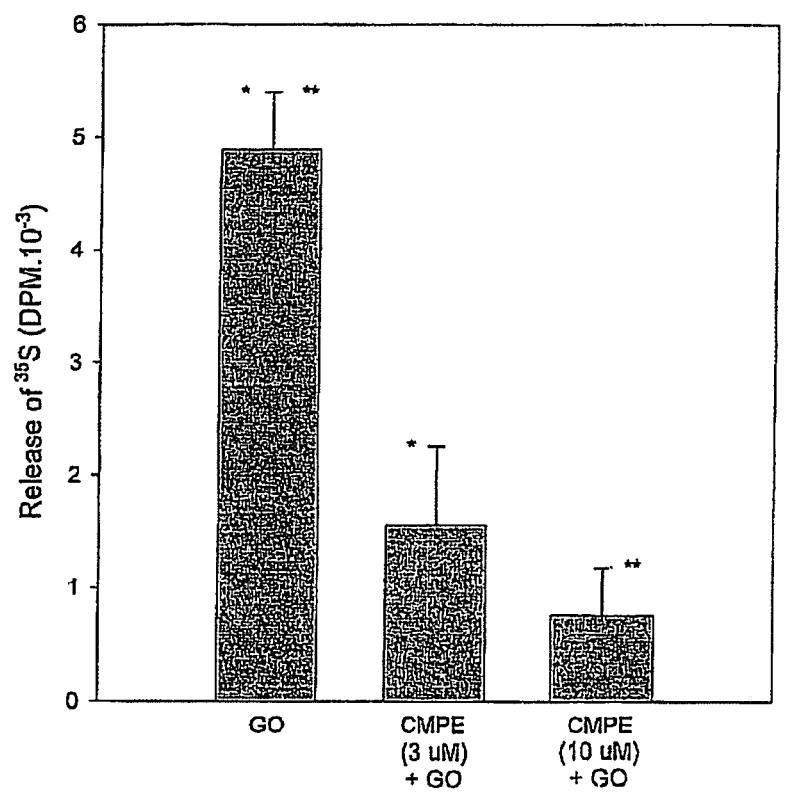

Fig. 2.3: HYPE protects LDL from copper-induced oxidation
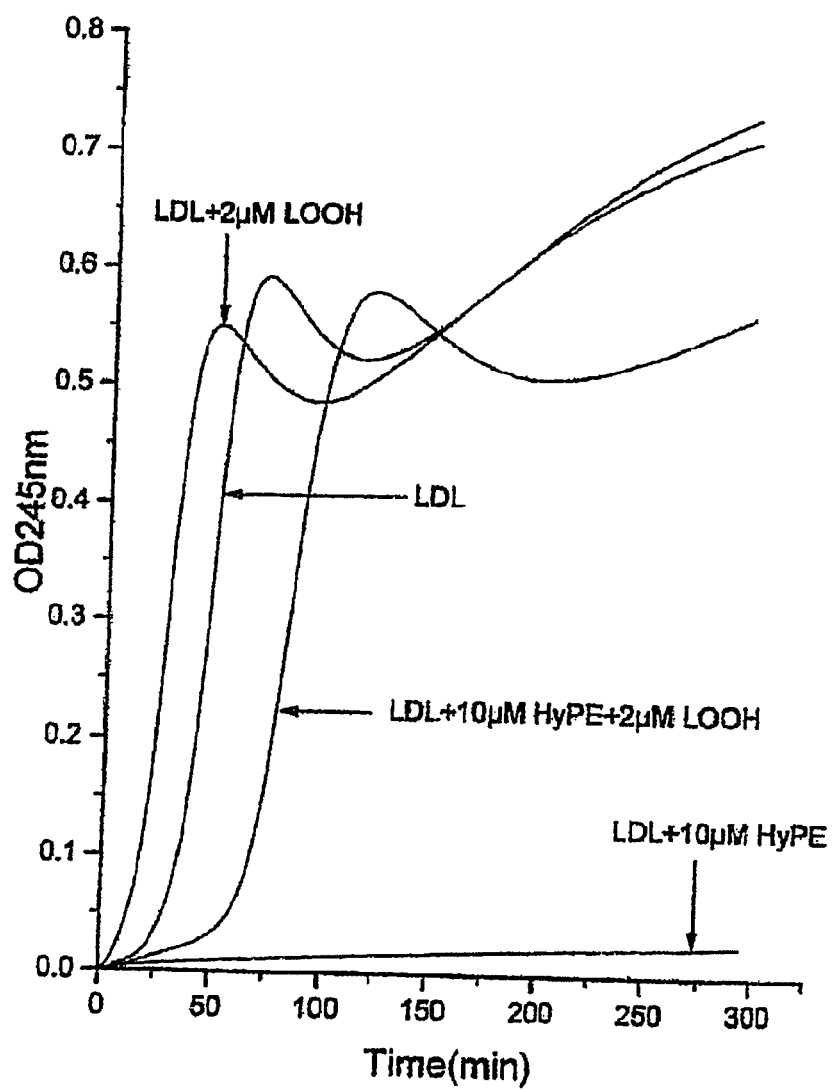

Fig. 3.1: Effect of different Lipid-conjugates on LPS-induced IL-8 production.
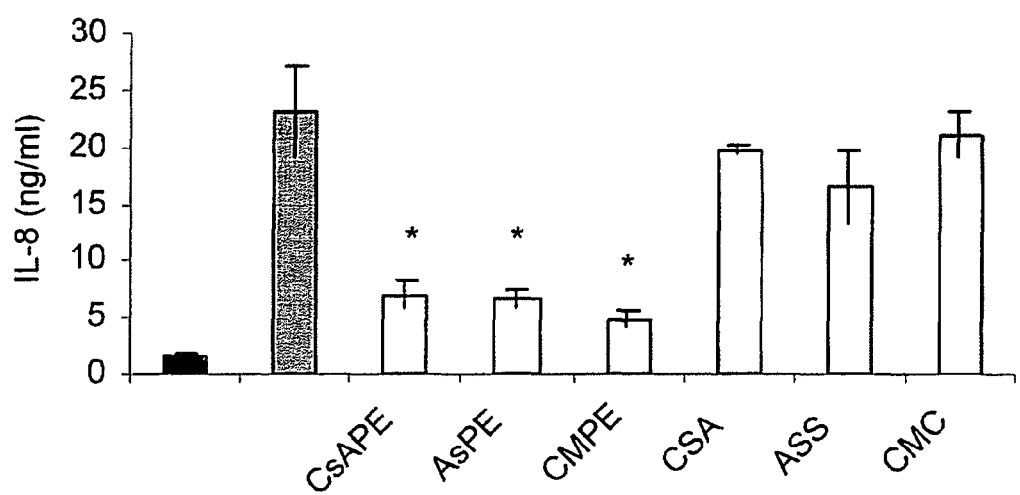

Fig. 3.2: Effect of HyPE on LPS-induced chemokine production.
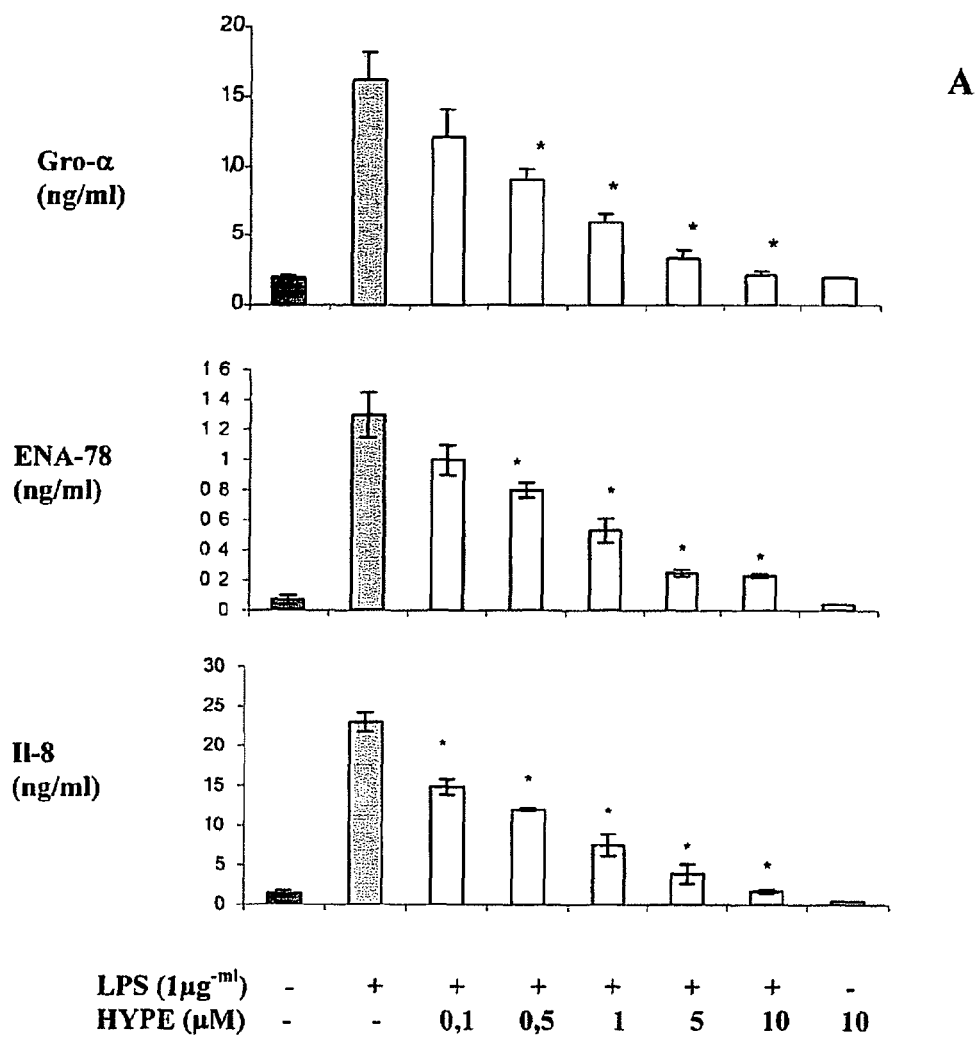
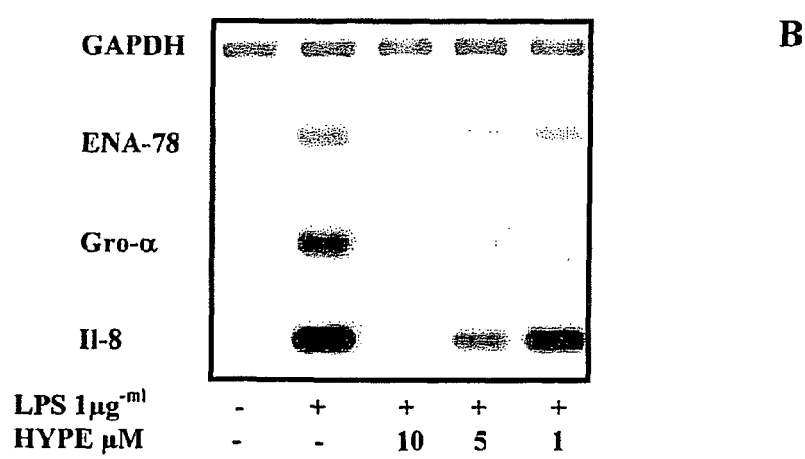

Fig. 3.3: Effect of HyPE on LTA-induced IL-8 production.
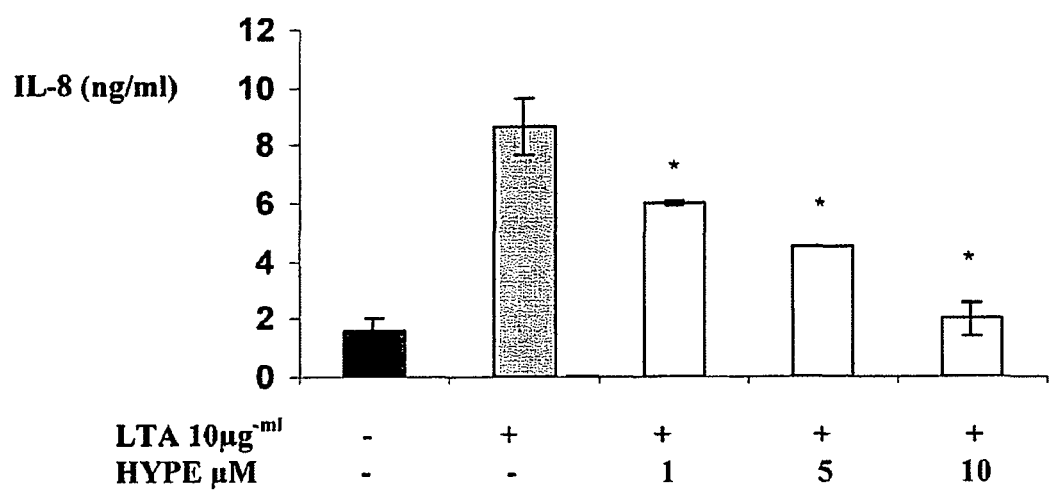

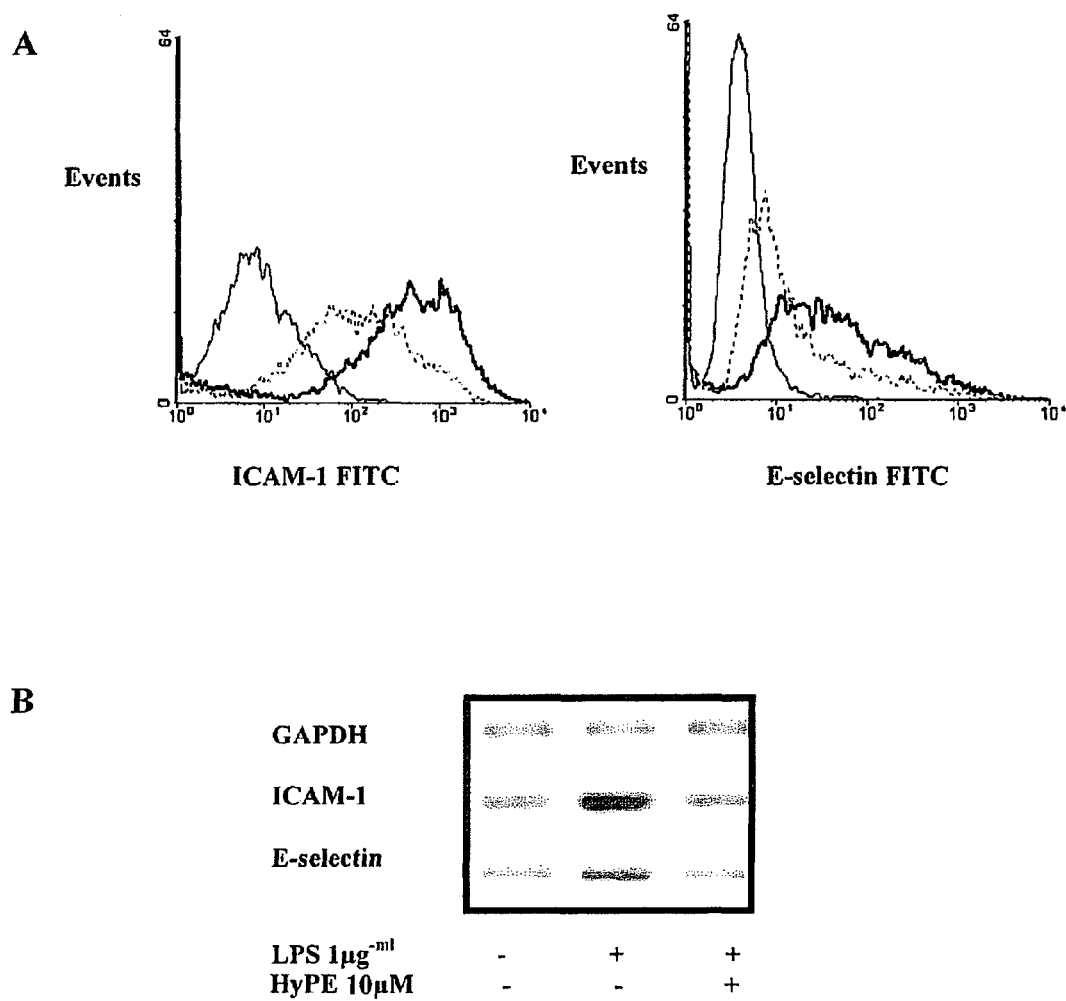
Fig. 3.4: Effect of HyPE on LPS-induced ICAM-1 and E-selectin expression.

Fig. 3.5: Effect of HyPE on LPS-induced activation of NF-kB in LMVEC.
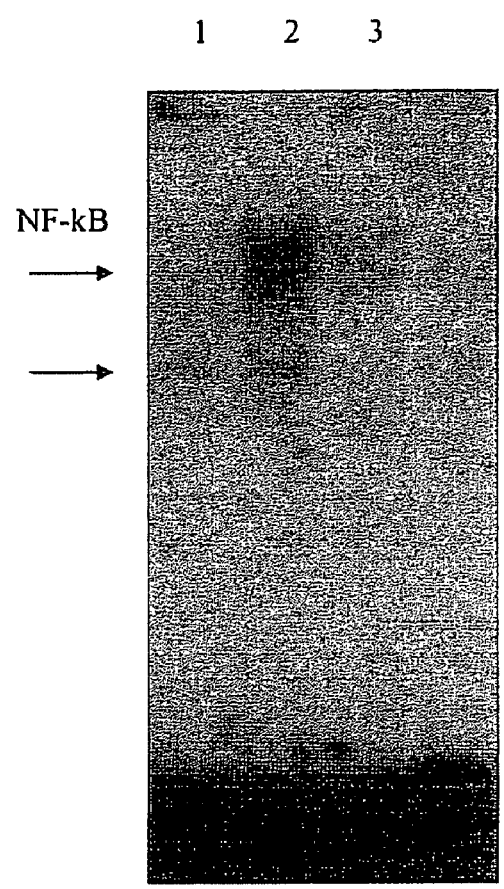

USE OF LIPID CONJUGATES IN THE TREATMENT OF DISEASE

CROSS REFERENCE TO RELATED APPLICATIONS

This application is a continuation-in-part application of U.S. application Ser. No. 10/989,606, filed Nov. 17, 2004 now U.S. Pat. No. 7,811,999 and of U.S. application Ser. No. 10/989,607, filed Nov. 17, 2004, now U.S. Pat. No. 7,772,196 which are continuation-in-part applications of U.S. application Ser. No. 10/627,981 filed Jul. 28, 2003, now U.S. Pat. No. 7,101,859 which is a continuation-in-part application of U.S. application Ser. No. 09/756,765, filed Jan. 10, 2001, now U.S. Pat. No. 7,034,006 which claims priority from a Provisional Application U.S. Ser. No. 60/174,907, filed Jan. 10, 2000; and a continuation-in-part application of PCT International Application PCT/IL2005/001225, filed Nov. 17, 2005, which are hereby incorporated by reference.

FIELD OF THE INVENTION

This invention provides a method of preventing asthma, allergic rhinitis, or chronic obstructive pulmonary disease in a subject comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof. This invention also provides a method of treating allergic rhinitis or chronic obstructive pulmonary disease in a subject comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof.

BACKGROUND OF THE INVENTION

Lipid-conjugates having a pharmacological activity of inhibiting the enzyme phospholipase A2 (PLA2, EC 3.1.1.4) are known in the prior art. Phospholipase A2 catalyzes the breakdown of phospholipids at the sn-2 position to produce a fatty acid and a lysophospholipid. The activity of this enzyme has been correlated with various cell functions, particularly with the production of lipid mediators such as eicosanoid production (prostaglandins, thromboxanes and leukotrienes), platelet activating factor and lysophospholipids. Since their inception, lipid-conjugates have been subjected to intensive laboratory investigation in order to obtain a wider scope of protection of cells and organisms from injurious agents and pathogenic processes.

SUMMARY OF THE INVENTION

In one embodiment, the invention provides for the use of a compound represented by the structure of the general formula (A):

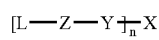
(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to prevent asthma.

In another embodiment, the invention provides for the use of a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to treat allergic rhinitis.

In another embodiment, the invention provides for the use of a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to prevent allergic rhinitis.

In another embodiment, the invention provides for the use of a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to treat chronic obstructive pulmonary disease, In another embodiment, the invention provides for the use of a compound represented by the structure of the general formula (A):

$$[L-Z-Y\frac{}{n}X] \quad (A)$$

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to prevent chronic obstructive pulmonary disease In one embodiment, X in general formula (A) is a polysaccharide. In one embodiment, the polysaccharide is carboxymethylcellulose, while in another embodiment, the polysaccharide is a glycosaminoglycan. In one embodiment, the glycosaminoglycan is hyaluronic acid, while in another embodiment, the glycosaminoglycan is heparin. In one embodiment L in general formula (A) is phosphatidylethanolamine, which in one embodiment is dipalmitoyl phosphatidylethanolamine.

BRIEF DESCRIPTION OF FIGURES

FIG. 1.1: Inhibition of endothelin-1 (ET)-induced contraction of rat tracheal rings by Lipid-conjugates. A: Contraction of rat trachea by Endothelin-1. B: Effect of HyPE on ET-induced contraction of rat trachea.

FIG. 1.2: Effect of HyPE and Hyaluronic acid (HA) on ET-1 induced contraction of rat trachea.

FIG. 1.3: Effect of HyPE and Hyaluronic acid (HA) on Acetylcholine (AcCh)-induced contraction of isolated rat trachea rings.

FIG. 1.4: Effect of HyPE, administered subcutaneously, on early asthmatic reaction (EAR) induced by ovalbumin inhalation FIG. 1.5: Effect of HyPE on sPLA$_2$ expression in lung of rats with OVA-induced asthma.

FIG. 1.6: Effect of HyPE on cysteinyl leukotriens (LTC$_4$, LTD$_4$ and LTE$_4$) level in the BAL of OVA-induced asthmatic rats.

FIG. 1.7: Effect of HyPE inhalation on early and late asthmatic reaction (EAR and LAR, respectively) in OVA-sensitized asthmatic rats.

FIG. 1.8: Effect of HyPE inhalation on cysteinyl leukotriens (LTC4, LTD4 and LTE4) level in the BAL of OVA-sensitized asthmatic rats.

FIG. 1.9: Effect of HyPE inhalation on NO production by macrophages collected from the BAL of OVA-sensitized asthmatic rats.

FIG. 1.10: Effect of HyPE inhalation on structural change in airways (airway remodeling) of OVA sensitized asthmatic rats.

FIG. 1.11: Effect of HyPE on remodeling of asthmatic rat airway; histological morphometry.

FIG. 1.12: Effect of HyPE inhalation on TNFα production by macrophages collected from the BAL of OVA-sensitized asthmatic rats.

FIG. 1.13: Amelioration of OVA-induced broncho-constriction by HyPE inhalation before challenge.

FIG. 14: Amelioration of OVA-induced broncho-constriction by HyPE inhalation after challenge.

FIG. 2.1: CMPE protects BGM cells from membrane lysis induced by combined action of hydrogen peroxide (produced by glucose oxidase=GO), and exogenous phospholipase A$_2$ (PLA$_2$).

FIG. 2.2: CMPE protects BGM cells from glycosaminoglycan degradation by Hydrogen peroxide (produced by GO).

FIG. 2.3: HyPE protects LDL from copper-induced oxidation.

FIG. 3.1: Effect of different Lipid-conjugates on LPS-induced IL-8 production.

FIG. 3.2: Effect of HyPE on LPS-induced chemokine production.

FIG. 3.3: Effect of HyPE on LTA-induced IL-8 production.

FIG. 3.4: Effect of HyPE on LPS-induced ICAM-1 and E-selectin expression.

FIG. 3.5: Effect of HyPE on LPS-induced activation of NF-kB in LMVEC.

DETAILED DESCRIPTION OF THE INVENTION

The invention provides lipid-conjugates which display a wide-range combination of cytoprotective pharmacological activities. These compounds can alleviate airway obstruction in asthma, protect mucosal tissue in gastrointestinal disease, suppress immune responses, alleviate cutaneous hypersensitivity reactions, inhibit cell proliferation associated with vascular injury and immunological responses, inhibit cell migration associated with vascular and central nervous system disease, attenuate oxidative damage to tissue proteins and cell membranes, interfere with viral spread, reduce tissue destroying enzyme activity, and reduce intracellular levels of chemokines and cytokines. Thus these compounds are useful in the treatment of a diversity of disease states, including asthma, rhinitis, allergic rhinitis, chronic obstructive pulmonary disease, obstructive respiratory disease, colitis, Crohn's disease, central nervous system insult, multiple sclerosis, contact dermatitis, psoriasis, cardiovascular disease, invasive medical procedures, invasive cellular proliferative disorders, anti-oxidant therapy, hemolytic syndromes, sepsis, acute respiratory distress syndrome, tissue transplant rejection syndromes, autoimmune disease, viral infection, and hypersensitivity conjunctivitis In another embodiment, the invention provides for the use of a compound represented by the structure of the general formula (A):

$$[L-Z-Y\frac{}{n}X] \quad (A)$$

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to prevent asthma.

In another embodiment, the invention provides for the use of a compound represented by the structure of the general formula (A):

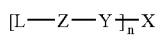 (A)

wherein
L is a lipid or a phospholipid:
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to treat allergic rhinitis.

In another embodiment, the invention provides for the use of a compound represented by the structure of the general formula (A):

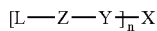 (A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to prevent allergic rhinitis.

In another embodiment, the invention provides for the use of a compound represented by the structure of the general formula (A):

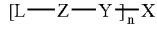 (A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to treat chronic obstructive pulmonary disease.

In another embodiment, the invention provides for the use of a compound represented by the structure of the general formula (A):

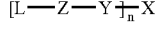 (A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to prevent chronic obstructive pulmonary disease.

In another embodiment, the present invention provides for the use of a compound represented by the structure of the general formula (A):

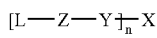 (A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to treat a subject suffering from an obstructive respiratory disease In another embodiment, the present inventions provides for the use of a compound represented by the structure of the general formula (A):

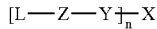 (A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000
for the preparation of a composition to prevent obstructive respiratory disease.

In one embodiment, the obstructive respiratory disease is asthma. In another embodiment, the obstructive respiratory disease is rhinitis. In another embodiment, the obstructive respiratory disease is allergic rhinitis. In another embodiment, the obstructive respiratory disease is chronic obstructive pulmonary disorder. In another embodiment, the obstructive respiratory disease is sinusitis.

In one embodiment, X in general formula (A) is a polysaccharide. In one embodiment, the polysaccharide is carboxymethylcellulose, while in another embodiment, the polysaccharide is a glycosaminoglycan. In one embodiment, the glycosaminoglycan is hyaluronic acid, while in another embodiment, the glycosaminoglycan is heparin. In one embodiment L in general formula (A) is phosphatidylethanolamine, which in one embodiment is dipalmitoyl phosphatidylethanolamine.

In one embodiment, "treating" or "preventing" refers to delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, preventing relapse to a disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics.

In one embodiment, symptoms are primary, while in another embodiment, symptoms are secondary. In one embodiment, "primary" refers to a symptom that is a direct result of infection with a pathogen, while in one embodiment, "secondary" refers to a symptom that is derived from or consequent to a primary cause.

In one embodiment, the invention provides a method of treating a subject suffering from an obstructive respiratory disease, comprising the step of administering to a subject a compound comprising a lipid or phospholipid moiety bond to a physiologically acceptable monomer, dimer, oligomer, or polymer, and/or a pharmaceutically acceptable salt or a pharmaceutical product thereof, in an amount effective to treat the subject suffering from an obstructive respiratory disease. In another embodiment, the invention provides a method of treating a subject suffering from an obstructive respiratory disease, comprising the step of administering to a subject any one of the compounds according to the invention, in an amount effective to treat the subject suffering from an obstructive respiratory disease. In another embodiment, the obstructive respiratory disease is asthma.

In one embodiment of the invention, the physiologically acceptable monomer is either a salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate; or wherein the physiologically acceptable dimer or oligomer is a dipeptide, a disaccharide, a trisaccharide, an oligopeptide, or a di- or trisaccharide monomer unit of heparin, heparan sulfate, keratin, keratan sulfate, chondroitin, chondoitin sulfate, dermatin, dermatan sulfate, dextran, or hyaluronic acid; or wherein the physiologically acceptable polymer is a glycosaminoglycan, polygelin ('hemaccell'), alginate, hydroxyethyl starch (hetastarch), polyethylene glycol, polycarboxylated polyethylene glycol, chondroitin sulfate, keratin, keratin sulfate, heparan sulfate, dermatin, dermatan sulfate, carboxymethylcellulose, heparin, dextran, or hyaluronic acid. In another embodiment, the physiologically acceptable polymer is chondrotin sulfate. In another embodiment, the chondrotin sulfate is chondrotin-6-sulfate, chondroitin-4-sulfate or a derivative thereof. In another embodiment, the physiologically acceptable polymer is hyaluronic acid.

In one embodiment of the invention, the lipid or phospholipid moiety is either phosphatidic acid, an acyl glycerol, monoacylglycerol, diacylglycerol, triacylglycerol, sphingosine, sphingomyelin, chondroitin-4-sulphate, chondroitin-6-sulphate, ceramide, phosphatidylethanolamine, phosphatidylserine, phosphatidylcholine, phosphatidylinositol, or phosphatidylglycerol, or an ether or alkyl phospholipid derivative thereof, and the physiologically acceptable monomer or polymer moiety is either aspirin, lactobionic acid, maltose, glutaric acid, polyethylene glycol, carboxymethylcellulose, heparin, dextran, hemacell, hetastarch, or hyaluronic acid. In another embodiment, the phospholipid moiety is phosphatidylethanolamine In one embodiment, obstructive respiratory disease is a disease of luminal passages in the lungs, marked by dyspnea, tachypnea, or auscultatory or radiological signs of airway obstruction. Obstructive respiratory disease comprises asthma, acute pulmonary infections, acute respiratory distress syndrome, chronic obstructive pulmonary disease, rhinitis, and allergic rhinitis. In one embodiment, the pathophysiology is attributed to obstruction of air flow due to constriction of airway lumen smooth muscle and accumulation of infiltrates in and around the airway lumen In one embodiment, asthma is a disease process wherein the bronchi may be narrowed, making breathing difficult. In one embodiment, symptoms comprise wheezing, difficulty breathing (particularly exhaling air), tightness in the chest, or a combination thereof. In one embodiment, factors which can exacerbate asthma include rapid changes in temperature or humidity, allergies, upper respiratory infections, exercise, stress, smoke (cigarette), or a combination thereof.

In one embodiment, rhinitis comprises an inflammation of the mucous membrane of the nose. In one embodiment, allergic rhinitis is an inflammatory response in the nasal passages to an allergic stimulus. In one embodiment, symptoms comprise nasal congestion, sneezing, runny, itchy nose, or a combination thereof.

In one embodiment, chronic obstructive pulmonary disease is a progressive disease process that most commonly results from smoking. In one embodiment, chronic obstructive pulmonary disease comprises difficulty breathing, wheezing, coughing, which may be a chronic cough, or a combination thereof. In one embodiment, chronic obstructive pulmonary disease may lead to health complications, which in one embodiment, may comprise bronchitis, pneumonia, lung cancer, or a combination thereof.

Colitis is a chronic disease of the gastrointestinal lumen, marked by abdominal discomfort, diarrhea and, upon radiological or histological diagnosis, characteristic signs of mucosal damage including epithelial denudation. Crohn's disease is a related disorder affecting typically the small intestine but which may involve any region of the gastrointestinal tract.

Multiple sclerosis is a disease of white matter, marked by motor weakness or sensory disturbance, or both, usually diagnosed by spinal fluid analysis or magnetic resonance imaging. Visual disturbance, including blindness, is common as well. In regions of disease activity, the blood brain barrier is impaired.

Skin hypersensitivity reactions, otherwise known as contact dermatitis, are marked by external signs of tissue irritation such as localized redness, swelling, and pruritis. Virtually any substance may produce the condition, and it is one of the most common complaints diagnosed by dermatologists.

Psoriasis is also one of the most common dermatologic diseases, affecting 1 to 2 percent of people. The most common areas of involvement are the elbows, knees, gluteal cleft, and the scalp. In active lesions of psoriasis, the rate of epidermal cell replications is accelerated. Long-term use of topical glucocorticoids is often accompanied by loss of effectiveness, Cardiovascular disease refers to both disorders of blood vessel lumen narrowing as well as to resultant ischemic syndromes of the target organs they supply, such as heart, kidney, and brain. Ischemia, or reduced blood supply, results from the narrowing of a blood vessel. The signs and symptoms of cardiovascular disease include, among others, angina pectoris, weakness, dyspnea, transient ischemic attacks, stroke, and renal insufficiency. Diagnosis is based on clinical grounds in conjunction with anciliary diagnostic tests, such as blood tests, electrocardiograms, echography, and angiography. Atherosclerosis is a common element in cardiovasular disease in which narrowing of the blood vessel lumen is due to scar-like plaques formed from reactive, migrating, and proliferating cells and from local incorporation of blood fat, cholesterol, and lipoprotein. Of particular significance in this respect is the accumulation of low density lipoprotein (LDL), which may be accelerated when damaged by oxidation. Plaques are considered to be the sites for both acute and chronic stenotic lesions, wherein the risk of tissue ischemia rises.

Stenotic or narrowing lesions of blood vessels occur not only in atherosclerosis but in other systemic cardiovascular disorders as well. Among these are arterial hypertension, vasculitides, including the vasculitis associated with transplanted organs, and coagulative disorders. Many of these disorders, particularly hypertension, atherosclerosis, and vasculitis occur concommitantly in the same patient.

Reperfusion injury and ischemia/reperfusion injury refers to the tissue injury and initiation of necrosis following the resumption of blood flow to a previously ischemic tissue. This phenomenon is recognized as an important component of ischemic and post-ischemic types of injury, particularly to brain and heart tissue. One pathophysiological mechanism which predominates in reperfusion is the damaging effect of reactive oxygen species, otherwise known as oxidative damage or free radial injury. Nitric oxide and its radicals are also implicated in the pathophysiology. The production of these noxious chemical species is is attributed to the local accumulation, adhesion, and transmigration of leukocytes at the lesion site.

Invasive medical procedures, such as catheterization of arteries or veins or open surgery are frequently associated with tissue ischemia due to blood vessel injury as well as to reperfusion injury, both of which may arise in the course of an invasive procedure. Thus preservation of blood vessel potency and prevention of reperfusion injury are the subject of intense investigation in medical science. Such procedures are performed for both diagnostic and therapeutic purposes, and adjuvant drugs are commonly prescribed to prevent complications of blood vessel injury or restenosis. Formation of these lesions involves a multiplicity of participants, including coagulative elements of the blood, blood cells, and the structural elements and cells of the blood vessel lumen wall. For example, arterial restenosis appearing after successful balloon angioplasty is frequently due to the narrowing of the inner diameter of the artery by the growth (proliferation) of smooth muscle cells in the areas of irritation caused by the balloon angioplasty. This new stenotic lesion may be comprised from other cell types as well, including leukocytes, accumulating at the lesion site through processes of migration and local proliferation. The two events (cell migration and proliferation) are almost certainly due to the coordinated interaction of a number of different cytokines likely released by early accumulation of macrophages at the site of original tissue injury. Thus leukocytes contribute to stenotic lesion formation through the processes of migration, local proliferation, passage through endothelial barriers, accumulation of cholesterol-rich lipoprotein, conversion to foam cells, and secretion of cytokines. This proliferation of cells and narrowing of the vascular lumen is not however restricted or limited to the coronary arteries or cerebral circulation. It can also occur post-operatively causing restenosis in, for example, peripheral vascular systems.

In the context of the present invention, the term cardiovascular disease refers to blood vessel lumen narrowing arising in the course of atherosclerosis, vasculitis, invasive procedures, particularly catheterization of an artery or vein, and the ischemic syndromes associated with them.

Transplantation of tissue, grafts, and organs is frequently complicated by the appearance of host-versus-graft and graft-versus-host disease, both of which may occur acutely or chronically in the recipient of the graft. The source of the graft may be allogeneic (from the same species) or xenogeneic (from another species). Whether as complication due to the induced hyperactive immune response, or through another mechanism, vasculitis remains a frequently encountered complication of tissue transplantation procedures. Moreover, vascular damage due to reperfusion injury is considered to be a major factor in the post-surgical malfunctioning of tissue and organ transplants.

Autoimmune diseases are conditions in which the change in clinical state of the subject is attributed to aberrant cellular and/or humoral immune responses. The most common autoimmune diseases in the U.S. are juvenile diabetes, Hashimoto's and Grave's thryroiditis, rheumatoid arthritis, Crohn's disease and ulcerative colitis, chronic active hepatitis, vitaligo, glomerulonephritis, uveitis, multiple sclerosis, scleroderma, hemolytic anemia, idiopathic thrombocytopenic purpura, myasthenia gravis, systemic lupus erythematosis, and pemphigus.

Hyper-proliferative cellular disorders, such as cancer cells arising at primary organ sites or at other loci of spread (metastases), are one of the leading causes of death in the U.S. Cancers are frequently highly resistant to all forms of treatment including therapy with potent anti-proliferative drugs and radiation. Increasingly the medical community is becoming aware of the critical role played by the vasculature associated with both the primary and metastatic forms of disease. Like any cell cluster, cancer cells are dependent upon a reliable blood supply and in fact, cancer cells are known to encourage the process of de novo vascularization through elaboration of growth factors which act on endothelial cells and smooth muscle cells to form new blood vessels, thus supplying the cancerous growth.

Metastasis, the spread of cancer cells to ectopic sites, is frequently a vasculature dependent process as well, often referred to as hematogenous spread. The physiological barrier imposed by the blood vessel wall, comprised from elements such as endothelial cells and basement membrane substance, is normally highly selective to the passage of cells. However, metastatic cells abrogate this barrier, employing a variety of mechanisms, some of which have been established in the scientific literature. For example, such abnormal cells produce hydrolytic enzymes which degrade the extracellular matrix and associated components of the vascular barrier, such as collagenase, heparinase, and hyaluronidase. Thus a critical factor in the metastatic process is the ability of cancer cells to intrude through or permeate the wall of the blood vessel lumen, thus arriving to invade a new tissue site after travel through the circulation. Cancer cells also elaborate messenger chemicals, known as cytokines and chemokines, which enable the metastatic process, from many aspects, including angiogenesis.

Cellular elaboration of cytokines and chemokines serve an important regulatory function in health; however, when a hyperactive response to stress or disease is triggered, these compounds may present in excess and damage tissue, thereby pushing the disease state toward further deterioration. Cytokine overproduction is involved in numerous diseases, such as sepsis, airway and lung injury, renal failure, transplant rejection, skin injuries, intestine injuries, cancer development and metastasis, central nervous sytem disorders, vaginal bacterial infection, and more. Two examples in which this occurs are systemic infection, in particular when due to blood born bacteria (septicemia), and in the pulmonary condition known as acute (or adult) respiratory distress syndrome (ARDS). In ARDS, lung spaces fill with fluid, impeding gas exchange and producing respiratory failure. Although platelet aggregation occurs, the major offenders appear to be monocytic phagocytes and leukocytes that adhere to endothelial surfaces and undergo a respiratory burst to inflict oxidant injury and release chemokines such as Gro α, ENA-78, CX3X and MCP-1, in addition to leukotrienes, thromboxanes, and prostaglandins. The monocytic phagocytes, mainly macrophages in the alveoli and those lining the vasculature, also release oxidants, mediators, and a series of degradative enzymes that directly damage endothelial cells and cause leukocytes to release their lysosomal enzymes. The mortality rate is over 50%. The most common causes of ARDS are infection, aspiration, smoke and toxin inhalation, as well as systemic processes initiated outside the lung, including bacterial septicemia. The sepsis syndrome and shock are triggered by the interactions of various microbial products in the blood, in particular, gram-negative endotoxins, with host mediator systems. The incidence is estimated to be up to 500,000 cases per year in the U.S. alone, a figure which is considered to rise due to the increasing prevalence of antibiotic resistant organisms. A variety of host mediators have been implicated in the pathogenesis of septicemia and septic shock (referred to collectively herein as sepsis) including factors released from stimulated cells, in particular, cytokines, tumor necrosis factor-α (TNF), Gro α, ENA-78, CX3X and MCP-1, NFκB transcription factor, lysosomal enzymes and oxidants from leukocytes, and products of the metabolism of arachidonic acid, among others.

Red blood cell lysis, or hemolysis, may be an inherited or acquired disorder, giving rise to anemia, iron deficiency, or jaundice. Among the acquired syndromes are membrane anomalies due to direct toxic effects of snake bites or of infectious agents, including viral, bacterial and parasitic etiologies, particularly malaria; exposure to oxidizing substances through ingestion or disease; or as a result of mechanical trauma within abnormal blood vessels. This latter condition, known as microangiopathic hemolysis, is considered to be related in mechanism to the hemolysis produced from blood passage through prosthetic implants, such as heart valves. Inherited red blood cell membrane fragility often occurs due to intracorpuscular enzyme and structural defects, such as glucose 6-phosphatase deficiency, sickle cell anemia, and thalessemia. Red blood cell lysis is one of the limiting factors in the storage life of blood products, particularly when subjected to free-radical forming photodynamic virocidal treatments, such as γ-irradiation.

The acquired immunodeficiency syndrome is considered to be a rapidly growing global epidemic and one route of spread is through contaminated blood products. Transmission and progression of this disease is dependent upon the infective activity of the human immunodeficiency virus. Current therapies are limited primarily to the administration of reverse transcriptase inhibitors, drugs of high expense and low patient tolerability.

Oxidative injury refers to the effect of peroxidation and free radical production on body tissues. To some extent, peroxide production is a normal, physiological process, attributed, for example, a role in immune defense. However, in stress and disease states, or over the natural course of time, as in physiological senescence, the accumulative addition of these unstable chemical moieties to tissue structures, including membrane components and blood proteins, leads to an irreversible pattern of injury. Agents that act as anti-oxidants can protect against oxidative damage. Such protection has been the subject of numerous scientific publications, Intracellular bacterial parasites are one of the most prevelant forms of sexually transmitted disease and are frequently intractable to conventional antibiotic therapy. Vaginal infection with chlamydia species is a salient example.

In one embodiment, the present invention offers methods for the treatment of disease based upon administration of lipids covalently conjugated through their polar head group to a physiologically acceptable chemical moiety, which may be of high or low molecular weight.

In one embodiment, the lipid compounds (Lipid-conjugates) of the present invention are described by the general formula:

[phosphatidylethanolamine-Y]n-X

[phosphatidylserine-Y]n-X

[phosphatidylcholine-Y]n-X

[phosphatidylinositol-Y]n-X

[phosphatidylglycerol-Y]n-X

[phosphatidic acid-Y]n-X

[lyso-phospholipid-Y]n-X

[diacyl-glycerol-Y]n-X

[monoacyl-glycerol-Y]n-X

[sphingomyelin-Y]n-X

[sphingosine-Y]n-X

[ceramide-Y]n-X wherein

Y is either nothing or a spacer group ranging in length from 2 to 30 atoms; and

X is a physiologically acceptable monomer, dimer, oligomer or polymer; and n, the number of lipid molecules bound to X, is a number from 1 to 1000.

In one embodiment of this invention, n is a number from 1 to 1000. In another embodiment, n is a number from 1 to 500. In another embodiment, n is a number from 1 to 100. In another embodiment, n is a number from 100 to 300. In another embodiment, n is a number from 300 to 500. In another embodiment, n is a number from 500 to 800.

In one embodiment, the lipid compounds of this invention, known herein as lipid conjugates (Lipid-conjugates) are now disclosed to possess a combination of multiple and potent pharmacological effects in addition to the ability to inhibit the extracellular form of the enzyme phospholipase A2. The set of compounds comprising phosphatidylethanolamine covalently bound to a physiologically acceptable monomer or polymer, is referred to herein as the PE-conjugates. Related derivatives, in which either phosphatidylserine, phosphatidylcholine, phosphatidylinositol, phosphatidic acid or phosphatidylglycerol are employed in lieu of phosphatidylethanolamine as the lipid moiety provide equivalent therapeutic results, based upon the biological experiments described below for the Lipid-conjugates and the structural similarities shared by these compounds. Other Lipid-conjugate derivatives relevant to this invention are Lipid-conjugates wherein at least one of the fatty acid groups of the lipid moieties at position C1 or C2 of the glycerol backbone are substituted by a long chain alkyl group attached in either ether or alkyl bonds, rather than ester linkage.

As defined by the structural formulae provided herein for the Lipid-conjugates, these compounds may contain between one to one thousand lipid moieties bound to a single physiologically acceptable polymer molecule.

Administration of the Lipid-conjugates in a diversity of animal and cell models of disease invoices remarkable, and unexpected, cytoprotective effects, which are useful in the treatment of disease. They are able to stabilize biological membranes; inhibit cell proliferation; suppress free radical production; suppress nitric oxide production; reduce cell migration across biological barriers; influence chemokine levels, including MCP-1, ENA-78, Gro α, and CX3C; affect gene transcription and modify the expression of MHC antigens; bind directly to cell membranes and change the water structure at the cell surface; inhibit the uptake of oxidized lipoprotein; prevent airway smooth muscle constriction; suppress neurotransmitter release; reduce expression of tumor necrosis factor-α (TNF-α); modify expression of transcription factors such as NFκB; inhibit extracellular degradative enzymes, including collagenase, heparinase, hyaluronidase, in addition to that of PLA2; and inhibit viral infection of white cells. Thus the Lipid-conjugates provide far-reaching cytoprotective effects to an organism suffering from a disease wherein one or more of the presiding pathophysiological mechanisms of tissue damage entails either oxidation insult giving rise to membrane fragility; hyperproliferation behavior of cells giving rise to stenotic plaque formation in vascular tissue, angiogenesis and benign or malignant cancer disease, or psoriasis; aberrant cell migration giving rise to brain injury or tumor cell metastases; excessive expression of chemokines and cytokines associated with central nervous system (CNS) insult, sepsis, ARDS, or immunological disease; cell membrane damage giving rise to CNS insult, CVS disease, or hemolysis; peroxidation of blood proteins and cell membranes giving rise to atherosclerosis or reperfusion injury; excessive nitric oxide production giving rise to CNS insult, reperfusion injury, and septic shock; interaction with major histocompatability antigens (MHC) associated with autoimmune diseases and alloimmune syndromes, such as transplant rejection.

In one embodiment of the present invention, the useful pharmacological properties of the lipid or Lipid-conjugates may be applied for clinical use, and disclosed herein as methods for treatment of a disease. The biological basis of these methods may be readily demonstrated by standard cellular and animal models of disease as described below.

While pharmacological activity of the Lipid-conjugates described herein may be due in part to the nature of the lipid moiety, the multiple and diverse combination of pharmacological properties observed for the Lipid-conjugates emerges ability of the compound structure to act essentially as several different drugs in one chemical entity. Thus, for example, internal mucosal injury, as may occur in colitis or Crohn's disease, may be attenuated by any one or all of the pharmaceutical activities of immune suppression, anti-inflammation, anti-oxidation, nitric oxide production, or membrane stabilization. Protection of blood vessels from periluminal damage, as may occur in atherosclerosis, may entail activity from anti-proliferative, anti-chemokine, antioxidant, or antimigratory effects. Treatment or prevention of asthma, allergic rhinitis, chronic obstructive pulmonary disease, or obstructive respiratory disease may involve any one of the many activities of the Lipid-conjugates ranging from suppression of nitric oxide, anti-chemokine, anti-proliferative, or membrane stabilization effects.

Proliferation of vascular tissue is an element of both the atherogenesis of sclerotic plaques as well as a feature of primary and metastatic cancer lesion growth. Stabilization of biological membranes may prevent hemolysis as well as mucosal bowel injury. Attenuation of chemokine levels may ameliorate ADDS as well as militate against atherogenesis. Anti-oxidant activity protects may protect against reperfusion injury and ischemia/reperfusion injury as well as CNS insult, atherosclerosis, and hemolysis. These and other advantages of the present invention will be apparent to those skilled in the art based on the following description.

The use of a single chemical entity with potent anti-oxidant, membrane-stabilizing, anti-proliferative, anti-chemokine, anti-migratory, and anti-inflammatory activity provides increased cytoprotection relative to the use of several different agents each with a singular activity. The use of a single agent having multiple activities over a combination or plurality of different agents provides uniform delivery of an active molecule, thereby simplifying issues of drug metabolism, toxicity and delivery. The compounds of the present invention also exhibit properties present only in the combined molecule, not in the individual components.

In one embodiment, the compounds of the invention may be used for acute treatment of temporary conditions, or may be administered chronically, especially in the case of progressive, recurrent, or degenerative disease. In one embodiment of the invention, the concentrations of the compounds will depend on various factors, including the nature of the condition to be treated, the condition of the patient, the route of administration and the individual tolerability of the compositions.

In another embodiment, the invention provides low-molecular weight Lipid-conjugates, previously undisclosed and unknown to possess pharmacological activity, of the general formula:

[Phosphatidylethanolamine-Y]n-X

[Phosphatidylserine-Y]n-X

[Phosphatidylcholine-Y]n-X

[Phosphatidylinositol-Y]n-X

[Phosphatidylglycerol-Y]n-X

[Phosphatidic acid-Y]n-X

[lyso-phospholipid-Y]n-X

[diacyl-glycerol-Y]n-X

[monoacyl-glycerol-Y]n-X

[sphingomyelin-Y]n-X

[sphingosine-Y]n-X

[ceramide-Y]n-X wherein
Y is either nothing or a spacer group ranging in length from 2 to 30 atoms; and
X is salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, a dipeptide, a disaccharide, a trisaccharide, an oligosaccharide, an oligopeptide, or a di- or trisaccharide monomer unit of heparin, heparan sulfate, keratin, keratan sulfate, chondroitin, chondoitin-6-sulfate, chondroitin-4- sulfate, dermatin, dermatan sulfate, dextran, or hyaluronic acid, a glycosaminoglycan, polygeline ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid; and n, the number of lipid molecules bound to X, is a number from 1 to 1000

In one embodiment of this invention, n is a number from 1 to 1000. In another embodiment, n is a number from 1 to 500. In another embodiment, n is a number from 1 to 100. In another embodiment, n is a number from 100 to 300. In another embodiment, n is a number from 300 to 500. In another embodiment, n is a number from 500 to 800.

In another embodiment of the invention, these Lipid-conjugate derivatives possess wide-spectrum pharmacological activity and, as pharmaceutical agents administered to treat disease, are considered analogous to the Lipid-conjugates comprised from high molecular weight polymers. Other lipid-conjugate derivatives relevant to this invention are glycerolipid moieties in which at least one of the two long chain alkyl groups in position C1 and C2 of the glycerol backbone are attached in ether or alkyl bonds, rather than ester linkage.

The present invention is further illustrated in the following examples of the therapeutic Lipid-conjugate compounds, their chemical preparation, their anti-disease activity, and methods of use as pharmaceutical compositions in the treatment of disease Compounds In the methods, according to embodiments of the invention, the Lipid-conjugates administered to the subject are comprised from at least one lipid moiety covalently bound through an atom of the polar head group to a monomer or polymeric moiety (referred to herein as the conjugated moiety) of either low or high molecular weight. When desired, an optional bridging moiety can be used to link the Lipid-conjugates moiety to the monomer or polymeric moiety. The conjugated moiety may be a low molecular weight carboxylic acid, dicarboxylic acid, fatty acid, dicarboxylic fatty acid, acetyl salicylic acid, cholic acid, cholesterylhemisuccinate, or mono- or di-saccharide, an amino acid or dipeptide, an oligopeptide, a glycoprotein mixture, a di- or trisaccharide monomer unit of a glycosaminoglycan such as a repeating unit of heparin, heparan sulfate, hyaluronic acid, chondrotin-sulfate, dermatan, keratan sulfate, or a higher molecular weight peptide or oligopeptide, a polysaccharide, polyglycan, protein, glycosaminoglycan, or a glycoprotein mixture. From a composition aspect, phospholipid-conjugates of high molecular weight, and associated analogues, are the subject of U.S. Pat. No. 5,064,817, as well as the publications cited herein.

In one embodiment of the invention, when the conjugated carrier moiety is a polymer, the ratio of lipid moieties covalently bound may range from one to one thousand lipid residues per polymer molecule, depending upon the nature of the polymer and the reaction conditions employed. For example, the relative quantities of the starting materials, or the extent of the reaction time, may be modified in order to obtain Lipid-conjugate products with either high or low ratios of lipid residues per polymer, as desired.

The term "moiety" means a chemical entity otherwise corresponding to a chemical compound, which has a valence satisfied by a covalent bond.

Examples of polymers which can be employed as the conjugated moiety for producing Lipid-conjugates for use in the methods of this invention may be physiologically acceptable polymers, including water-dispersible or -soluble polymers of various molecular weights and diverse chemical types, mainly natural and synthetic polymers, such as glycosaminoglycans, hyaluronic acid, heparin, heparin sulfate, chondrotin sulfate, chondrotin-6-sulfate, chondrotin-4-sulfate, keratin sulfate, dermatin, sulfate, plasma expanders, including polygeline ("Haemaccel", degraded gelatin polypeptide crosslinked via urea bridges, produced by "Behring"), "hydroxyethylstarch" (Htastarch, HES) and extrans, food and drug additives, soluble cellulose derivatives (e.g., methylcellulose, carboxymethylcellulose), polyaminoacids, hydrocarbon polymers (e.g., polyethylene), polystyrenes, polyesters, polyamides, polyethylene oxides (e.g. polyethyleneglycols; polycarboxyethyleneglycol), polyvinnylpyrrolidones, polysaccharides, alginates, assimilable gums (e.g., xanthan gum), peptides, injectable blood proteins (e.g., serum albumin), cyclodextrin, and derivatives thereof.

Examples of monomers, dimers, and oligomers which can be employed as the conjugated moiety for producing Lipid-conjugates for use in the methods of the invention may be mono- or disaccharides, carboxylic acid, dicarboxylic acid, fatty acid, dicarboxylic fatty acid, acetyl salicylic acid, cholic acid, cholesterylhemisuccinate, and di- and trisaccharide unit monomers of glycosaminoglycans including heparin, heparan sulfate, hyaluronic acid, chondrotin, chondioitin-6-sulfate, chondroitin-4-sulfate, dermatin, dermatan sulfate, keratin, keratan sulfate, or dextran.

In some cases, according to embodiments of the invention, the monomer or polymer chosen for preparation of the Lipid-conjugate may in itself have select biological properties. For example, both heparin and hyaluronic acid are materials with known physiological functions. In the present invention, however, the Lipid-conjugates formed from these substances as starting materials display a new and wider set of pharmaceutical activities than would be predicted from administration of either heparin or hyaluronic acid which have not been bound by covalent linkage to a phospholipid. It can be shown, by standard comparative experiments as described below, that phosphatidylethanolamine (PE) linked to carboxymethylcellulose (referred to as CMPE, CMC-Peor CME), to hyaluronic acid (referred to as HYPE, HyPE, and Hyal-PE), to heparin (referred to as HEPPE, HepPE, HePPE, Hepa-PE), to chondroitine sulfate A (referred to as CSAPE, CsaPE, CsAPE), to Polygeline (haemaccel) (referred to HemPE, HEMPE), or to hydroxyethyl starch (referred to as HesPE, HESPE), are far superior in terms of potency and range of useful pharmaceutical activity to the free conjugates (the polymers above and the like). In fact, these latter substances are, in general, not considered useful in methods for treatment of most of the diseases described herein, and for those particular cases wherein their use is medically prescribed, such as ischemic vascular disease, the concentrations for their use as drugs are are several orders of magnitude higher. Thus, the combination of a phospholipid such as phosphatidylethanolamine, or related phospholipids which differ with regard to the polar head group, such as phosphatidylserine (PS), phosphatidylcholine (PC), phosphatidylinositol (PI), and phosphatidylglycerol (PG), results in the formation of a compound which has novel pharmacological properties when compared to the starting materials alone The biologically active lipid conjugates described herein can have a wide range of molecular weight, e.g., above 50,000 (up to a few hundred thousands) when it is desirable to retain the Lipid conjugate in the vascular system and below 50,000 when targeting to extravascular systems is desirable. The sole limitation on the molecular weight and the chemical structure of the conjugated moiety is that it does not result in a Lipid-conjugate devoid of the desired biological activity, or lead to chemical or physiological instability to the extent that the Lipid-conjugate is rendered useless as a drug in the method of use described herein, In one embodiment, the compound according to the invention is represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein X is a glycosaminoglycan; and
n is a number from 1 to 1000;
wherein any bond between L, Z, Y and X is either an amide or an esteric bond.

In another embodiment, the compound according to the invention is represented by the structure of the general formula (I):

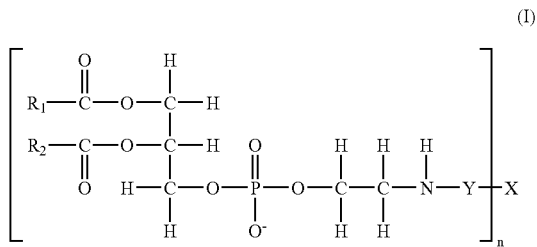

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms; and
X is either a physiologically acceptable monomer, dimer, oligomer or a physiologically acceptable polymer, wherein X is a glycosaminoglycan; and
n is a number from 1 to 1,000;
wherein if Y is nothing the phosphatidylethanolamine is directly linked to X via an amide bond and if Y is a spacer, the spacer is directly linked to X via an amide or an esteric bond and to the phosphatidylethanolamine via an amide bond.

Preferred compounds for use in the methods of the invention comprise one of the following as the conjugated moiety X: acetate, butyrate, glutarate, succinate, dodecanoate, didodecanoate, maltose, lactobionic acid, dextran, alginate, aspirin, cholate, cholesterylhemisuccinate, carboxymethylcellulose, heparin, hyaluronic acid, polygeline (haemaccel), polyethyleneglycol, and polycarboxylated polyethylene glycol. The polymers used as starting material to prepare the PE-conjugates may vary in molecular weight from 1 to 2,000 kDa.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. According to the present invention, a most preferred PE moiety is dipalmitoylphosphatidy-ethanolamine.

Phosphatidyl-ethanolamine and its analogues may be from various sources, including natural, synthetic, and semisynthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond, phosphatidylserine (PS) and its analogues, such as palmitoyl-stearoyl-PS, natural PS from various sources, semisynthetic PSs, synthetic, natural and artifactual PSs and their isomers. Other phospholipids useful as conjugated moieties in this invention are phosphatidylcholine (PC), phosphatidylinositol (PI), phosphatidic acid and phosphoatidylglycerol (PG), as well as derivatives thereof comprising either phospholipids, lysophospholipids, phosphatidyic acid, sphingomyel ins, lysosphingomyel ins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

In another embodiment, the compound according to the invention is represented by the structure of the general formula (II):

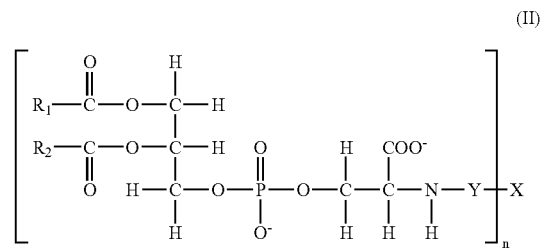

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is a physiologically acceptable monomer, dimer, oligomer or polymer wherein x is a glycosaminoglycan; and
n is a number from 1 to 1000;

wherein if Y is nothing the phosphatidylserine is directly linked to X via an amide bond and if Y is a spacer, the spacer is directly linked to X via an amide or an esteric bond and to the phosphatidylserine via an amide bond.

In another embodiment, the compound according to the invention be [phosphatidylserine-Y]n-X, wherein Y is either nothing or a spacer group ranging in length from 2 to 30 atoms, X is a physiologically acceptable monomer, dimer, oligomer or polymer wherein x is a glycosaminoglycan, and n is a number from 1 to 1000, wherein the phosphatidylserine may be bonded to Y or to X, if Y is nothing, via the COO⁻ moiety of the phosphatidylserine.

In another embodiment, the compound according to the invention is represented by the structure of the general formula (III):

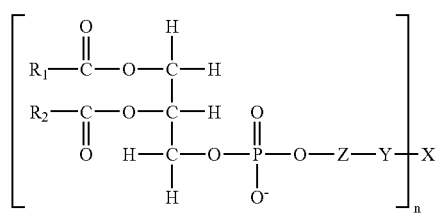

(III)

wherein
$R_1$ is a linear, saturated, mono-unsaturated, or poly-unsaturated, alkyl chain ranging in length from 2 to 30 carbon atoms;
$R_1$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phosphatidyl, Z, Y and X is either an amide or anesteric bond.

In another embodiment, the compound according to the invention is represented by the structure of the general formula (IV):

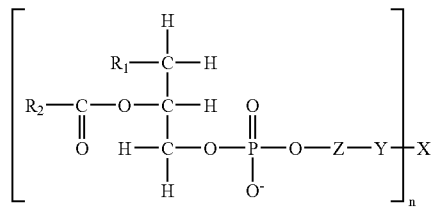

(IV)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In another embodiment, the compound according to the invention is represented by the structure of the general formula (V):

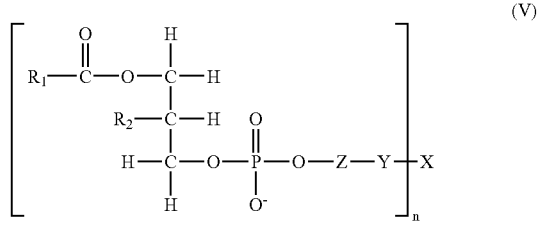

(V)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In another embodiment, the compound according to the invention is represented by the structure of the general formula (VI):

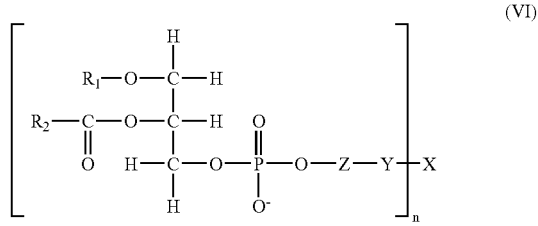

(VI)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either, nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In another embodiment, the compound according to the invention is represented by the structure of the general formula (VII):

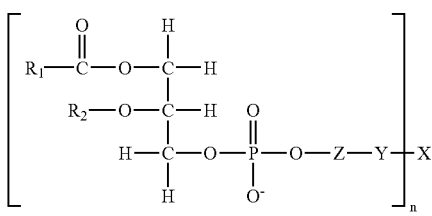

(VII)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond.

In one embodiment of the invention, phosphatidylcholine (PC), Phosphatidylinositol (PI), phosphatidic acid (PA), wherein Z is nothing, and Phosphatidylglycerol (PG) conjugates are herein defined as compounds of the general formula (III).

In one embodiment of the invention Y is nothing Non limiting examples of suitable divalent groups forming the optional bridging group (spacer) Y, according to embodiments of the invention, are straight or branched chain alkylene, e.g., of 2 or more, preferably 4 to 30 carbon atoms, —CO-alkylene-CO, —NH-alkylene-NH—, —CO-alkylene-NH—, —NH-alkylene-NHCO-alkylene-NH—, an amino acid, cycloalkylene, wherein alkylene in each instance, is straight or branched chain and contains 2 or more, preferably 2 to 30 atoms in the chain, —(—O—CH(CH$_3$)CH$_2$—)$_x$— wherein x is an integer of 1 or more.

According to embodiments of the invention, in addition to the traditional phospholipid structure, related derivatives for use in this invention are phospholipids modified at the C1 or C2 position to contain an ether or alkyl bond instead of an ester bond. In one embodiment of the invention, the alkyl phospholipid derivatives and ether phospholipid derivatives are exemplified herein.

In another embodiment, the compound according to the invention is represented by the structure of the general formula (VIII):

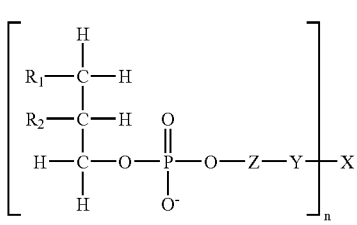

(VIII)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond.

In another embodiment, the compound according to the invention is represented by the structure of the general formula (IX):

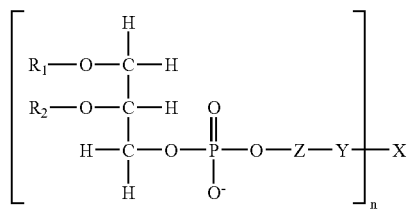

(IX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond.

In another embodiment, the compound according to the invention is represented by the structure of the general formula (IXa):

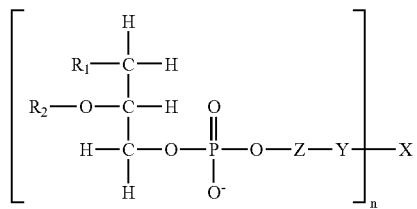

(IXa)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bonds In another embodiment, the compound according to the invention is represented by the structure of the general formula (IXb):

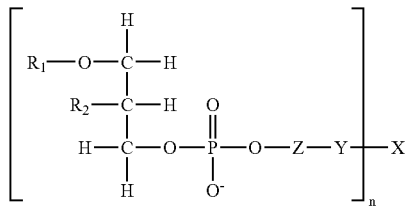

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond.

In another embodiment, the compound according to the invention is represented by the structure of the general formula (X):

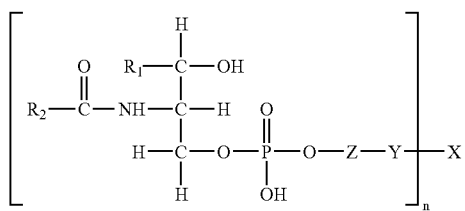

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimes, oligomer, or polymer, wherein x is a glycosaminoglycan; and
n is a number from 1 to 1000;
wherein any bond between the ceramide phosphoryl, Z, Y and X is either an amide or an esteric bond.

In another embodiment, the compound according to the invention is represented by the structure of the general formula (XI):

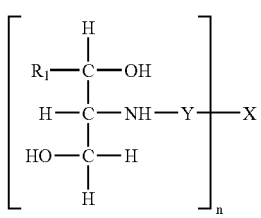

wherein
$R_1$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein if Y is nothing the sphingosyl is directly linked to X via an amide bond and if Y is a spacer, the spacer is directly linked to X and to the sphingosyl via an amide bond and to X via an amide or an esteric bond.

In another embodiment, the compound according to the invention is represented by the structure of the general formula (XII):

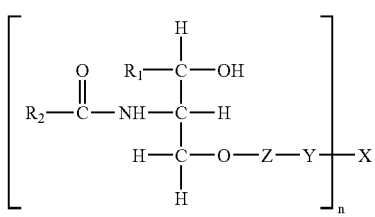

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
L is ceramide;
Z is either nothing, ethanolamine, serine, inositol, choline, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the ceramide, Z, Y and X is either an amide or an esteric bond.

In another embodiment, the compound according to the invention is represented by the structure of the general formula (XIII):

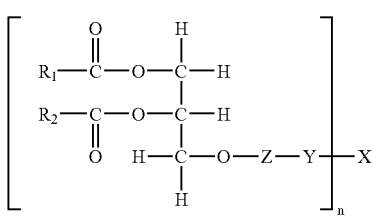

(XIII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the diglyceryl, Z, Y and X is either an amide or an esteric bond.

In another embodiment, the compound according to the invention is represented by the structure of the general formula (XIV):

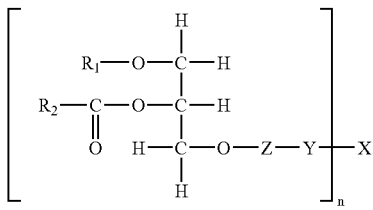

(XIV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the glycerolipid, Z, Y and X is either an amide or an esteric bond.

In another embodiment, the compound according to the invention is represented by the structure of the general formula (XV):

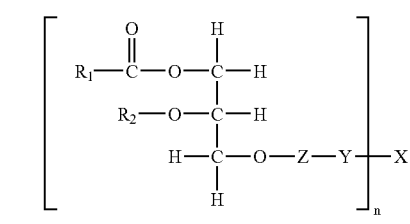

(XV)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the glycerolipid, Z, Y and X is either an amide or an esteric bond.

In another embodiment, the compound according to the invention is represented by the structure of the general formula (XVI):

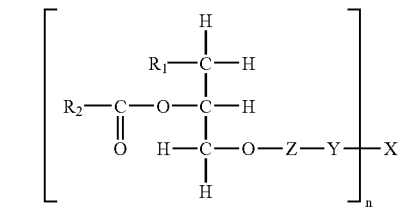

(XVI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In another embodiment, the compound according to the invention is represented by the structure of the general formula (XVII):

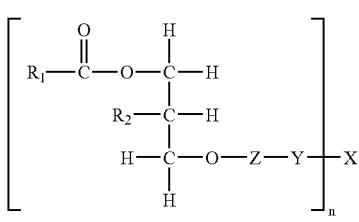

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In another embodiment, the compound according to the invention is represented by the structure of the general formula (XVIII):

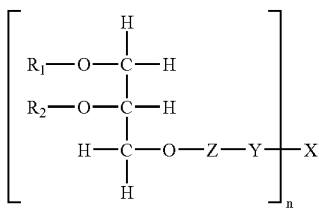

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In another embodiment, the compound according to the invention is represented by the structure of the general formula (XIX):

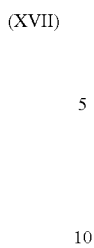

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer; oligomer or polymer, wherein x is a glycosaminoglycan; and n is a number from 1 to 1000;

wherein any bond between the lipid, Z, Y and X is either an amide or an esteric bond.

In another embodiment, the compound according to the invention is represented by the structure of the general formula (XX):

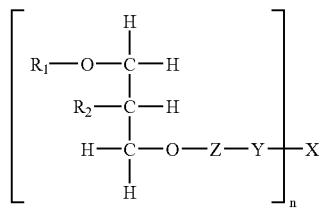

wherein $R_1$ is either hydrogen or a linear-saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond.

In another embodiment, the compound according to the invention is represented by the structure of the general formula (XXI):

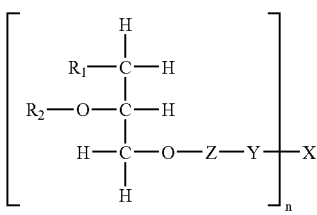 (XXI)

wherein
R₁ is either hydrogen or a linear, saturated, mono-unsaturated, or poly-unsaturated, alkyl chain ranging in length from 2 to 30 carbon atoms;
R₂ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the lipid, Z, Y and X is either an amide or an esteric bond In one embodiment of the invention, the glycosaminoglycan may be, inter alia, hyaluronic acid, heparin, heparan sulfate, chondrotin sulfate, keratin, keratan sulfate, dermatan sulfate or a derivative thereof.

In another embodiment, the glycosaminoglycan is di- and trisaccharide unit monomers of glycosaminoglycans. In another embodiment, the chondroitin sulfate may be, inter alia, chondroitin-6-sulfate, chondroitin-4-sulfate or a derivative thereof.

In one embodiment of the invention, the sugar rings of the glycosaminoglycan are intact. In another embodiment, intact refers to closed. In another embodiment, intact refers to natural. In another embodiment, intact refers to unbroken.

In one embodiment of the invention, the structure of the lipid or phospholipids in any compound according to the invention is intact. In another embodiment, the natural structure of the lipid or phospholipids in any compound according to the invention is maintained.

In one embodiment, the compounds according to the invention are biodegradable.

In one embodiment, the compound according to the invention is a compound represented by the structure of the general formula (A):

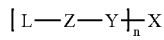 (A)

wherein
L is phosphatidyl;
Z is ethanolamine, wherein L and Z are chemically bonded resulting in phosphatidylethanolamine;
Y is nothing;
X is hyaluronic acid; and
n is a number from 1 to 1000;
wherein any bond between the phosphatidylethanolamine and the hyaluronic acid is an amide bond.

In one embodiment, the compound according to the invention is a compound represented by the structure of the general formula (A):

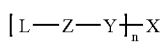 (A)

wherein
L is phosphatidyl;
Z is ethanolamine, wherein L and Z are chemically bonded resulting in phosphatidylethanolamine;
Y is nothing;
X is chondroitin sulfate; and
n is a number from 1 to 1000;
wherein any bond between the phosphatidylethanolamine and the chondroitin sulfate is an amide bond.

In another embodiment, the invention provides a method of treating a subject suffering from asthma, comprising the step of administering to a subject any one of the compounds according to the invention, or any combination thereof, in an amount effective to treat the subject suffering from asthma. In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In another embodiment, the invention provides a method of preventing asthma in a subject.

In another embodiment, the invention provides a method of treating a subject suffering from rhinitis, comprising the step of administering to a subject any one of the compounds according to the invention, or any combination thereof, in an amount effective to treat the subject suffering from rhinitis. In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In another embodiment, the invention provides a method of preventing rhinitis in a subject.

In another embodiment, the invention provides a method of treating a subject suffering from allergic rhinitis, comprising the step of administering to a subject any one of the compounds according to the invention, or any combination thereof, in an amount effective to treat the subject suffering from allergic rhinitis. In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In another embodiment, the invention provides a method of preventing allergic rhinitis in a subject.

In another embodiment, the invention provides a method of treating a subject suffering from chronic obstructive pulmonary disease, comprising the step of administering to a subject any one of the compounds according to the invention, or any combination thereof, in an amount effective to treat the subject suffering from chronic obstructive pulmonary disease. In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In another embodiment, the invention provides a method of preventing chronic obstructive pulmonary disease in a subject.

In another embodiment, the invention provides a method of treating a subject suffering from an obstructive respiratory disease, comprising the step of administering to a subject any one of the compounds according to the invention, or any combination thereof, in an amount effective to treat the subject suffering from an obstructive respiratory disease. In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof. In another embodiment, the obstructive respiratory disease is asthma. In another embodiment, the obstructive respiratory disease is rhinitis. In another embodiment, the obstructive respiratory disease is allergic rhinitis. In another embodiment, the obstructive respiratory disease is chronic obstructive pulmonary disease. In another embodiment, the invention provides a method of preventing asthma, rhinitis, allergic rhinitis, chronic obstructive pulmonary disease, obstructive respiratory disease or a combination thereof, in a subject.

Illustrative of preferred Lipid-conjugates for use in the methods according to embodiments of this invention are those in which the lipid/phospholipid moiety is linked directly or indirectly through a bridging moiety listed below.

| phospholipid | spacer | polymer (m.w.) | abbreviation |
|---|---|---|---|
| PE | Dicarboxylic acid + Diamine | Polygeline (haemaccel) (4-40 kDa) | HeMPE; HemPE |
| PE | None | Carboxymethyl-cellulose (20-500 kDa) | CMPE; CMC-PE |
| PE | None | Hyaluronic acid (2-2000 kDa) | HYPE (HyPE) |
| PE | Dipalmitoic acid | Hyaluronic acid (2-2000 kDa) | HYPE-dipalmitoyl |
| PE | None | Polyethylene glycol | |
| PE | Y | Hydroxyethyl-starch | HESPE; HesPE |
| PE | Dicarboxylic acid + Diamine | Dextran (1-2,000 kDa) | DexPE |
| PE | None | Dextran (1-2,000 kDa) | DexPE |
| PE | None | Albumin | |
| PE | None | Alginate (2-2000 kDa) | |
| PE | None | Polyarninoacid | |
| PE | None | Lactobionic acid | |
| PE | None | Acetylsali-cylate | |
| PE | None | Cholesteryl-hemmisuccinate | |
| PE | None | Maltose | |
| PE | Y | None | Cholic acid |
| PE | None | Polycarboxylated polyethylene glycol | |
| PE | None | Heparin (05-110 kDa) | HEPPE ;HEPE; HepPE |
| Dimyristoyl-PE | Y | Variable | DMPE |
| Dimyristoyl-PE | Y | Hyaluronic acid | HyDMPE |
| PS | Y | Polygeline (haemaccel) | |
| PS | Y | Heparin | |
| PS | Y | Hyaluronic acid | |
| PC | Y | Polygeline (haemaccel) | |
| PC | Y | Hepariri | |
| PC | Y | Hyaluronic acid | |
| PI | Y | Polygeline (haemaccel) | |
| PI | Y | Heparin | |
| PI | Y | Hyaluronic acid | |
| PG | Y | Polygeline (haemaccel) | |
| PG | Y | Heparin | |
| PE | Y | Chondoitin sulfates CSPE | |
| PE | Y | Polygeline (haemaccel) | |
| PG | Y | Hyaluronic acid | |

In one embodiment of the invention, the compounds administered are HyPE, CSAPE, CMPE, HemPE, HesPE, DexPE and As-PE and pharmaceutically acceptable salts thereof, in combination with a physiologically acceptable carrier or solvent. These polymers, when chosen as the conjugated moiety, may vary in molecular weights from 200 to 2,000,000 Daltons. Various molecular weight species have been shown to have the desired biological efficacy, as shown in the section below.

In addition to the compounds of the Examples, further illustrative compounds of this invention are set forth in the section below.

Novel Compounds

Low molecular weight Lipid-conjugates, in which the conjugated moiety is a monomer such as a salicylate, a bile acid, or cholesterylhemmisuccinate, or a di- or trisaccharide unit monomer of a polyglycosoaminoglycan such as heparin, heparan sulfate, chondrotin-6-sulfate, chondroitin-4-sulfate, hyaluronic acid, keratin, keratan sulfate, dermatin, or dermatin sulfate, have not been described before. According to embodiments of the invention, these new compounds display a similar biological activity profile as demonstrated below for the other Lipid-conjugates and have the general formula

[Phosphatidylethanolamine-Y]$_n$—X

[Phosphatidylserine-Y]$_n$—X

[Phosphatidylcholine-Y]$_n$—X

[Phosphatidylinositol-Y]$_n$—X

[Phosphatidylglycerol-Y]$_n$—X

[Phosphatidic acid-Y]$_n$—X

[lyso-phospholipid-Y]$_n$—X

[diacyl-glycerol-Y]$_n$—X

[monoacyl-glycerol-Y]$_n$—X

[sphingomyelin-Y]$_n$—X

[sphingosine-Y]$_n$—X

[ceramide-Y]$_n$—X wherein
Y is either nothing or a spacer group ranging in length from 2 to 30 atoms;
X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid; and n is the number of lipid moiety molecules bound to a molecule of X wherein n is a number from 1 to 1000.

In one embodiment of this invention, low molecular weight phosphatidylethanolamine (PE)-conjugates are defined hereinabove as the compounds of formula (I) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid; and n is the number of lipid moity molecules bound to a molecule of X wherein n is a number from 1 to 1000.

In one embodiment of this invention, low molecular weight phosphatidylserine (PS)-conjugates are defined hereinabove as the compounds of formula (II) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid; and n is the number of lipid moity molecules bound to a molecule of X wherein n is a number from 1 to 1000.

In one embodiment of this invention, Phosphatidylcholine (PC), Phosphatidylinositol (PI), and Phosphatidylglycerol (PG) conjugates are hereinabove defined as the compounds of formula (III) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid; and n is the number of lipid moity molecules bound to a molecule of X wherein n is a number from 1 to 1000.

Examples of suitable divalent groups forming the optional bridging group Y are straight- or branched-chain alkylene, e.g., of 2 or more, preferably 4 to 18 carbon atoms, —CO-alkylene-CO, —NH-alkylene-NH—, —CO-alkylene-NH—, cycloalkylene, wherein alkylene in each instance, is straight or branched chain and contains 2 or more, preferably 2 to 18 carbon atoms in the chain, —(—O—CH(CH$_3$)CH$_2$—)$_x$— wherein x is an integer of 1 or more.

In another embodiment, in addition to the traditional phospholipid structure, related derivatives for use in this invention are phospholipids modified at the C1 or C2 position to contain an ether or alkyl bond instead of an ester bond. These derivatives are exemplified hereinabove by the general formulae (VIII) and (IX) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid; and n is the number of lipid moity molecules bound to a molecule of X wherein n is a number from 1 to 1000.

In another embodiment, related low molecular weight derivatives for use in this invention are exemplified hereinabove by the general formulae (X), (XI) and (XII) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid; and n is the number of lipid moiety molecules bound to a molecule of X wherein n is a number from 1 to 1000.

In another embodiment, related low molecular weight derivatives for use in this invention are exemplified hereinabove by the general formulae (XIII) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid; and n is the number of lipid moiety molecules bound to a molecule of X wherein n is a number from 1 to 1000.

In another embodiment, related low molecular weight derivatives according to the invention may be exemplified herein by any of the general formulae (A), (I)-(XXI) wherein:

In one embodiment of the invention, X is covalently conjugated to a lipid. In another embodiment, x is covalently conjugated to a lipid via an amide bond. In another embodiment, x is covalently conjugated to a lipid via an esteric bond. In another embodiment, the lipid is phosphatidylethanolamine. In another embodiment, the GAG may be, in inter alia, chondroitin sulfate. In another embodiment, the conjugate is biodegradable.

In one embodiment, the invention provides glycosaminoglycans (GAG) compound covalently conjugated to a lipid to obtain a compound having preferred therapeutic properties. In another embodiment, the GAG compound is covalently conjugated to a lipid via an amide bond. In another embodiment, the GAG compound is covalently conjugated to a lipid via an esteric bond. In another embodiment, the lipid may be, inter alia, phosphatidylethanolamine. In another embodiment, the GAG may be, inter alia, chondroitin sulfate. In another embodiment, the conjugate is biodegradable.

Cell surface GAG play a key role in protecting cells from diverse damaging agents and processes, such as reactive oxygen species and free radicals, endotoxins, cytokines, invasion promoting enzymes, and agents that induce and/or facilitate degradation of extracellular matrix and basal membrane, cell invasiveness, white cell extravasation and infiltration, chemotaxis, and others. In addition, cell surface GAG protect cells from bacterial, viral and parasite infection, and their stripping exposes the cell to interaction and subsequent internalization of the microorganism. Enrichment of cell surface GAG would thus assist in protection of the cell from injurious processes. Thus, In one embodiment of the invention, PLA2 inhibitos were conjugated to GAGs or GAG-mimicking molecules. In another embodiment, these Lipid-conjugates, provides wide-range protection from diverse injurious processes, and are effective in amelioration of diseases that requires cell protection from injurous biochemical medistors.

In another embodiment, GAG-mimicking molecule may be, inter alia, a negatively charged molecule. In another embodiment, GAG-mimicking molecule may be, inter alia, a salicilate derivative. In another embodiment, GAG-mimicking molecule may be, idler alia, a dicarboxylic acid.

Preparation of Compounds

The preparation of some high molecular weight Lipid-conjugates is the subject of U.S. Pat. No. 5,064,817, which is incorporated herein by reference. These synthetic methods are reiterated below and are considered to be applicable as well to the preparation of low molecular, i.e. Lipid-conjugates comprising monomers and dimers as the conjugated moiety, with modifications in the procedure as readily evident to one skilled in the art.

When the starting compound chosen for the conjugated moiety has a substituent which is or can be rendered reactive to a substituent on the starting Lipid compound, the conjugated carrier moiety may be linked directly to lipid molecule(s) to produce the a Lipid-conjugate. When it does not, a bifunctional linking starting material can be used to link the two molecules indirectly.

Lipid-conjugates are prepared by linking a polar conjugate, e.g., a monomer or polymer, directly or indirectly to a PL moiety according to the general reaction schemes delineated in U.S. Pat. No. 5,064,817.

For example, with acylated PE used as precursor for the PE conjugate, various lengths of dicarboxylic acids can be used as spacers. These acids can be linked to natural, semi-synthetic or synthetic PE.

For example, PE can be linked to aminodextran indirectly as delineated in U.S. Pat. No. 5,064,817, Polymers with carboxylic groups, such as polyamino acids, carboxymethyl cellulose or polymers to which fatty acids have been linked, can be linked directly to PE according to the scheme delineated in U.S. Pat. No. 5,064,817.

It is to be understood that these examples are given by way of illustration only and are not to be construed as limiting the invention either in spirit of in scope, as many modifications both in reagents and methods could be possible to those skilled in the art. Based on the wide spectrum of pharmacological properties exhibited by Lipid-conjugates, it is likely that compounds covered by Formula I-XXI, in addition to those explicitly described above, have the same valuable biological activities demonstrate to be useful in the methods of treating disease described below.

In one embodiment, the invention provides a process for the preparation of a compound represented by the structure of the general formula (A):

(A)
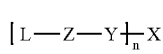

wherein

L is a lipid or a phospholipid;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer, wherein X is a glycosaminoglycan; and n is a number from 1 to 1000;

wherein any bond between L, Z, Y and X is either an amide or an esteric bond, including, inter alia, the steps of:

conjugating L to Z;
conjugating Z to Y;
conjugating Y to X;
wherein if Z is nothing, L is conjugated directly to Y,
if Y is nothing, Z is conjugated directly to X, and
if Y and Z are nothing, L is conjugated directly to X,
thereby preparing a compound represented by the structure of the general formula (A).

In another embodiment, the invention provides a process for the preparation of a compound represented by the structure of the general formula (I):

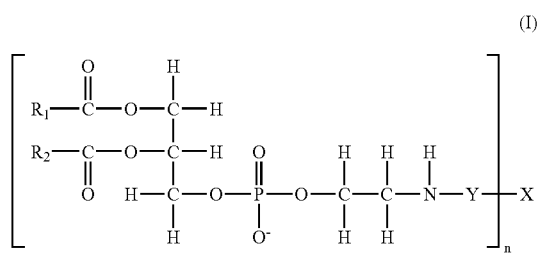

(I)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is either a physiologically acceptable monomer, dimer, oligomer or a physiologically acceptable polymer, wherein X is a glycosaminoglycan; and n is a number from 1 to 1,000;

wherein if Y is nothing the phosphatidylethanolamine is directly linked to X via an amide bond and if Y is a spacer, the spacer is directly linked to X via an amide or an esteric bond and to the phosphatidylethanolamine via an amide bond, including, inter alia, the steps of:

conjugating the phosphatidylethanolamine to Y; and
conjugating Y to X;
if Y is nothing, the phosphatidylethanolamine is conjugated directly to X,
thereby preparing a compound represented by the structure of the general formula (I).

In one embodiment of the invention, the phosphatidylethanolamine is the chemical moiety represented by the structure of:

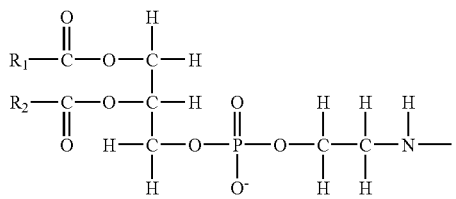

wherein $R_1$ and $R_2$ are defined herein.

In another embodiment, the invention provides a process for the preparation of a compound represented by the structure of the general formula (II):

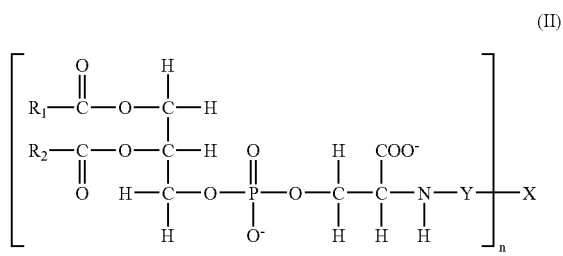

(II)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer wherein x is a glycosaminoglycan; and n is a number from 1 to 1000;

wherein if Y is nothing the phosphatidylserine is directly linked to X via an amide bond and if Y is a spacer, the spacer is directly linked to X via an amide or an esteric bond and to the phosphatidylserine via an amide bond, including, inter alia, the steps of:

conjugating the phosphatidylserine to Y;
conjugating Y to X;
if Y is nothing, the phosphatidylserine is conjugated directly to X,
thereby preparing a compound represented by the structure of the general formula (II).

In one embodiment of the invention, the phosphatidylserine is the chemical moiety represented by the structure of:

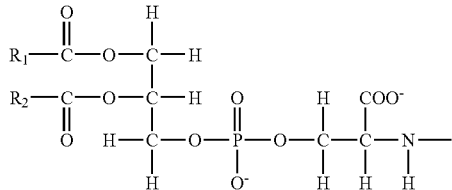

wherein $R_1$ and $R_2$ are defined herein.

In one embodiment, the invention provides a process for the preparation of a compound represented by the structure of the general formula (III):

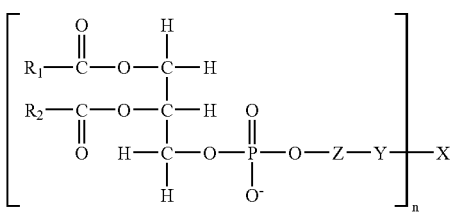
(III)

wherein
R₁ is a linear, saturated, mono-unsaturated, or poly-unsaturated, alkyl chain ranging in length from 2 to 30 carbon atoms:
R₂ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phosphatidyl, Z, Y and X is either an amide or anesteric bond, including, inter alia, the steps of:
  conjugating the phosphatidyl to Z;
  conjugating Z to Y;
  conjugating Y to X;
  wherein if Z is nothing, the phosphatidyl is conjugated directly to Y,
  if Y is nothing, Z is conjugated directly to X, and
  if Y and Z are nothing, the phosphatidyl is conjugated directly to X,
  thereby preparing a compound represented by the structure of the general formula (III).
In one embodiment of the invention, the phosphatidyl may be the chemical moiety represented by the structure of:

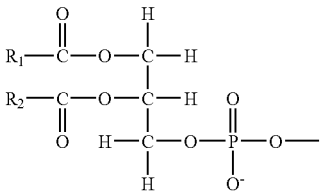

wherein R₁ and R₂ are defined herein
In one embodiment, the invention provides a process for the preparation of a compound represented by the structure of the general formula (IV):

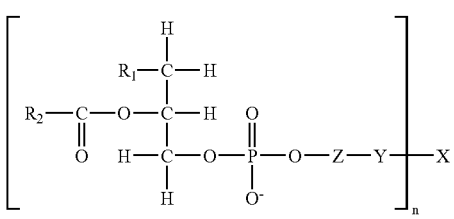
(IV)

wherein
R₁ is either hydrogen or a linear, saturated, mono-unsaturated, or poly-unsaturated, alkyl chain ranging in length from 2 to 30 carbon atoms;
R₂ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond, including, inter alia, the steps of:
  conjugating the phospholipid to Z;
  conjugating Z to Y;
  conjugating Y to X;
  wherein if Z is nothing, the phospholipid is conjugated directly to Y,
  if Y is nothing, Z is conjugated directly to X, and
  if Y and Z are nothing, the phospholipid is conjugated directly to X,
  thereby preparing a compound represented by the structure of the general formula (IV).
In one embodiment of the invention, the phospholipid may be the chemical moiety represented by the structure of:

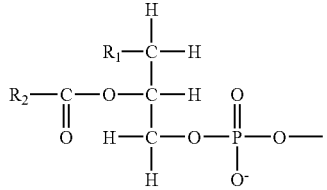

wherein R₁ and R₂ are defined herein.
In one embodiment, the invention provides a process for the preparation of a compound represented by the structure of the general formula (V):

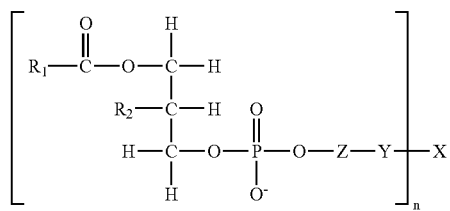
(V)

wherein
R₁ is a linear, saturated, mono-unsaturated, or poly-unsaturated, alkyl chain ranging in length from 2 to 30 carbon atoms;
R₂ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;

wherein any bond between the phospholipid, Z, Y and X is either an amide or an esteric bond, including, inter, alia, the steps of:
    conjugating the phospholipid to Z;
    conjugating Z to Y;
    conjugating Y to X;
    wherein if Z is nothing, the phospholipid is conjugated directly to Y,
    if Y is nothing, Z is conjugated directly to X, and
    if Y and Z are nothing, the phospholipid is conjugated directly to X,
    thereby preparing a compound represented by the structure of the general formula (V).

In one embodiment of the invention, the phospholipid may be the chemical moiety represented by the structure of

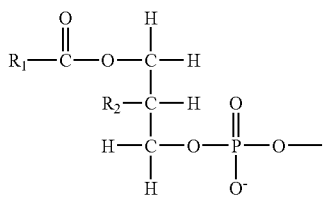

wherein $R_1$ and $R_2$ are defined herein.

In one embodiment, the invention provides a process for the preparation of a compound represented by the structure of the general formula (VI):

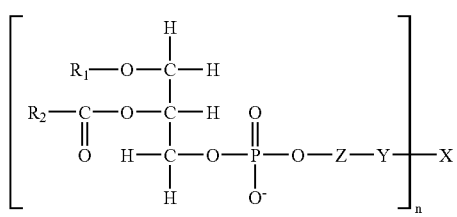

(VI)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
V is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond, including, inter alia, the steps of:
    conjugating the phospholipid to Z;
    conjugating Z to Y;
    conjugating Y to X;
    wherein if Z is nothing, the phospholipid is conjugated directly to Y,
    if Y is nothing, Z is conjugated directly to X, and
    if Y and Z are nothing, the phospholipid is conjugated directly to X, thereby preparing a compound represented by the structure of the general formula (VI).

In one embodiment of the invention, the phospholipid may be the chemical moiety represented by the structure of:

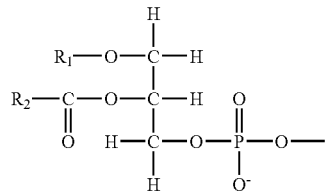

wherein $R_1$ and $R_2$ are defined herein.

In one embodiment, the invention provides a process for the preparation of a compound represented by the structure of the general formula (VII):

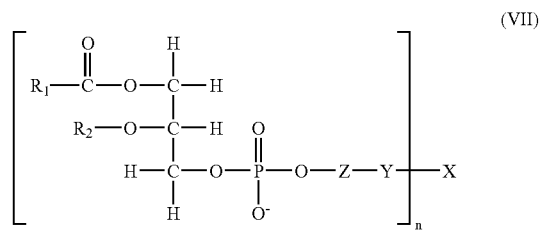

(VII)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer; oligomer, or polymer, wherein x is a glycosaminoglycan; and
n is a number from 1 to 1000;
wherein any bond between the phospholipid, Z, Y and X is either an amide or an esteric bond, including, inter alia, the steps of:
    conjugating the phospholipid to Z;
    conjugating Z to Y;
    conjugating Y to X;
    wherein if Z is nothing, the phospholipid is conjugated directly to Y,
    if Y is nothing, Z is conjugated directly to X, and
    if Y and Z are nothing, the phospholipid is conjugated directly to X, thereby preparing a compound represented by the structure of the general formula (VII).

In one embodiment of the invention, the phospholipid may be the chemical moiety represented by the structure of:

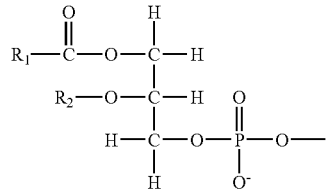

wherein $R_1$ and $R_2$ are defined herein.

In one embodiment, the invention provides a process for the preparation of a compound represented by the structure of the general formula (VIII):

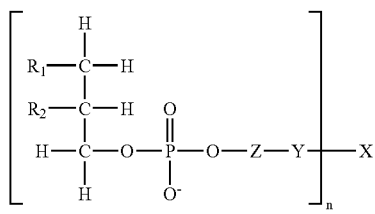

(VIII)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond, including, inter alia, the steps of:

conjugating the phospholipid to Z;

conjugating Z to Y;

conjugating Y to X;

wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (VIII).

In one embodiment of the invention, the phospholipid may be the chemical moiety represented by the structure of:

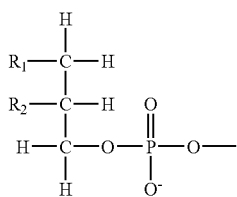

wherein $R_1$ and $R_2$ are defined herein.

In one embodiment, the invention provides a process for the preparation of a compound represented by the structure of the general formula (IX):

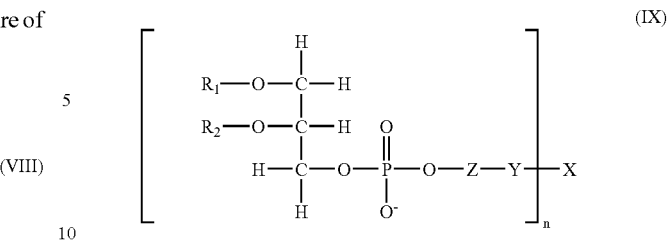

(IX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer, wherein x is a glycosaminoglycan; and n is a number from 1 to 1000;

wherein any bond between the phospholipid, Z, Y and X is either an amide or an esteric bond, including, inter alia, the steps of:

conjugating the phospholipid to Z;

conjugating Z to Y;

conjugating Y to X;

wherein if Z is nothing, the phospholipid is conjugated directly to Y, if Y is nothing, Z is conjugated directly to X, and if Y and Z are nothing, the phospholipid is conjugated directly to X, thereby preparing a compound represented by the structure of the general formula (IX).

In one embodiment of the invention, the phospholipid may be the chemical moiety represented by the structure of:

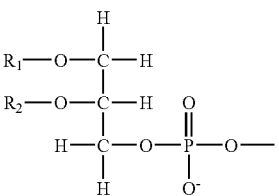

wherein $R_1$ and $R_2$ are defined herein.

In one embodiment, the invention provides a process for the preparation of a compound represented by the structure of the general formula (IXa):

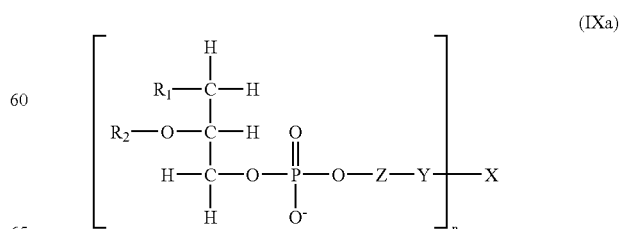

(IXa)

wherein
R₁ is either hydrogen or a linear, saturated, mono-unsaturated, or poly-unsaturated, alkyl chain ranging in length from 2 to 30 carbon atoms;
R₂ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond, including, inter, alia, the steps of:
conjugating the phospholipid to Z;
conjugating Z to Y;
conjugating Y to X;
wherein if Z is nothing, the phospholipid is conjugated directly to Y,
if Y is nothing, Z is conjugated directly to X, and
if Y and Z are nothing, the phospholipid is conjugated directly to X, thereby preparing a compound represented by the structure of the general formula (IXa).

In one embodiment of the invention, the phospholipid may be the chemical moiety represented by the structure of:

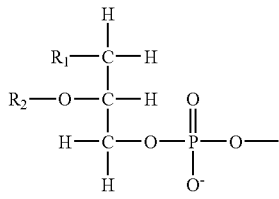

wherein R₁ and R₂ are defined herein.

In one embodiment, the invention provides a process for the preparation of a compound represented by the structure of the general formula (IXb):

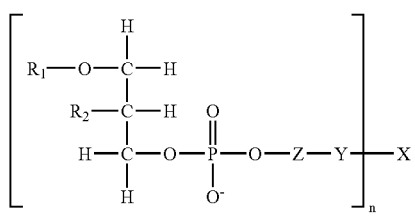

wherein
R₁ is either hydrogen or a linear, saturated, mono-unsaturated, or poly-unsaturated, alkyl chain ranging in length from 2 to 30 carbon atoms;
R₂ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the phospholipid, Z, Y and X is either an amide or an esteric bond, including, inter alia, the steps of:
conjugating the phospholipid to Z;
conjugating Z to Y;
conjugating Y to X;
wherein if Z is nothing, the phospholipid is conjugated directly to Y,
if Y is nothing, Z is conjugated directly to X, and
if Y and Z are nothing, the phospholipid is conjugated directly to X, thereby preparing a compound represented by the structure of the general formula (IXb).

In one embodiment of the invention, the phospholipid may be the chemical moiety represented by the structure of:

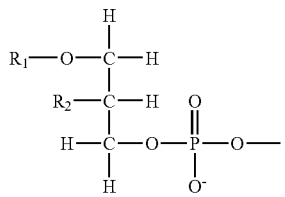

wherein R₁ and R₂ are defined herein.

In one embodiment, the invention provides a process for the preparation of a compound represented by the structure of the general formula (X):

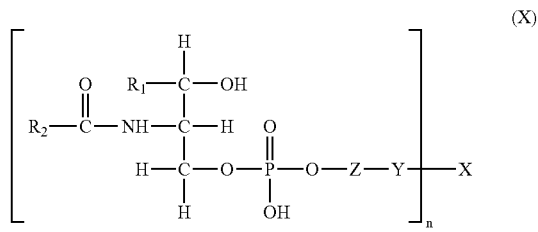

wherein
R₁ is either hydrogen or a linear, saturated, mono-unsaturated, or poly-unsaturated, alkyl chain ranging in length from 2 to 30 carbon atoms;
R₂ is a linear, saturated, mono-unsaturated, or poly-unsaturated, alkyl chain ranging in length from 2 to 30 carbon atoms;
Z is either nothing ethanolamine, serine, inositol, choline, or glycerol;
Y is either nothing or a spacer group ranging in length from 2 to 30 atoms;
X is a physiologically acceptable monomer, dimer, oligomer, or polymer, wherein x is a glycosaminoglycan; and
n is a number from 1 to 1000;
wherein any bond between the ceramide phosphoryl, Z, Y and X is either an amide or an esteric bond, including, inter alia, the steps of:
conjugating the ceramide phosphoryl to Z;
conjugating Z to Y;
conjugating Y to X;
wherein if Z is nothing, the ceramide phosphoryl is conjugated directly to Y,
if Y is nothing, Z is conjugated directly to X, and if Y and Z are nothing, the ceramide phosphoryl is conjugated directly to X, thereby preparing a compound represented by the structure of the general formula (X).

In one embodiment of the invention, the ceramide phosphoryl may be the chemical moiety represented by the structure of:

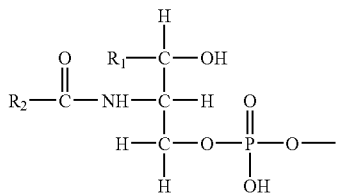

wherein $R_1$ and $R_2$ are defined herein

In one embodiment, the invention provides a process for the preparation of a compound represented by the structure of the general formula (XI):

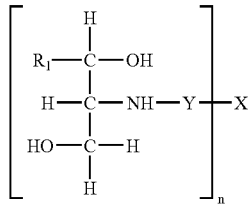

(XI)

wherein
$R_1$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein if Y is nothing the sphingosyl is directly linked to X via an amide bond and if Y is a spacer, the spacer is directly linked to X and to the sphingosyl via an amide bond and to X via an amide or an esteric bond, including, inter alia, the steps of:
conjugating the sphingosyl to Y;
conjugating Y to X;
wherein if Y is nothing, the sphingosyl is conjugated directly to X, thereby preparing a compound represented by the structure of the general formula (XI)

In one embodiment of the invention, the sphingosyl may be the chemical moiety represented by the structure of:

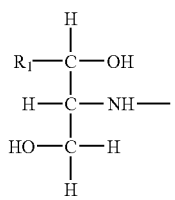

wherein $R_1$ is defined herein.

In one embodiment, the invention provides a process for the preparation of a compound represented by the structure of the general formula (XII):

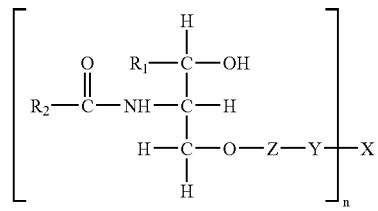

(XII)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
L is ceramide;
Z is either nothing, ethanolamine, serine, inositol, choline, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the ceramide, Z, Y and X is either an amide or an esteric bond, including, inter alia, the steps of:
conjugating the ceramide to Z;
conjugating Z to Y;
conjugating Y to X;
wherein if Z is nothing, the ceramide is conjugated directly to Y,
if Y is nothing, Z is conjugated directly to X, and
if Y and Z are nothing, the ceramide is conjugated directly to X, thereby preparing a compound represented by the structure of the general formula (XII).

In one embodiment of the invention, the ceramide may be the chemical moiety represented by the structure of:

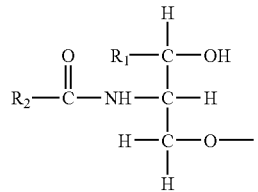

wherein $R_1$ and $R_2$ are defined herein.

In one embodiment, the invention provides a process for the preparation of a compound represented by the structure of the general formula (XIII):

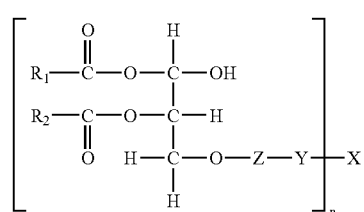

(XIII)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the diglyceryl, Z, Y and X is either an amide or an esteric bond, including, inter alia, the steps of:
conjugating the diglyceryl to Z;
conjugating Z to Y;
conjugating Y to X;
wherein if Z is nothing, the diglyceryl is conjugated directly to Y,
if Y is nothing, Z is conjugated directly to X, and
if Y and Z are nothing, the diglyceryl is conjugated directly to X, thereby preparing a compound represented by the structure of the general formula (XIII).

In one embodiment of the invention, the diglyceryl may be the chemical moiety represented by the structure of:

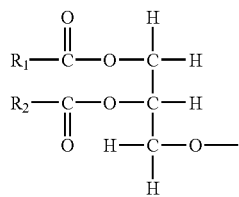

wherein $R_1$ and $R_2$ are defined herein.

In one embodiment, the invention provides a process for the preparation of a compound represented by the structure of the general formula (XIV):

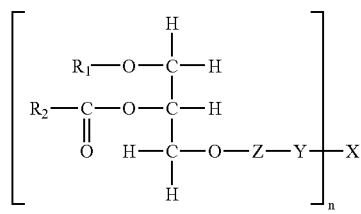

(XIV)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer; oligomer or polymer, wherein x is a glycosaminoglycan; and
n is a number from 1 to 1000;
wherein any bond between the glycerolipid, Z, Y and X is either an amide or an esteric bond, including, inter alia, the steps of:
conjugating the glycerolipid to Z;
conjugating Z to Y;
conjugating Y to X;
wherein if Z is nothing, the glycerolipid is conjugated directly to Y,
if Y is nothing, Z is conjugated directly to X, and
if Y and Z are nothing, the glycerolipid is conjugated directly to X, thereby preparing a compound represented by the structure of the general formula (XIV).

In one embodiment of the invention, the glycerolipid may be the chemical moiety represented by the structure of:

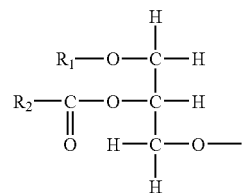

wherein $R_1$ and $R_2$ are defined herein.

In one embodiment, the invention provides a process for the preparation of a compound represented by the structure of the general formula (XV):

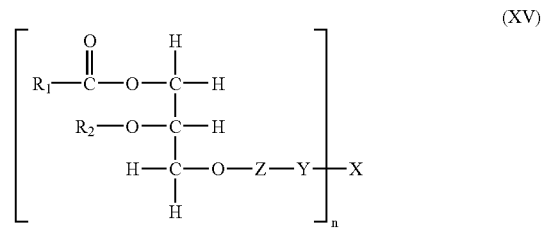

(XV)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the glycerolipid, Z, Y and X is either an amide or an esteric bond, including, inter alia, the steps of:
conjugating the glycerolipid to Z;
conjugating Z to Y;
conjugating Y to X;
wherein if Z is nothing, the glycerolipid is conjugated directly to Y,
if Y is nothing, Z is conjugated directly to X, and
if Y and Z are nothing, the glycerolipid is conjugated directly to X, thereby preparing a compound represented by the structure of the general formula (XV).

In one embodiment of the inventions the glycerolipid may be the chemical moiety represented by the structure of:

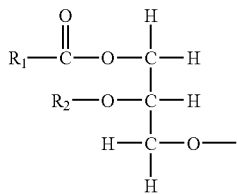

wherein $R_1$ and $R_2$ are defined herein.

In one embodiment, the invention provides a process for the preparation of a compound represented by the structure of the general formula (XVI):

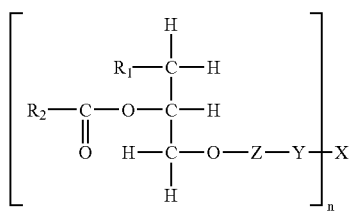

(XVI)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the lipid, Z, Y and X is either an amide or an esteric bond, including, inter alia, the steps of:
conjugating the lipid to Z;
conjugating Z to Y;
conjugating Y to X;
wherein if Z is nothing, the lipid is conjugated directly to Y, if Y is nothing, Z is conjugated directly to X, and
if Y and Z are nothing, the lipid is conjugated directly to X, thereby preparing a compound represented by the structure of the general formula (XVI).

In one embodiment of the invention, the lipid may be the chemical moiety represented by the structure of:

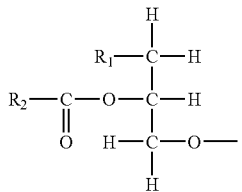

wherein $R_1$ and $R_2$ are defined herein.

In one embodiment, the invention provides a process for the preparation of a compound represented by the structure of the general formula (XVII):

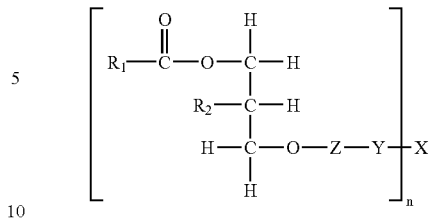

(XVII)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the lipid, Z, Y and X is either an amide or an esteric bond, including, inter alia, the steps of:
conjugating the lipid to Z;
conjugating Z to Y;
conjugating Y to X;
wherein if Z is nothing, the lipid is conjugated directly to Y, if Y is nothing, Z is conjugated directly to X, and
if Y and Z are nothing, the lipid is conjugated directly to X, thereby preparing a compound represented by the structure of the general formula (XVII).

In one embodiment of the invention, the lipid may be the chemical moiety represented by the structure of:

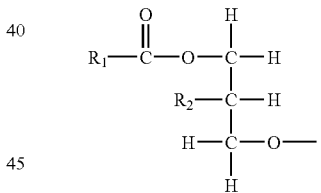

wherein $R_1$ and $R_2$ are defined herein.

In one embodiment, the invention provides a process for the preparation of a compound represented by the structure of the general formula (XVIII):

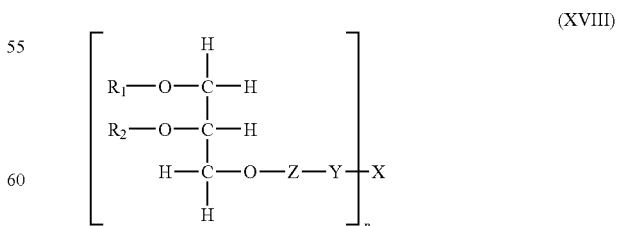

(XVIII)

wherein
$R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond, including, in inter alia, the steps of:
conjugating the lipid to Z;
conjugating Z to Y;
conjugating Y to X;
wherein if Z is nothing, the lipid is conjugated directly to Y,
if Y is nothing, Z is conjugated directly to X, and
if Y and Z are nothing, the lipid is conjugated directly to X, thereby preparing a compound represented by the structure of the general formula (XVIII)

In one embodiment of the invention, the lipid may be the chemical moiety represented by the structure of:

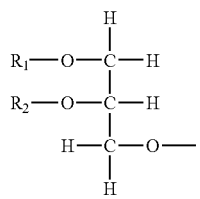

wherein $R_1$ and $R_2$ are defined herein.

In one embodiment, the invention provides a process for the preparation of a compound represented by the structure of the general formula (XIX):

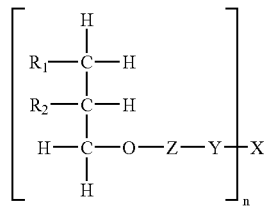

(XIX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond, including, inter alia, the steps of:
conjugating the lipid to Z;
conjugating Z to Y;
conjugating Y to X;
wherein if Z is nothing, the lipid is conjugated directly to Y,
if Y is nothing, Z is conjugated directly to X, and
if Y and Z are nothing, the lipid is conjugated directly to X, thereby preparing a compound represented by the structure of the general formula (XIX)

In one embodiment of the invention, the lipid may be the chemical moiety represented by the structure of:

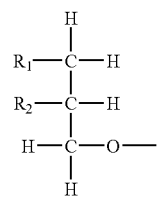

wherein $R_1$ and $R_2$ are defined herein

In one embodiment, the invention provides a process for the preparation of a compound represented by the structure of the general formula (XX):

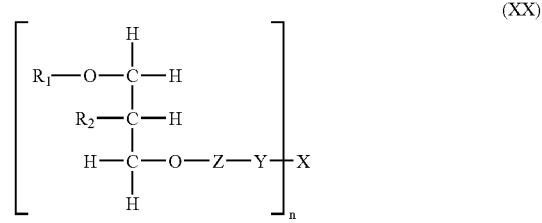

(XX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer, wherein x is a glycosaminoglycan; and n is a number from 1 to 1000;

wherein any bond between the lipid, Z, Y and X is either an amide or an esteric bond, including, inlet alia, the steps of:
conjugating the lipid to Z;
conjugating Z to Y;
conjugating Y to X;
wherein if Z is nothing, the lipid is conjugated directly to Y,
if Y is nothing, Z is conjugated directly to X, and
if Y and Z are nothing, the lipid is conjugated directly to X, thereby preparing a compound represented by the structure of the general formula (XX).

In one embodiment of the invention, the lipid may be the chemical moiety represented by the structure of:

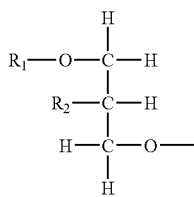

wherein $R_1$ and $R_2$ are defined herein.

In one embodiment, the invention provides a process for the preparation of a compound represented by the structure of the general formula (XXI):

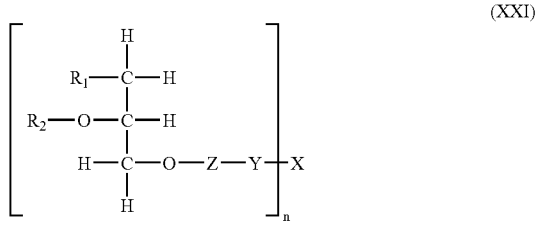

(XXI)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer, wherein x is a glycosaminoglycan; and
n is a number from 1 to 1000;
wherein any bond between the lipid, Z, Y and X is either an amide or an esteric bond, including, inter alia, the steps of:
  conjugating the lipid to Z;
  conjugating Z to Y;
  conjugating Y to X;
  wherein if Z is nothing, the lipid is conjugated directly to Y, if Y is nothing, Z is conjugated directly to X, and
  if Y and Z are nothing, the lipid is conjugated directly to X, thereby preparing a compound represented by the structure of the general formula (XXI).

In one embodiment of the invention, the lipid may be the chemical moiety represented by the structure of:

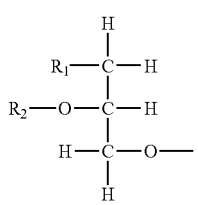

wherein $R_1$ and $R_2$ are defined herein.

In another embodiment, the conjugating according to the invention, may be performed by eliminating a water molecule, thereby forming amide or esteric bonds. In another embodiment, the conjugating may be performed in the presence of a detergent. In another embodiment, the conjugating may be induced by ultrasonic radiation.

In another embodiment, any conjugation process according to the invention may be performed by eliminating a water molecule, thereby forming amide or esteric bonds. In another embodiment, any conjugation process according to the invention may be performed in the presence of a detergent. In another embodiment, any conjugation process according to the invention may be induced by ultrasonic radiation.

In another embodiment, any compound according to the invention may be prepared by a conjugation process performed by eliminating a water molecule, thereby forming amide or esteric bonds. In another embodiment, any compound according to the invention may be prepared by a conjugation process in the presence of a detergent. In another embodiment, any compound according to the invention may be prepared by a conjugation process induced by ultrasonic radiation.

In one embodiment of the invention, the conjugation of the phosphatidylethanolamine and chondroitin sulfate is performed in the presence of a detergent. In another embodiment a detergent may be, inter alia, DDAB Of course any other appropriate detergent may be used.

In one embodiment of the invention, the conjugation of the phosphatidylethanolamine and hyaluronic acid is iduced by sonication.

Methods of Treating Disease Based on PL Conjugates

In one embodiment of the invention, the Lipid-conjugates described herein can be used to treat disease, through exerting at least one of their many pharmacological activities, among which are amelioration, or prevention, of tissue injury arising in the course of pathological disease states by stabilizing cell membranes; limiting oxidative damage to cell and blood components; limiting cell proliferation, cell extravasation and (tumor) cell migratory behavior, suppressing immune responses; or attenuating physiological reactions to stress, as expressed in elevated chemokine levels. The medicinal properties of these compounds are readily exemplified in using animal models of the particular disease in which it is desired to use the drug. The patients to whom the lipid or PL conjugates should be administered are those that are experiencing symptoms of disease or who are at risk of contracting the disease or experiencing a recurrent episode or exacerbation of the disease. The efficacy of these compounds in cellular and animal models of disease are described below in The Examples.

The combination of lipids, such as, but not limited to phosphatidylethanolamine and phosphatidylserine, with additional monomer or polymer moieties, is thus a practical route to die production of new drugs for medical purposes, provided that the resultant chemical composition displays the desired range of pharmacological properties. In the cases described herein, the diversity of biological activities and the effectiveness in disease exhibited by the compounds far exceed the properties anticipated by use of the starting materials themselves, when administered alone or in combination. However, it is likely that the PL conjugate compounds, alone or in combination, will prove to be valuable drugs when adapted to methods of disease treatment other to those conditions specifically described herein.

In one embodiment, the invention provides a method of treating a subject afflicted with a disease related to asthma, rhinitis, allergic rhinitis, chronic obstructive pulmonary disease, obstructive respiratory disease, chlamydia infection, a disorder of smooth muscle cell proliferation, metastatic cancer, colitis, Crohn's disease, or another form of intestinal mucosal injury, cardiovascular disease, atherosclerosis, central nervous system tissue insult, multiple sclerosis, contact dermatitis, psoriasis, cellular proliferative disorder, sepsis, acute respiratory distress syndrome, autoimmune disease, hemolysis, HIV infection, or conjunctivitis.

In one embodiment, the invention provides a method of treating a subject suffering from asthma, including, idler alia, the step of administering to a subject an effective amount of a lipid or phospholipid moiety bonded to a physiologically acceptable monomer, dimer, oligomer, or polymer.

In one embodiment, the invention provides a method of preventing asthma in a subject, including, inter alia, the step of administering to a subject an effective amount of a lipid OT phospholipid moiety bonded to a physiologically acceptable monomer, dimer, oligomer, or polymer.

In one embodiment, the invention provides a method of treating a subject suffering from allergic rhinitis, including, inter alia, the step of administering to a subject an effective amount of a lipid or phospholipid moiety bonded to a physiologically acceptable monomer, dimer, oligomer, or polymer.

In one embodiment, the invention provides a method of preventing allergic rhinitis in a subject, including, inter alia, the step of administering to a subject an effective amount of a lipid or phospholipid moiety bonded to a physiologically acceptable monomer, dimer, oligomer, or polymer.

In one embodiment, the invention provides a method of treating a subject suffering from chronic obstructive pulmonary disease, including, inter alia, the step of administering to a subject an effective amount of a lipid or phospholipid moiety bonded to a physiologically acceptable monomer, dimer, oligomer, or polymer.

In one embodiment, the invention provides a method of preventing chronic obstructive pulmonary disease in a subject, including, inter alia, the step of administering to a subject an effective amount of a lipid or phospholipid moiety bonded to a physiologically acceptable monomer, dimer, oligomer, or polymer.

In one embodiment, the invention provides a method of treating a subject suffering from obstructive respiratory disease, including, inter alia, the step of administering to a subject an effective amount of a lipid or phospholipid moiety bonded to a physiologically acceptable monomer, dimer, oligomer, or polymer.

In one embodiment, the invention provides a method of preventing obstructive respiratory disease in a subject, including, inter alia, the step of administering to a subject an effective amount of a lipid or phospholipid moiety bonded to a physiologically acceptable monomer, dimer, oligomer, or polymer.

In one embodiment, the invention provides a method of treating a subject requiring anti-oxidant therapy, including, infer alia, the step of administering to a subject an effective amount of a lipid or phospholipid moiety bonded to a physiologically acceptable monomer, dimer, oligomer, or polymer, thereby treating the subject requiring an anti-oxidant therapy.

In one embodiment, the invention provides a method treating a subject requiring anti-TNF therapy, including, inter alia, the step of administering to a subject an effective amount of a lipid or phospholipid moiety bonded to a physiologically acceptable monomer, dimer, oligomer, or polymer, thereby treating the subject requiring an anti-TNF therapy.

In one embodiment, the invention provides a method of treating a subject suffering from a disorder of smooth muscle cell proliferation, including, inter alia, the step of administering to a subject an effective amount of a lipid or phospholipid moiety bonded to a physiologically acceptable monomer, dimer, oligomer, or polymer, thereby treating the subject suffering from a disorder related to smooth muscle cell proliferation In one embodiment, the invention provides a method of treating a subject undergoing vascular catheterization, including, inter alia, the step of administering to a subject an effective amount of a lipid or phospholipid moiety bonded to a physiologically acceptable monomer, dimer, oligomer, or polymer, thereby treating the subject undergoing vascular catheterization.

In one embodiment, the invention provides a method of treating a subject suffering from metastatic cancer, including, inter alia, the step of administering to a subject an effective amount of a lipid or phospholipid moiety bonded to a physiologically acceptable monomer, dimer, oligomer, or polymer, thereby treating the subject suffering from metastatic cancer.

In one embodiment, the invention provides a method of treating a subject suffering from colitis, Crohn's disease, or another form of intestinal mucosal injury, including, in inter alia, the step of administering to a subject an effective amount of a lipid or phospholipid moiety bonded to a physiologically acceptable monomer, dimer, oligomer, or polymer, thereby treating the subject suffering from intestinal mucosal injury, including colitis or Crohn's disease.

In one embodiment, the invention provides a method of treating a subject suffering from cardiovascular disease, including, inter alia, the step of administering to a subject an effective amount of a lipid or phospholipid moiety bonded to a physiologically acceptable monomer, dimer, oligomer, or polymer, thereby treating the subject suffering from a cardiovascular disease.

The present invention provides a method of treating a subject suffering from atherosclerosis, including, inter alia, the step of administering to a subject an effective amount of a lipid or phospholipid moiety bonded to a physiologically acceptable monomer, dimer, oligomer, or polymer, thereby treating the subject suffering from atherosclerosis.

In one embodiment, the invention provides a method of treating a subject suffering from central nervous system tissue insult, including, inter alia, the step of administering to a subject an effective amount of a lipid or phospholipid moiety bonded to a physiologically acceptable monomer, dimer; oligomer, or polymer, thereby treating the subject suffering from a central nervous system insult.

In one embodiment, the invention provides a method of treating a subject suffering from multiple sclerosis, including, inter alia, the step of administering to a subject an effective amount of a lipid or phospholipid moiety bonded to a physiologically acceptable monomer, dimer, oligomer, or polymer, thereby treating the subject suffering from multiple sclerosis.

In one embodiment, the invention provides a method of treating a subject suffering from contact dermatitis, including, inter alia, the step of administering to a subject an effective amount of a lipid or phospholipid moiety bonded to a physiologically acceptable monomer, dimer, oligomer, or polymer, thereby treating the subject suffering from contact dermatitis.

In one embodiment, the invention provides a of treating a subject suffering from psoriasis, including, inter alia, the step of administering to a subject an effective amount of a lipid or phospholipid moiety bonded to a physiologically acceptable monomer, dimer, oligomer, or polymer, thereby treating the subject suffering from psoriasis.

In one embodiment, the invention provides a method of treating a subject suffering from a cellular proliferative disorder, including, inter alia, the step of administering to a subject an effective amount of a lipid or phospholipid moiety bonded to a physiologically acceptable monomer, dimer, oligomer, or polymer, thereby treating the subject suffering from a cellular proliferative disorder.

In one embodiment, the invention provides a method of treating a subject suffering from sepsis, including, inter alia, the step of administering to a subject an effective amount of a lipid or phospholipid moiety bonded to a physiologically acceptable monomer, dimer, oligomer, or polymer, thereby treating the subject suffering from sepsis.

In one embodiment, the invention provides a method of treating a subject suffering from ARDS, comprising the steps of administering to a subject an effective amount of a lipid or phospholipid moiety bonded to a physiologically acceptable monomer, dimer, oligomer, or polymer, thereby treating the subject suffering from ARDS.

In one embodiment, the invention provides a method of treating a subject suffering from autoimmune disease, including, inter alia, the step of administering to a subject an effective amount of a lipid or phospholipid moiety bonded to a physiologically acceptable monomer, dimer, oligomer, or polymer, thereby treating the subject suffering from an autoimmune disease.

In one embodiment, the invention provides a method of treating a subject suffering from hemolysis, including, inter alia, the step of administering to a subject an effective amount of a lipid or phospholipid moiety bonded to a physiologically acceptable monomer, dimer, oligomer, or polymer, thereby treating the subject suffering from hemolysis.

In one embodiment, the invention provides a method of treating a subject undergoing tissue transplantation or allograft rejection, including, inter alia, the step of administering to a subject an effective amount of a lipid or phospholipid moiety bonded to a physiologically acceptable monomer, dimer, oligomer, or polymer, thereby treating the subject undergoing tissue transplantation or allograft rejection.

In one embodiment, the invention provides a method of treating a subject afflicted with HIV infection, including, inter alia, the step of administering to a subject an effective amount of a lipid or phospholipid moiety bonded to a physiologically acceptable monomer, dimer, oligomer, or polymer, thereby treating the subject afflicted with HIV infection.

In one embodiment, the invention provides a method of treating a subject afflicted with conjunctivitis, including, inter alia, the step of administering to a subject an effective amount of a lipid or phospholipid moiety bonded to a physiologically acceptable monomer, dimer, oligomer, or polymer, thereby treating the subject afflicted with conjunctivitis.

In one embodiment, the invention provides a method for extracorporeal tissue preservation, including, inter alia, the step of adding to a tissue preparation or organ an effective amount of a lipid or phospholipid moiety bonded to a physiologically acceptable monomer, dimer, oligomer, or polymer, thereby extending the viability of the tissue preparation or organ within a donor subject.

In one embodiment, the invention provides a method of treating a subject afflicted with *Chlamydia* infection, including, inter alia, the step of administering to a subject an effective amount of a lipid or phospholipid moiety bonded to a physiologically acceptable monomer, dimer, oligomer, or polymer, thereby treating the subject afflicted suffering from *Chlamydia* infection.

In one embodiment, the invention provides a use of a lipid or phospholipid moiety bonded to a physiologically acceptable monomer, dimer, oligomer, or polymer, in the preparation of a pharmaceutical composition for treating a subject suffering from asthma.

In one embodiment, the invention provides a use of a lipid or phospholipid moiety bonded to a physiologically acceptable monomer, dimer, oligomer, or polymer, in the preparation of a pharmaceutical composition for preventing asthma in a subject.

In one embodiment, the invention provides a use of a lipid or phospholipid moiety bonded to a physiologically acceptable monomer, dimer, oligomer, or polymer, in the preparation of a pharmaceutical composition for treating a subject suffering from allergic rhinitis.

In one embodiment, the invention provides a use of a lipid or phospholipid moiety bonded to a physiologically acceptable monomer, dimer, oligomer, or polymer, in the preparation of a pharmaceutical composition for preventing allergic rhinitis in a subject.

In one embodiment, the invention provides a use of a lipid or phospholipid moiety bonded to a physiologically acceptable monomer, dimer, oligomer, or polymer, in the preparation of a pharmaceutical composition for treating a subject suffering from chronic obstructive pulmonary disease.

In one embodiment, the invention provides a use of a lipid or phospholipid moiety bonded to a physiologically acceptable monomer, dimer, oligomer, or polymer, in the preparation of a pharmaceutical composition for preventing chronic obstructive pulmonary disease in a subject.

In one embodiment, the invention provides a use of a lipid or phospholipid moiety bonded to a physiologically acceptable monomer, dimer, oligomer, or polymer, in the preparation of a pharmaceutical composition for treating a subject suffering from obstructive respiratory disease.

In one embodiment, the invention provides a use of a lipid or phospholipid moiety bonded to a physiologically acceptable monomer, dimer, oligomer, or polymer, in the preparation of a pharmaceutical composition for preventing obstructive respiratory disease in a subject.

In one embodiment, the invention provides a use of a lipid or phospholipid moiety bonded to a physiologically acceptable monomer, dimer, oligomer, or polymer, in the preparation of a pharmaceutical composition for treating a subject requiring an anti-oxidant therapy.

In one embodiment, the invention provides a use of a lipid or phospholipid moiety bonded to a physiologically acceptable monomer, dimer, oligomer, or polymer, in the preparation of a pharmaceutical composition for treating a subject requiring an anti-TNF therapy.

In one embodiment, the invention provides a use of a lipid or phospholipid moiety bonded to a physiologically acceptable monomer, dimer, oligomer- or polymer, in the preparation of a pharmaceutical composition for treating a subject suffering from a disorder related to smooth muscle cell proliferation.

In one embodiment, the invention provides a use of a lipid or phospholipid moiety bonded to a physiologically acceptable monomer, dimer, oligomer, or polymer, in the preparation of a pharmaceutical composition for treating a subject undergoing vascular catheterization.

In one embodiment, the invention provides a use of a lipid or phospholipid moiety bonded to a physiologically acceptable monomer, dimer, oligomer, or polymer, in the preparation of a pharmaceutical composition for treating a subject suffering form metastatic cancer.

In one embodiment, the invention provides a use of a lipid or phospholipid moiety bonded to a physiologically acceptable monomer, dimer, oligomer, or polymer, in the preparation of a pharmaceutical composition for treating a subject suffering from intestinal mucosal injury, including inter alia, colitis or Crohn's disease.

In one embodiment, the invention provides a use of a lipid or phospholipid moiety bonded to a physiologically acceptable monomer, dimer, oligomer, or polymer in the preparation of a pharmaceutical composition for treating a subject suffering from a cardiovascular disease.

In one embodiment, the invention provides a use of a lipid or phospholipid moiety bonded to a physiologically acceptable monomer, dimer, oligomer, or polymer, in the preparation of a pharmaceutical composition for treating a subject suffering from atherosclerosis.

In one embodiment, the invention provides a use of a lipid or phospholipid moiety bonded to a physiologically acceptable monomer, dimer, oligomer, or polymer, in the preparation of a pharmaceutical composition for, treating a subject suffering from central nervous system insult.

In one embodiment, the invention provides a use of a lipid or phospholipid moiety bonded to a physiologically acceptable monomer, dimer, oligomer, or polymer, in the preparation of a pharmaceutical composition for treating a subject suffering from multiple sclerosis.

In one embodiment, the invention provides a use of a lipid or phospholipid moiety bonded to a physiologically acceptable monomer, dimer, oligomer, or polymer, in the preparation of a pharmaceutical composition for treating a subject suffering from contact dermatitis.

In one embodiment, the invention provides a use of a lipid or phospholipid moiety bonded to a physiologically acceptable monomer, dimer, oligomer, or polymer, in the preparation of a pharmaceutical composition for treating a subject suffering from psoriasis.

In one embodiment, the invention provides a use of a lipid or phospholipid moiety bonded to a physiologically acceptable monomer, dimer, oligomer, or polymer, in the preparation of a pharmaceutical composition for treating a subject suffering from a cellular proliferative disorder.

In one embodiment, the invention provides a use of a lipid or phospholipid moiety bonded to a physiologically acceptable monomer, dimer, oligomer, or polymer, in the preparation of a pharmaceutical composition for treating a subject suffering from sepsis.

In one embodiment, the invention provides a use of a lipid or phospholipid moiety bonded to a physiologically acceptable monomer, dimer; oligomer, or polymer, in the preparation of a pharmaceutical composition for treating a subject suffering from ARDS.

In one embodiment, the invention provides a use of a lipid or phospholipid moiety bonded to a physiologically acceptable monomer, dimer, oligomer, or polymer, in the preparation of a pharmaceutical composition for treating a subject suffering from an autoimmune disease.

In one embodiment, the invention provides a use of a lipid or phospholipid moiety bonded to a physiologically acceptable monomer, dimer, oligomer, or polymer, in the preparation of a pharmaceutical composition for treating a subject suffering from hemolysis.

In one embodiment, the invention provides a use of a lipid or phospholipid moiety bonded to a physiologically acceptable monomer, dimer, oligomer, or polymer, in the preparation of a pharmaceutical composition for treating a subject undergoing tissue transplantation or allograft rejection.

In one embodiment, the invention provides a use of a lipid or phospholipid moiety bonded to a physiologically acceptable monomer, dimer, oligomer, or polymer, in the preparation of a pharmaceutical composition for treating a subject afflicted with HIV infection.

In one embodiment, the invention provides a use of a lipid or phospholipid moiety bonded to a physiologically acceptable monomer, dimer, oligomer, or polymer, in the preparation of a pharmaceutical composition for treating a subject afflicted with conjunctivitis.

In one embodiment, the invention provides a use of a lipid or phospholipid moiety bonded to a physiologically acceptable monomer, dimer, oligomer, or polymer, in the preparation of a pharmaceutical composition for extending the viability of the tissue preparation or organ within a donor subject.

In one embodiment, the invention provides a use of a lipid or phospholipid moiety bonded to a physiologically acceptable monomer, dimer, oligomer, or polymer, in the preparation of a pharmaceutical composition for treating a subject afflicted with *Chlamydia* infection.

In one embodiment of the invention, the treatment requires controlling the expression production and activity of phospholipase enzymes. In another embodiment, the treatment requires controlling the production and/or action of lipid mediators. In another embodiment, the treatment requires amelioration of damage to glycosaminoglycans (GAG) and proteoglycans. In another embodiment, the treatment requires controlling the production and action of oxidants, oxygen radicals and nitric oxide. In another embodiment, the treatment requires anti-oxidant therapy. In another embodiment, the treatment requires anti-endotoxin therapy. In another embodiment, the treatment requires controlling the expression, production or action of cytokines, chemokines, adhesion molecules or interleukines. In another embodiment, the treatment requires protection of lipoproteins from damaging agents. In another embodiment, the treatment requires controlling the proliferation of cells. In another embodiment, the treatment requires controlling of angiogenesis and organ vascularization. In another embodiment, the treatment requires inhibition of invasion-promoting enzymes. In another embodiment, the treatment requires controlling of cell invasion. In another embodiment, the invading cells are white blood cells. In another embodiment, the invading cells are cancer cells. In another embodiment, the treatment requires controlling of white cell activation, adhesion or extravasation. In another embodiment, the treatment requires amelioration of ischemia or reperfusion injury. In another embodiment, the treatment requires inhibition of lymphocyte activation. In another embodiment, the treatment requires protection of blood brain barrier. In another embodiment, the treatment requires control of neurotransmitter production and action. In another embodiment, the treatment requires controlling of blood vessel and airway contraction. In another embodiment, the treatment requires extracorporeal tissue preservation.

In one embodiment of the invention, the lipid mediator is a glycerolipid. In another embodiment, the lipid mediator is a phospholipid. In another embodiment, the lipid mediator is sphingolipid. In another embodiment, the lipid mediator is a sphingosine. In another embodiment, the lipid mediator is ceramide. In another embodiment, the lipid mediator is a fatty acid. In another embodiment, the fatty acid is arachidonic acid. In another embodiment, the lipid mediator is an arachidonic acid-derived eicosanoid. In another embodiment, the lipid is mediator is a platelet activating factor (PAF). In another embodiment, the lipid mediator is a lysophospholipid.

In one embodiment of the invention, the damaging agent is a phospholipase. In another embodiment, the damaging agent is a reactive oxygen species (ROS). In another embodiment, the damaging agent is a free radical. In another embodiment, the damaging agent is a lysophospholipid. In another embodiment, the damaging agent is a fatty acid or a derivative thereof. In another embodiment, the damaging agent is hydrogen peroxide. In another embodiment, the damaging agent is a phospholipid. In another embodiment, the damaging agent is an oxidant. In another embodiment, the damaging agent is a cationic protein. In another embodiment, the damaging agent is a streptolysin. In another embodiment, the damaging agent is a protease. In another embodiment, the damaging agent is a hemolysin. In another embodiment, the damaging agent is a sialidase.

In one embodiment of the invention, the invasion-promoting enzyme is collagenase. In another embodiment, the invasion-promoting enzyme is matrix-metaloproteinase (MMP). In another embodiment, the invasion-promoting enzyme is heparinase. In another embodiment, the invasion-promoting enzyme is heparanase. In another embodiment, the invasion-promoting enzyme is hyaluronidase. In another embodiment, the invasion-promoting enzyme is gelatinase. In another embodiment, the invasion-promoting enzyme is chondroitinase. In another embodiment, the invasion-promoting enzyme is dermatanase. In another embodiment, the invasion-promoting enzyme is keratanase. In another embodiment, the invasion-promoting enzyme is protease. In another embodiment, the invasion-promoting enzyme is lyase. In another embodiment, the invasion-promoting enzyme is hydrolase. In another embodiment, the invasion-promoting enzyme is a glycosaminoglycan degrading enzyme. In another embodiment, the invasion-promoting enzyme is a proteoglycan degrading enzyme.

In one embodiment of the invention, the physiologically acceptable monomer is salicylate. In another embodiment, the physiologically acceptable monomer is salicylic acid. In another embodiment, the physiologically acceptable monomer is aspirin. In another embodiment, the physiologically acceptable monomer is a monosaccharide. In another embodiment, the physiologically acceptable monomer is lactobionic acid. In another embodiment, the physiologically acceptable monomer is glucoronic acid. In another embodiment, the physiologically acceptable monomer is maltose. In another embodiment, the physiologically acceptable monomer is an amino acid. In another embodiment, the physiologically acceptable monomer is glycine. In another embodiment, the physiologically acceptable monomer is a carboxylic acid. In another embodiment, the physiologically acceptable monomer is an acetic acid. In another embodiment, the physiologically acceptable monomer is a butyric acid. In another embodiment, the physiologically acceptable monomer is a dicarboxylic acid. In another embodiment, the physiologically acceptable monomer is a glutaric acid. In another embodiment, the physiologically acceptable monomer is succinic acid. In another embodiment, the physiologically acceptable monomer is a fatty acid. In another embodiment, the physiologically acceptable monomer is dodecanoic acid. In another embodiment, the physiologically acceptable monomer is didodecanoic acid. In another embodiment, the physiologically acceptable monomer is bile acid. In another embodiment, the physiologically acceptable monomer is cholic acid. In another embodiment, the physiologically acceptable monomer is cholesterylhemmisuccinate.

In one embodiment of the invention, the physiologically acceptable dimer or oligomer is physiologically acceptable dimer or oligomer is a dipeptide. In another embodiment, the physiologically acceptable dimer or oligomer is a disaccharide. In another embodiment, the physiologically acceptable dimer or oligomer is a trisaccharide. In another embodiment, the physiologically acceptable dimer or oligomer is an oligosaccharide. In another embodiment, the physiologically acceptable dimer or oligomer is an oligopeptide. In another embodiment, the physiologically acceptable dimer or oligomer is a di- or trisaccharide monomer unit of glycosaminoglcans. In another embodiment, the physiologically acceptable dimer or oligomer is hyaluronic acid. In another embodiment, the physiologically acceptable dimer or oligomer is heparin. In another embodiment, the physiologically acceptable dimer or oligomer is heparan sulfate. In another embodiment, the physiologically acceptable dimer or oligomer is keratin. In another embodiment, the physiologically acceptable dimer or oligomer is keratan sulfate. In another embodiment, the physiologically acceptable dimer or oligomer is chondroitin. In another embodiment, the chondroitin is chondoitin sulfate. In another embodiment, the chondroitin is chondoitin-4-sulfate. In another embodiment, the chondroitin is chondoitin-6-sulfate. In another embodiment, the physiologically acceptable dimer or oligomer is dermatin. In another embodiment, the physiologically acceptable dimer or oligomer is dermatan sulfate. In another embodiment, the physiologically acceptable dimer or oligomer is dextran. In another embodiment, the physiologically acceptable dimer or oligomer is polygeline ('Haemaccel'). In another embodiment, the physiologically acceptable dimer or oligomer is alginate. In another embodiment, the physiologically acceptable dimer or oligomer is hydroxyethyl starch (Hetastarch). In another embodiment, the physiologically acceptable dimer or oligomer is ethylene glycol. In another embodiment, the physiologically acceptable dimer or oligomer is carboxylated ethylene glycol.

In one embodiment of the invention, the physiologically acceptable polymer is a glycosaminoglycan. In another embodiment, the physiologically acceptable polymer is hyaluronic acid. In another embodiment, the physiologically acceptable polymer is heparin. In another embodiment, the physiologically acceptable polymer is heparan sulfate. In another embodiment, the physiologically acceptable polymer is chondroitin. In another embodiment, the chondroitin is chondoitin-4-sulfate. In another embodiment, the chondroitin is chondoitin-6-sulfate. In another embodiment, the physiologically acceptable polymer is keratin. In another embodiment, the physiologically acceptable polymer is keratan sulfate. In another embodiment, the physiologically acceptable polymer is dermatin. In another embodiment, the physiologically acceptable polymer is dermatan sulfate. In another embodiment, the physiologically acceptable polymer is carboxymethylcellulose. In another embodiment, the physiologically acceptable polymer is dextran. In another embodiment, the physiologically acceptable polymer is polygeline ('Haemaccel'). In another embodiment, the physiologically acceptable polymer is alginate. In another embodiment, the physiologically acceptable polymer is hydroxyethyl starch ('Hetastarch'). In another embodiment, the physiologically acceptable polymer is polyethylene glycol. In another embodiment, the physiologically acceptable polymer is polycarboxylated polyethylene glycol.

In one embodiment of the invention, the lipid or phospholipid moiety is phosphatidic acid. In another embodiment, lipid or phospholipid moiety is an acyl glycerol. In another embodiment, lipid or phospholipid moiety is monoacylglycerol. In another embodiment, lipid or phospholipid moiety is diacylglycerol. In another embodiment, lipid or phospholipid moiety is triacylglycerol. In another embodiment, lipid or phospholipid moiety is sphingosine. In another embodiment, lipid or phospholipid moiety is sphingomyelin. In another embodiment, lipid or phospholipid moiety is ceramide. In another embodiment, lipid or phospholipid moiety is phosphatidylethanolamine. In another embodiment, lipid or phospholipid moiety is phosphatidylserine. In another embodiment, lipid or phospholipid moiety is phosphatidylcholine. In another embodiment, lipid or phospholipid moiety is phosphatidylinositol. In another embodiment, lipid or phospholipid moiety is phosphatidylglycerol. In another embodiment, lipid or phospholipid moiety is an ether or alkyl phospholipid derivative thereof In one embodiment, the invention provides a method of treating a subject afflicted with a disease, wherein the treatment of the disease requires controlling phospholipase A2 activities; controlling the production and/or action of lipid mediators, such as eicosanoids, platelet activating factor (PAF) and lyso-phospholipids; amelioration of damage to cell surface glycosaminoglycans (GAG) and proteoglycans; controlling the production of oxygen radicals and nitric oxide; protection of cells, tissues, and plasma lipoproteins from damaging agents, such as reactive oxygen species (ROS) and phospholipases; anti-oxidant therapy; anti-endotoxin therapy; controlling of cytokine, chemokine and interleukine production; controlling the proliferation of cells, including smooth muscle cells, endothelial cells and skin fibroblasts; controlling of angiogenesis and organ vascularization; inhibition of invasion-promoting enzymes, such as collagenase, heparinase, heparanase and hyaluronidase; controlling of cell invasion; controlling of white cell activation, adhesion and extravasation; amelioration of ischemia/reperfusion injury, inhibition of lymphocyte activation; controlling of blood vessel and airway contraction; protection of blood brain barrier; controlling of neurotransmitter (e.g., dopamine) production and action (e.g., acethylcholine); extracorporeal tissue preservation or any combination thereof In one embodiment of the invention, the term "controlling" refers to inhibiting the production and action of the above mentioned factors in order to maintain their activity at the normal basal level and suppress their activation in pathological conditions.

In one embodiment of the invention, the physiologically acceptable monomer is either a salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate; or wherein the physiologically acceptable dimer or oligomer is a dipeptide, a disaccharide, a trisaccharide, an oligopeptide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid; or wherein the physiologically acceptable polymer is a glycosaminoglycan, polygelin ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid.

In one embodiment of the invention, the lipid moiety is either phosphatidic acid, an acyl glycerol, monoacylglycerol, diacylglycerol, triacylglycerol, sphingosine, sphingomyelin, chondroitin-4-sulphate, chondroitin-6-sulphate, ceramide, phosphatidylethanolamine, phosphatidylserine, phosphatidylcholine, phosphatidylinositol, or phosphatidylglycerol, or an ether or alkyl phospholipid derivative thereof, and the physiologically acceptable monomer or polymer moiety is either aspirin, lactobionic acid, maltose, glutaric acid, polyethylene glycol, carboxymethylcellulose, heparin, dextran, hemacell, hetastarch, or hyaluronic acid.

In one embodiment, the present invention provides for use of a lipid moiety bonded to a physiologically acceptable monomer, dimer, oligomer, or polymer, in the preparation of a pharmaceutical composition for treating a subject afflicted with asthma, allergic rhinitis, chronic obstructive pulmonary disease, obstructive respiratory disease, colitis, Crohn's disease, central nervous system insult, multiple sclerosis, contact dermatitis, psoriasis, cardiovascular disease, including prophylaxis for invasive procedures, invasive cellular proliferative disorders, anti-oxidant therapy, hemolytic syndromes, sepsis, acute respiratory distress syndrome, tissue transplant rejection syndromes, autoimmune disease, viral infection, and hypersensitivity conjunctivitis.

In one embodiment, the present invention provides use of a pharmaceutical composition according to the present invention for treating a subject afflicted with asthma, allergic rhinitis, chronic obstructive pulmonary disease, obstructive respiratory disease, colitis, Crohn's disease, central nervous system insult, multiple sclerosis, contact dermatitis, psoriasis, cardiovascular disease, including prophylaxis for invasive procedures, invasive cellular proliferative disorders, anti-oxidant therapy, hemolytic syndromes, sepsis, acute respiratory distress syndrome, tissue transplant rejection syndromes, autoimmune disease, viral infection, or hypersensitivity conjunctivitis, wherein the composition is prepared for administration by topical, oral, nasal, aerosol, intravenous, intraocular, intra-arterial, subcutaneous, or suppository routes.

In one embodiment, the invention provides a method of treating a subject suffering from an intestinal disease, including, inter alia, the step of administering to a subject an effective amount of a lipid or phospholipid moiety bonded to a physiologically acceptable monomer, dimer, oligomer, or polymer, thereby treating the subject suffering from an intestinal disease In another embodiment, the invention provides a use of a lipid or phospholipid moiety bonded to a physiologically acceptable monomer, dimer, oligomer, or polymer, in the preparation of a pharmaceutical composition for treating a subject afflicted with an intestinal disease.

In one embodiment, the invention provides a method of treating a subject suffering from a disease involving the production and/or action of lipid mediators and/or impairment of glycosaminoglycan (GAG) functioning.

In another embodiment, the invention provides a pharmaceutical composition for treating a subject suffering from an intestinal disease, including, inter alia, a lipid or phospholipid moiety bonded to a physiologically acceptable monomer, dimer, oligomer, or polymer; and a pharmaceutically acceptable carrier or excipient.

In one embodiment, the intestinal disease may be, infer alia, a disease involving the production and/or action of lipid mediators and/or impairment of glycosaminoglycan (GAG) functioning.

In one embodiment of the invention, the intestinal disease may be, inter alia, Crohn's disease, ulcerative colitis, immuno-inflammatory intestinal injury, drug-induced enteropathy, ischemia-induced intestinal injury or any combination thereof.

In one embodiment of the invention, the physiologically acceptable monomer may be, inter alia, a salicylate, salicylic acid, aspirin, a monosaccharide, lactobionic acid, glucoronic acid, maltose, amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, or wherein the physiologically acceptable dimer or oligomer may be, inter alia, a dipeptide, a disaccharide, a trisaccharide, an oligosaccharide, an oligopeptide, or a di- or trisaccharide monomer unit of glycosaminoglcans, hyaluronic acid, heparin, heparan sulfate, keratin, keratan sulfate, chondroitin, chondroitin sulfate, chondroitin-4-sulfate, chondoitin-6-sulfate, dermatin, dermatan sulfate, dextran, polygeline, alginate, hydroxyethyl starch, ethylene glycol, or carboxylated ethylene glycol, or wherein the physiologically acceptable polymer may be, inter alia, a glycosaminoglycan, hyaluronic acid, heparin, heparan sulfate, chondroitin, chondroitin sulfate, keratin, keratan sulfate, dermatin, dermatan sulfate, carboxymethylcellulose, dextran, polygeline, alginate, hydroxyethyl starch, polyethylene glycol or polycarboxylated polyethylene glycol.

In another embodiment, the physiologically acceptable polymer may be, inter alia, hyaluronic acid.

In another embodiment, the physiologically acceptable polymer may be, inter alia, chondroitin sulfate.

In one embodiment of the invention, the lipid or phospholipid moiety may be, inter alia, phosphatidic acid, an acyl glycerol, monoacylglycerol, diacylglycerol, triacylglycerol, sphingosine, sphingomyelin, ceramide, phosphatidylethanolamine, phosphatidylserine, phosphatidylcholine, phosphatidylinositol, phosphatidylglycerol, or an ether or alkyl phospholipid derivative thereof.

In another embodiment, the phospholipid moiety may be, inter alia, phosphatidylethanolamine.

Dosages and Routes of Administration

The methods of this invention can be adapted to use of the therapeutic compositions comprising Lipid-conjugates in admixture with conventional excipients, i.e. pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

In one embodiment, the invention provides a pharmaceutical composition for treating a subject suffering from sepsis, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from asthma, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for preventing asthma in a subject, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from allergic rhinitis, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for preventing allergic rhinitis in a subject, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from chronic obstructive pulmonary disease, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for preventing chronic obstructive pulmonary disease in a subject, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from an obstructive respiratory disease, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for preventing obstructive respiratory disease in a subject, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from asthma, including any one of the compounds according to the invention or any combination thereof; and a pharmaceutically acceptable carrier or excipient. In another embodiment, the invention provides a pharmaceutical composition for preventing asthma in a subject, including any one of the compounds according to the invention or any combination thereof; and a pharmaceutically acceptable carrier or excipient. In another embodiment, the invention provides a pharmaceutical composition for treating a subject suffering from allergic rhinitis, including any one of the compounds according to the invention or any combination thereof; and a pharmaceutically acceptable carrier or excipient. In another embodiment, the invention provides a pharmaceutical composition for preventing allergic rhinitis in a subject, including any one of the compounds according to the invention or any combination thereof; and a pharmaceutically acceptable carrier or excipient. In another embodiment, the invention provides a pharmaceutical composition for treating a subject suffering from chronic obstructive pulmonary disease, including any one of the compounds according to the invention or any combination thereof; and a pharmaceutically acceptable carrier or excipient. In another embodiment, the invention provides a pharmaceutical composition for preventing chronic obstructive pulmonary disease in a subject, including any one of the compounds according to the invention or any combination thereof; and a pharmaceutically acceptable carrier or excipient. In another embodiment, the invention provides a pharmaceutical composition for treating a subject suffering from obstructive respiratory disease, including any one of the compounds according to the invention or any combination thereof; and a pharmaceutically acceptable carrier or excipient. In another embodiment, the invention provides a pharmaceutical composition for preventing obstructive respiratory disease in a subject, including any one of the compounds according to the invention or any combination thereof; and a pharmaceutically acceptable carrier or excipient.

In another embodiment, the compounds according to the invention include, inter alia, the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

While the examples provided herein describe use of the PL conjugates in subcutaneous, intraperitoneal or topical administration the success described affords good evidence to suppose that other routes of administration, or combinations with other pharmaceutical preparations, would be at least as successful. The route of administration (e.g., topical, par-enteral, enteral, intravenous, vaginal, inhalation, nasal aspiration (spray), supository or oral) and the dosage regimen will be determined by skilled clinicians, based on factors such as exact nature of the condition being treated, the severity of the condition, the age and general physical condition of the patient, and so on.

In general, the doses utilized for the above described purposes will vary, but will be in an effective amount to exert the desired anti-disease effect. As used herein, the term "pharmaceutically effective amount" refers to an amount of a compound of formulae A and I-XXI which will produce the desired alleviation in symptoms or signs of disease in a patient. The doses utilized for any of the above-described purposes will generally be from 1 to about 1000 milligrams per kilogram of body weight (mg/kg), administered one to four times per day, or by continuous IV infusion. When the compositions are dosed topically, they will generally be in a concentration range of from 0.1 to about 10% w/N, administered 1-4 times per day.

As used herein, the term "pharmaceutically acceptable carrier" refers to any formulation which is safe, and provides the appropriate delivery for the desired route of administration of an effective amount of at least one compound of the present invention. As such, all of the above-described formulations of the present invention are hereby referred to as "pharmaceutically acceptable carriers." This term refers to as well the use of buffered formulations wherein the pH is maintained at a particular desired value, ranging from pH 4.0 to pH 9.0, in accordance with is the stability of the compounds and route of administration.

For parenteral application, particularly suitable are injectable, sterile solutions, preferably oily or aqueous solutions, as well as suspensions, emulsions, or implants, including suppositories. Ampoules are convenient unit dosages.

For application by inhalation, particularly for treatment of airway obstruction or congestion, solutions or suspensions of the compounds mixed and aerosolized or nebulized in the presence of the appropriate carrier suitable.

For topical application, particularly for the treatment of skin diseases such as contact dermatitis or psoriasis, admixture of the compounds with conventional creams or delayed release patches is acceptable.

For enteral application, particularly suitable are tablets, dragees, liquids, drops, suppositories, or capsules. A syrup, elixir, or the like can be used when a sweetened vehicle is employed. When indicated, suppositories or enema formulations may be the recommended route of administration.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection.

Thus, the present invention provides for use of the Lipid-conjugates in various dosage forms suitable for aerosol, rectal, vaginal, conjunctival, intravenous, intra-arterial, and sublingual routes of administration.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Without further elaboration, it is believed that one skilled in the art can, using the is preceding description, utilize the present invention to its fullest extent. The following preferred specific embodiments are, therefore, to be construed as merely illustrative, and not limitative of the remainder of the disclosure in any way whatsoever.

EXAMPLES

The main abbreviations used in the examples below are:
HA=hyaluronic acid
HYPE=dipalmitoyl-phosphatidyl-ethanolamine (PE) conjugated to HA (also referred to as HyPE, HyalPE)
CSA=chondroitin sulfate A
CSAPE=PE conjugated to CSA (also referred to as CsAPE, CsaPE)
CMC=carboxymethyl cellulose
CMPE=PE conjugated to CMC
HEPPE=PE conjugated to heparin (also referred to as HepPE, HePPE)
DEXPE=PE conjugated to dextran
AsPE=PE conjugates to aspirin
HemPE=PE conjugated to Polygeline (haemaccel)
HyDMPE=dimyristoyl PE linked to HA
Examples demonstrating the utility of lipid-conjugates in preventing and treating disease are presented in PCT/US05/06591 filed 2-Mar.-2005, U.S. application Ser. No. 10/989,606 filed 17-Nov.-2004 and U.S. application Ser. No. 10/989,607 filed 17-Nov.-2004, which are incorporated herein by reference in their entirety.

Example 1

Obstructive Respiratory Disease

The Lipid-conjugates are effective in the treatment of obstructive respiratory disease. This is demonstrated for asthma in the Experiments 1-8 below. In asthma, the impeded airflow is due to airway obstruction which is the result of constriction and obstruction of luminal vessels of the lungs. One widely-accepted experimental system to investigate airway constriction is to induce smooth muscle preparations, isolated from airways, to contract in the absence and presence of the drug. Another widely-accepted test of anti-asthma drug action is to use live animals which have asthma. This disease is present in animals which have been sensitized to an antigen and which can be monitored for exacerbation and recovery from asthmatic breathing using a body plethysmography.

In Experiments 1.1-1.3, the muscle preparation (tracheal rings) was isolated from rats and in Experiment 1.4-1.5 from guinea pigs. Muscle contraction is measured by attachment of the muscle to a pressure transducer, which works much like a spring. Induction of contraction occurs when asthmatogenic substances are administered such as endothelin-1 (ET) an acetylcholine (AcCh).

Experiment 1.1: Isolated rat tracheal rings (in a linear array) were bathed in Krebs-Hanselet buffer (pH=7.4), and linked to a tension transducer. ET-1 was added to a final concentration as indicated, and the tracheal ring contraction was determined by the change in the force applied to the tension transducer (FIG. 1.1A). Subsequently, the highest ET concentration was used in testing the Lipid-conjugates to inhibit the smooth muscle contraction. In this experiment (FIG. 1.1B), rat trachea rings were incubated with the Lipid-conjugate HyPE at the indicated concentration for 1 hr. ET-1 was then added to a final concentration of 1 μM and the ring contraction was determined as in Experiment 1.1A. Each datum is mean±S.D. of four separate experiments (4 rats).

Experiment 1.2: Rat trachea rings were incubated with 3 μM HYPE or hyaluronic acid (HA) alone, for 1 hr. ET-1 was then added to a final concentration of 1 μM (empty bars) or 10 μM (full bars) and the tracheal ring contraction was determined as in Experiment 1.1 (FIG. 1.2).

Experiment 1.3: The same as Experiment 1.2, but the tracheal ring contraction was induced by 10 μM Acetyl Choline (AcCh), as shown in FIG. 1.3.

Experiment 1.4: Guinea pig tracheal rings (in a linear array), immersed in a ringer bath, were connected to an apparatus measuring the length of the ring chain. CMPE or HEPPE was added to the bath 1 h prior to the stimulation of contraction by either Crotalus atrox (type II) enzyme or endothelin-1 as indicated (Table 1.1).

TABLE 1.1

Inhibition of Tracheal Ring Contraction by CMPE and HEPPE

| Stimulant | Lipid-conjugate | % inhibition |
|---|---|---|
| Phospholipase (0.5 μ/ml) (crotalus atrox type II) | CMPE (10 μM) | 100 ± 0.3 |
| Histamine (20 μM) | CMPE (10 μM) | 69 ± 0.1 |
| Histamine (20 μM) | HEPPE (15 μM) | 56 ± 0.05 |
| Endothelin-1 (100 nM) | CMPE (10 μM) | 92 ± 1.1 |

Experiment 1.5: Guinea pig tracheal rings were incubated with or without CMPE for 30 minutes prior to stimulation. The medium was collected after 30 minutes and $PGE_2$ and $TXB_2$ were determined by radioimmunoassay (Table 1.2). (n.d.=below limit of detection.)

TABLE 1.2

Inhibition of Tracheal Tissue $PGE_2$ and $TBX_2$ Production by CMPE

| Stimulant | CMPE | $PGE_2$ (ng/ml) | $TXB_2$ (ng/ml) |
|---|---|---|---|
| Hitsamine (40 μM) | — | 5.1 | 5.6 |
| Histamine (40 μM) | 10 μM | n.d. | 1.75 |

Experiments 1.6-1.8 demonstrate the ability of Lipid-conjugates to exert their pharmacological effect in live animals. The following procedures were applied in these experiments:

Inbred Brown Norway male rats (4 weeks old) obtained from Harlan, USA, were used in this study. The Hebrew University Animal Welfare Committee approved all protocols.

Induction of asthma: Asthma was induced in rats by sensitization with ovalbumin (OVA, Sigma-Rehovot, Israel) according to a previously described protocol (33): On day 0 rats received a single subcutaneous injection of 1 mg OVA+ aluminum-hydroxide (200 mg/ml in 0.9% NaCl) (Sigma-Rehovot, Israel) and an intraperitoneal injection of 1 ml containing 6×109 heat-killed Bordetella Pertussis bacteria (Pasteur Marieux, France). Repeated bronchial allergen challenge was performed from day 14 every other day for 1 month by inhalation of OVA (1 mg/ml in 0.9% Normal Saline) for 5 minutes each time in a 20 L box connected to an ultrasonic nebulizer (LS 230 System Villeneuve Sur Lot, France).

Treatments: Rats were divided into 4 treatment groups: 1. No sensitization and no treatment, used as Naïve control. 2. Sensitization+challenge with OVA and no treatment, used as positive control. 3. Sensitization+challenge with OVA and treatment with Lipid-conjugate (HyPE), either by sub-cutaneous (SC) injection or inhalation, before every challenge (HyPE). 4 (in part of the experiments)–sensitization+challenge with OVA and treatment with SC injection of dexamethasone 300 μg before each challenge (OVA/Dx). The OVA/OVA group received 1 ml saline before each challenge.

Two modes of treatments with HyPE were employed: 1. The rats received SC injection of 1 ml saline containing 15 mg HyPE (to obtain about 1 mg/ml body fluid=20 μM). 2. The rats, placed unrestrained in a 20 liter box connected to an ultrasonic nebulizer, inhaled HyPE as follows: 5 ml of 1 mg/ml HyPE was aerosolized into the 20 L cage, thus diluting the HyPE to 0.25 μg/ml aerosol The rat respiratory rate was 120 breath/min, with a tidal volume of about 1 ml, thus reaching ventilation of 120 ml/minute. If all the inhaled HyPE was absorbed, in 5 min (inhaling 600 ml), the maximal HyPE absorbed was 150 μg In mode 1, all groups (5 rats in each) were treated and challenged as described above on day 14, 16, 18 and 20, and pulmonary function (Penh) was assessed on day 20 before and 5 min after challenge (EAR).

In mode 2, each group (10 rats in each) were treated and challenged from day 14, every other day, until day 45. Pulmonary function (Penh) was assessed on day 20 before and 5 min and 8 h after challenge, corresponding to early and late asthmatic reaction (EAR and LAR, respectively).

Assessment of broncho-constriction: Unrestrained conscious rats were placed in a whole-body plethysmograph (Buxco Electronics Inc., Troy, N.Y., USA) connected to a pneumotach (EMKA Technologies, Type 0000) at one end, and to a 10 ml bottle at the other end. The pneumotach was connected to a preamplifier (model MAX2270, Buxco Electronics). Analogue signals from the amplifier were converted to a digital signal by an AD card (LPM-16 National Instruments, Austin, Tex., USA). Broncho-constriction measures were expressed as the enhanced pause (Penh). Penh=(PEF/PIF)*((Te−Tr)/Tr), where PEF=Peak Expiratory Flow, PIF=Peak Inspiratory Flow, Te=Expiratory Time, Tr=Relaxation time=time of the pressure decay to 36% of total box pressure during expiration.

Broncho-alveolar lavage (BAL): On day 45 the rats were sacrificed by bleeding is through the abdominal aorta under anaesthesia with intra-peritoneal injection of sodium pentobarbital (100 mg/kg). The rats were tracheotomized and incannulated through the trachea. Bronco-alveolar lavage (BAL) was collected by repeated washing of the lungs with 5 ml saline to a total of 50 ml.

Assessment of airway pathology: Susequent to collection of BAL, lungs were removed and inflated with 4% buffered formaldehyde under pressure of 20 cm H2O. The lungs were sliced longitudinally and embedded in paraffin. Histological sections 3 µm thick were cut and stained with hematoxylin and eosin for assessments of interstitial and peri-bronchial inflammation and airway smooth muscle thickening. Other slides were stained with Tri-chrome for assessment of sub-epithelial fibrosis (basal membrane) and with PAS for epithelial cell mucus metaplasia.

Histological morphometry of airway structural changes was performed using a computer program "ImageJ" (NIH Bethesda USA) on 3 randomly selected slides from each mouse. Quantification of peribronchial cellular infiltrate in airway tissue was achieved through counting the numbers of these cells in the 50-µm region beneath the epithelium of the airway in hematoxylin and eosin stained sections. Cells were expressed as number per millimeter of airway basal lamina length, which was measured by tracing the basal lamina in calibrated digital images (43). Morphometric analysis of ASM and the basal membrane mass as indices of their thickening were performed as previously described (44). Briefly, measurements of the airway were obtained by tracing the digitalized images of interest. The outlines of the airway structures were subsequently measured. All airways were evaluated for the following morphometric dimensions: length of the airway basement membrane of the epithelium (Lbm) and area of the ASM in the eosin hematoxylin stained slides and the blue stain of the basal membrane of the Tri-chrome stained slides. ASM cells or the basal membrane thickening were normalized to the square of the Lbm (in µm2) to correct for differences in airway size. Only large (>2,000 µm Lbm) and medium size airways (1.000-2,000 µm Lbm) were selected as it was shown that the most significant pathological changes occur in these airways.

Protein expression of sPLA2 in lung tissue: Proteins were identified in homogenized lung tissue (100 µg protein) using standard Western blot. A specific polyclonal antibody against Anti-sPLA2 antibody (Santa Cruz) diluted 1:500 (v/v) in TBST buffer+0.1% BSA. The immune reaction was detected by enhanced chemiluminescence (ECL).

Cysteinyl Leukotriene (CysLT): CysLT levels were measured in BAL using a kit for direct enzyme immunoassay (EIA), according to manufacturer's instructions (Amersham Pharmacia Biotech U.K). The specificity of the kit was 100% for LTC4, 100% for LTD4, and 70% for LTE4. Result range was between 0 to 48 pg.

Cell culture—Cells were isolated from the BAL were suspended in DMEM medium supplemented with 10% fetal calf serum (FCS) and plated in a 96-well plate at 106 cells/well. The cells were incubated for 2 hours in 37° C., then non-adherent cells were removed by washing with PBS. The adherent cells were re-suspended in DMEM supplemented with 10% FCS at 106 cells/well and incubated for 48 hours. The culture medium was then collected and assayed for determination of biochemical markers.

Nitric Oxide (NO) production—NO production by the BAL cultured macrophages was determined by measuring their level in the culture medium using the photometric method of Griess et al. (45).

TNFα production: TNFα production by the BAL cultured macrophages was determined in the culture medium using radio-immunoassay (RIA) kits [Amersham-Pharamcia, UK).

Statistical Analysis: All data are expressed as mean±SEM. One way ANOVA was used to compare treatment groups. Pair-wise comparisons were performed by the Tukey-Kramer HSD test (p=0.05). Where necessary, data were log transformed before analysis to stabilized variances. In all analyses $P<0.05$ was considered statistically significant.

Statistics: Statistical analysis was performed using statistical software (GB-STAT, Dynamic Microsystem Silver Spring Md., USA. Analyzis of variance (ANOVA) was used to assess difference of the results of the treatment groups. A Tukey test was used to compare between each one of the treatment groups. A value of $p<0.05$ was considered as a significant difference.

Expeiment 1.6—demonstrates that SC-administration of Lipid conjugates considerably ameliorate OVA-induced broncho-constriction (FIG. 1.4, bronchoconstriction was induced in OVA-sensitized rats by inhalation of OVA, and expressed by the difference in Penh measured before and 5 min after allergen challenge. Each datum is Mean±SEM for 10 rats. Statistical significance: a–$P<0.01$; b, c–$P<0.05$), reduced the expression of secretory phospholiapse (FIG. 1.5, the figure depicts Western blot and corresponding densitometry of sPLA$_2$ in lung homogenates of rats with OVA-induced asthma, treated as indicated. In panel B, for each enzyme the density values were normalized to corresponding Naïve), and prevented the production of the broncho-constricting lipid mediators cysteinyl leukotrienes (FIG. 1.6, broncho-alveolar lavage (BAL) was collected upon sacrifice and CysLT levels were determined by EIA, as described in Methods. Each datum is Mean±SEM for 10 rats. Statistical significance: a, b–$P<0.01$. No significant difference between HyPE treated and the Naive rats).

Experiment 1.7 (aerosolic administration of HyPE) demonstrates that treatment of the asthmatic rats by inhalation of the Lipid-conjugate, reduces protects the rats from sensitization by OVA, as it markedly reduced OVA-induced broccho-constricyion in both the early and late asthmatic reaction (FIG. 1.7, bronchoconstriction, expressed as the percent change of Penh was induced in OVA-sensitized rats by inhalation of OVA, and measured before allergen challenge, 5 min and 8 h after allergen challenge. Each datum is Mean±SEM for 10 rats. Two experiments were performed for EAR. 5 rats were included in each group in the first experiment. The same experiment was repeated with 10 rats in each group, which were further used for determination of LAR. Combined statistical test for EAR yielded $p<0.01$ between Asthmatic and HyPE-treated; no significant difference between the HyPE-treated and the Naive or Dx-treated groups. For LAR, $p<0.01$ between Asthmatic and HyPE-treated; no significant difference between the HyPE-treated and the Naive or Dx-treated groups), inhibited the production of CysLT, potent broncho-constricting lipid mediator (FIG. 1.8, broncho-alveolar lavage (BAL) was collected upon sacrifice and CysLT levels were determined by EIA. Each datum is Mean±SEM for 10 rats. $P<0.01$ between asthmatic and HyPE-treated rats. No significant difference between HyPE treated and the Naive rats), and of nitric oxide (NO), a characteristic constrictor of smooth muscle cells (FIG. 1.9, macrophages, collected from the BAL of the different groups, were cultured without further treatment with HyPE or Dx, and NO production was determined as described in Methods. Each datum is Mean±SEM for 10 rats. NO level was reduced compared to asthmatic and naïve rats by both HyPE, $p<0.001$ and $p<0.001$ respectively and by Dx $p<0.001$ and $p<0.001$, respectively.) These treatments also prevented the asthma-associated inflammation, as expressed by prevention of inflammatory cell infiltration and airway remodeling (FIG. 1.10, rats were subjected to OVA inhalation every other day for 30 days. For treatment with HyPE, the rats inhaled HyPE aerosol for 5 min before every allergen inhalation. The rats were sacrificed on Day 45. A—Staining with hematoxylin eosin for detection of inflammatory cell infiltration and changes in smooth muscle cell (ASM) thickness. B—Staining of connective tissue (collagen) with Mason-Trichrom, for detection of changes in basal membrane thickness. C—Staining with Periodic Acid Schiff (PAS) for detection of mucus metaplasia of respiratory epithelial cells. 1, 2, 3 and 4 depict tissues of Naive, Asthmatic, HyPE-treated and Dx-treated rats, respectively, and FIG. 1.11), and production of TNF-alfa by lung macrophages (FIG. 1.12, macrophages, collected from the BAL of the different groups, were cultured without further treatment with HyPE or Dx, and NO production was determined as described in Methods, Each datum is Mean±SEM for 10 rats. p<0.001 between asthmatic and HyPE-treated rats. No significant difference between HyPE-treated, Naive and Dx-treated rats).

Experiment 1.8, in which HyPE was given as aerosol to only before challenge to rats that had been sensitized by OVA (HyPE was not given during sensitization as in Experiment 1.7), demonstrates that inhalation of Lipid conjugates is effective in preventing allergen-induced broncho-condtriction in already asthmatic subjects when inhaled before allergen (OVA) challenge (FIG. 1.13, OVA-sensitized asthmatic rats inhaled nebulized HyPE (1 mg/ml) for 5 minutes, or nebulized normal saline. 30 minutes later all were challenged by inhalation of OVA (1 mg/ml) for 5 minutes. Penh was measured before the treatments (baseline), and 5 minutes after each inhalation. Each datum is mean±SEM for 5 rats. *,**, P<0.05), and revrese broncho-constricion (induce broncho-dilation) when inhaled after allergen challege. FIG. 1.14: OVA-sensitized asthmatic rats challenged by imhalation of OVA (1 mg/ml) for 5 minutes. 30 minutes later they were treated by inhaltion of nebulized HyPE inhalation (1 mg/ml) or nebulized or with normal saline for 5 minutes. Penh was measured before challenge (baseline), and after challenge and treatment. Each datum is mean±SEM for 5 rats. *, P<0.05.

These experiments demonstrate that the Lipid-conjugates may be used for the treatment of obstructive respiratory disease, alleviating airway narrowing by a plurality of mechanisms, including inhibition of contraction and reduction of airway obstructing infiltrates.

Example 2

Anti-Oxidant Therapy

The Lipid-conjugates are effective therapy for preventing oxidative damage. This is demonstrated in Experiments 2.1-2.3. The noxious effect of peroxide free radicals on living tissue is known as oxidative damage. When cell membranes are the targets for this damaging process, membrane dysfunction and instability result. Oxidative damage to blood proteins, particularly blood lipid proteins, results in their overaccumulation in cells lining the vasculature, thus contributing to atherogenesis. In fact, oxidative cell damage is a major mechanism attributed to the process of aging or senescence.

Oxidative damage to proteins or cell membranes is commonly assessed by exposing these tissues to hydrogen peroxide produced by the enzyme glucose oxidase (GO), in the absence or presence of additional membrane destabilizing agents, such as $PLA_2$, or by exposure to divalent cations, such as copper.

Experiments 2.1-2.3 demonstrate the ability of Lipid-conjugates to preserve cells from oxidative damage, as judged by the cells' retention of both arachidonic acid and of low molecular weight intracellular substances.

Experiment 2.1: Confluent BGM (green monkey kidney epithelial cells) were labeled with $^3H$-arachidonic acid, The cells were treated with CMPE for 30 min prior to treatment with GO and $PLA_2$ (0.5 u/ml) (FIG. 2.1).

Experiment 2.2: BGM cells were labeled with $^{35}SO_4$ overnight. The cells were washed with DMEM (containing 10 mg/ml BSA) 4 times with PBS. The cells were then incubated in DMEM supplemented with GO (an $H_2O_2$ generation) for 90, and the culture medium was collected and counted for $^{35}S$ radioactivity For treatment with CMPE cells were incubated with CMPE, at the indicated concentration for 30 min prior to introduction of GO. Each datum is MEAN±SEM for 5 replications. *p<0.005; **p<0.001 (FIG. 2.2).

Experiment 2.3: For demonstrating the ability of Lipid-conjugates to inhibit the oxidation of blood lipoprotein. LDL (0.1 μM) was incubated in the absence and presence of various concentrations of HYPE or HA at 37° C. At time zero 5 μM $CuCl_2$ was added to the dispersions and the mixtures were continuously monitored for oxidation products at 245 nm (FIG. 2.3). The absorbance at 245 (OD units) is depicted as a function of time (Schnitzer et al., Free Radical Biol Med 24; 1294-1303, 1998).

These experiments demonstrate that administration of Lipid-conjugates is effective therapy in the prevention of tissue damage induced by oxidative stress (associated with free radical and hydrogen peroxide production) by a plurality of mechanisms, including inhibiting the oxidation of lipoprotein, as well as their uptake, inhibiting arachidonic acid release, and preserving the integrity of cell membranes (inhibiting GAG degradation), including red blood cell membranes.

Example 3

Lung Injury/Acute Respiratory Distress Syndrome (ARDS)

In acute respiratory distress syndrome (ARDS), which is usually induced by bacterial endotoxins (LPS, LTA), a high production of injurious mediators, particularly neutrophil-attracting chemokines, and cytokines, are produced by the lung microvascular endothelial cells (LMVEC). To demonstrate the ability of the Lipid-conjugates to control the production of these injurious agents, LMVEC were treated with LPS (gram-positive bacterial endotoxin) and LTA (gram-negative bacterial endotoxin), in the absence and presence of Lipid-conjugates, and tested for the subsequent production of cytokines and adhesion molecules, To this end, human lung microvascular endothelial cells (LMVEC) were purchased from CellSystems, Remagen, Germany at passage 4. The cells were seeded in a density of 5000 cells$^{-cm2}$ in T25 flasks and maintained according to the manufacturer's specification in EGM-MV. Characterization of the LMVEC was performed on the basis of a positive staining for uptake of acetylated LDL, Factor VIII related antigen and PECAM (CD31) expression as well as negative staining for alpha smooth muscle actin. In each experiment the viability of LPS- and LTA-stimulated or HyPE-treated LMVEC was tested by trypan blue exclusion. The production and mRNA expression of cytokines and adhesion molecules were determined as described in U.S. application Ser. No. 10/989,606 filed 17-Nov.-2004, which is incorporated herein by reference in its entirety.

The production of the chemokines ENA-78, Gro-α and IL-8, secreted into the culture medium of stimulated LMVEC, was measured by ELISAs according to the manufacturer's instructions.

For RNA isolation and Polymerase Chain Reaction by RT-PCR, confluent LMVEC were stimulated with medium as control or with LPS (1 μg$^{-ml}$) or LTA (10 μg$^{-ml}$) in the presence or absence of HyPE (10 μM). Total RNA was isolated using Trizol-Reagent according to the manufacturer's instructions. Each RNA preparation was subjected to DNAse digestion to remove possible contaminations of genomic DNA. 1 μg of total RNA was reverse transcribed using SuperScript™ II Preamplification System according to the manufacturer's instructions. Amplification of 0.5 μl of cDNA was performed in a total volume of 25 μl containing 19.6 pmol of each chemokine primer, 5 mM of dNTPs, 2.5 U Taq Polymerase, 10 mM Tris HCl, 7.5 mM KCl, 1.5 mM $MgCl_2$. PCR reactions were initiated at 94° C. for 3 min, followed by 30 cycles of amplification, each consisting of 94° C. for 1 min, 58° C. for 1 min, 72° C. for 2 min. At the end of the amplification cycles die products were incubated for 10 min at 72° C. Control samples were constructed either by omitting cDNA synthesis or without addition of cDNA. PCR products were separated on a 1% agarose gel. Real-time PCR: 500 ng of total RNA of each sample was in addition reverse-transcribed into cDNA for Real-time PCR analysis using 1st Strand cDNA Synthesis Kit according to the manufacturer's instructions (Roche). cDNA was diluted in 20 μl DEPC-treated water. DNA standards were generated by PCR amplification of gene products, purification and quantification by spectrophotometry. Real time PCR of cDNA specimens and DNA standards were performed in a total volume of 25 μl in the presence of 2 μl Light cycler-FastStart DNA Master SYBR GreenI reaction mix, 0.5 μM of gen-specific primers and 4 mM $MgCl_2$. Standard curves were generated for all chemokines. PCR efficiency was assessed from the slopes of the standard curves and was found to be between 90% and 100%. Concentration of chemokine cDNA was calculated by linear regression analysis of all standard curves and was corrected for an equal expression of GAPDH. At least five reproducible experiments were performed.

Adhesion molecules ICAM-1 and p-selectin were determined by fluorescence-activated cell sorter (FACS); Confluent LMVEC were stimulated with medium as control or with LPS ($1 \mu g^{-ml}$) or LTA ($10 \mu g^{-ml}$) in the presence or absence of HyPE (10 μM). Thereafter cells were harvested by T/E, extensively washed and monoclonal antibodies directed against the endothelial adhesion molecules ICAM-1 and P-selectin in dilutions of 1:20 were added for 30 min at 4° C. In addition unstimulated or stimulated cells were harvested as described and preincubated for 20 min with HyPE (10 μM) and monoclonal antibodies against TLR4. Cells were washed and incubated with an anti-mouse F(ab')2, FITC conjugated secondary antibody. After washing cells were analyzed by FACS-scan.

Expression of NFκB was determined by Electrophorese mobility shift assay (EMSA); Confluent LMVEC were preincubated overnight in basal medium containing 0.01% BSA. Thereafter they were stimulated or not for different time periods with LPS, IL-1 or TNF-α in the presence or absence of HyPE, and respective nuclear extracts were prepared. Oligonucleotides containing a NFkB consensus sequence (5'-AGT TGA GGG GAC TTT CCC AGG C-3') were labeled to a specific activity $>5 \times 10^7$ $cpm^{-\mu g}$ DNA. NF-kB-binding was performed in 10 mM HEPES, (pH=7,5), 0.5 mM EDTA, 70 mM KCl, 2 mM DTT, 2% glycerol, 0.025% NP-40, 4% Ficoll, 0.1 M PMSF, 1 $mg^{-ml}$ BSA and 0.1 $\mu g^{-\mu l}$ poly di/dc in a total volume of 20 μl Nuclear extracts (10 μg) were incubated for 30 minutes at room temperature in the presence of 1 ng labeled oligonucleotide. DNA-protein complexes were resolved on 5% non-denaturating polyacrylamide gels electrophoresed in low ionic strength buffer and visualized by autoradiography. Specificity of shifted bands was demonstrated by adding a cold NFκB consensus sequence or by supershift using anti-p65 antibodies.

Experiment 3.1 demonstrates that the Lipid-conjugates are effective in suppressing the endotoxin-induced production and RNA expression of the chemokines IL-8, ENA-78 and Gro-α and their mRNA expression as shown in FIGS. 3.1, 3.2 and 3.3.

Experiment 3.2 demonstrates that the Lipid-conjugates are effective in suppressing the expression of the adhesion molecules ICAM-1 and E-selectin (FIG. 3.4).

Experiment 3.3 demonstrates that Lipid-conjugates are effective in suppressing the expression of NFκB, the transcription factor that is enhanced in endotoxin-induced injurious states (FIG. 3.5).

These results further demonstrate the therapeutic capacity of the Lipid-conjugates in the treatment of ARDS and lung injuries, as well as other disease that share common mechanisms, such as peritonitis, kidney failure, organ transplantation and the like.

Example 4

Toxicity Tests

Experiment 4: The following compounds were tested: HyPE, CMPE, CSAPE and HepPE. The compounds were injected IP at one dose of 1000, 500 or 200 mg/1 g body weight. Toxicity was evaluated after one week, by mortality, body weight, hematocrit, blood count (red and white cells), and visual examination of internal organs after sacrifice. These were compared to control, untreated mice. Each dose was applied to a group of three mice. No significant change in the above criteria was induced by treatment with these compounds, except for the HepPE, which induced hemorrhage.

The non-toxicity of the Lipid conjugates is demonstrated in Table 4.1 and Table 4.2, depicting the results obtained for HyPE in acute (4.1) and long-term (4.2) toxicity tests.

TABLE 4.1

| | Acute toxicity | | | | |
| --- | --- | --- | --- | --- | --- |
| Dose of HyPE (mg/kg body weight) | Body weight (g) | | RBC $\times 10^6$ | WBC $\times 10^3$ | Hematocrit % |
| 0.0 (control) | 21.9 ± 0.2 | 22.6 ± 0.3 | 10.7 ± 0.4 | 9.3 ± 0.3 | 45.0 ± 0.5 |
| 250 | 22.1 ± 0.4 | 23.1 ± 0.6 | 11.4 ± 0.1 | 7.7 ± 0.2 | 43.3 ± 0.7 |
| 500 | 21.4 ± 0.3 | 22.3 ± 0.4 | 11.5 ± 0.3 | 8.1 ± 1.3 | 44.7 ± 2.3 |
| 1000 | 21.7 ± 0.2 | 22.1 ± 0.2 | 10.9 ± 0.4 | 7.4 ± 0.6 | 40.3 ± 0.7 |

RBC = red blood cells. WBC = white blood cells. Each datum is mean ± SEM.

For long-term toxicity test of HyPE, a group of 6 mice received a dose of 100 mg HyPE/Kg body weight, injected IP 3 times a week for 30 weeks (total of 180 mg to a mouse of 20 g). Toxicity was evaluated as for Table 4.1. No mortality, and no significant change in the above criteria was induced by this treatment, compared to normal untreated mice (see Table 4.1), as depicted in Table 4.2.

TABLE 4.2

| | Body weight (g) | RBC × 10⁶ | WBC × 10³ | Hematocrit % |
|---|---|---|---|---|
| Control (untreated) rats | 39.5 ± 3.1 | 10.9 ± 0.8 | 9.3 ± 0.6 | 45.0 ± 0.8 |
| HyPE-injected rats | 39.0 ± 2.7 | 11.7 ± 0.7 | 8.1 ± 15 | 43.4 ± 4.9 |

Example 5

Synthesis Procedures

The procedures below are examples for synthesis of specific variants of the lipid-conjugates, and can be modified according to the desirable compositions (e.g., changing the molar ratio between the lipid/phospholipid and the GAG, or the GAG size).

I. HyPE=phosphatidyl-ethanolamine (PE)-linked hyaluronic acid.

A. Truncating hyaluronic acid (HA):
Dissolve 20 g of HA in 12 L water, add 200 mg $FeSO_4.7H_2O$ dissolved in 20 ml water, add 400 ml $H_2O_2$ (30%), stir for 1.5 h. Filter through 30 kD Filtron, Lyophilize. Yield: 16 g truncated HA.

B. Conjugation with PE (adjusted for 1 g):
Prepare:
1. 10 g HA dissolved in 500 ml MES buffer, 0.1 M, pH=6.5
2. 1.0 g PE dissolved in 500 ml t-BuOH with 100 ml $H_2O$.

Mix the two solutions, add 1 g HOBT and 10 g EDC. Sonicate the mixture in an ultrasonic bath for 3 h. Remove access free PE (and EDC and HOBT) by extraction into organic phase (by addition of chloroform and methanol to obtain a ratio of $C/M/H_2O$:1/1/1). Separate the aqueous phase by a separation funnel. Repeat this step twice. For final cleaning from reagents, filter through a Filtron membrane (30 kD), and lyophilize.
Yield: about 8 g.

II. CSAPE=PE-linked chondroitin sulfate A (CSA):
Prepare:
1. 10 g CSA dissolved in 1.2 L MES buffer, 0.1 M, pH=6.5
2. 1 g PE dissolved in 120 ml chloroform/methanol: 1/1. Add 15 ml of a detergent (DDAB).

Mix 1 with 2, while stirring, add 1 g HOBT and 10 g EDC, continue stirring thoroughly for a day at least. Remove access free PE (and EDC and HOBT) by extraction into organic phase (by addition of chloroform and methanol to obtain a ratio of Chloroform/MeOH/EtOH/$H_2O$:1/1/0.75/1). Separate the aqueous phase by a separation funnel. Repeat this step twice. Filter through a Filtron membrane (30 kD), and lyophilize. To remove DDAB traces, dissolve 1 g of dry product in 100 ml water and 100 ml MeOH, and clean by ion exchanger using IR120 resin.
Dialyse (to remove MeOH) and lyophilize.
Yield: about 8 g.

Unexpected results showed that the sonication applied in the HyPE synthesis, is an better substitute for the detergent in mixing the aqueous and lipid phases. Using sonication techniques simplifies the synthesis and improves the purification of the product.

It will be appreciated by persons skilled in the art that the present invention is not limited by what has been particularly shown and described herein above and that numerous modifications, all of which fall within the scope of the present invention, exist. Rather, the scope of the invention is defined by the claims which follow:

What we claim is:

1. A method of decreasing the number or frequency of relapse episodes or reducing the incidence of disease-related symptoms of asthma in a subject, comprising the step of administering to a subject a compound represented by the structure of the general formula I:

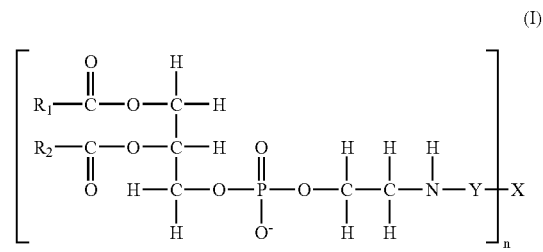

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is a glycosaminoglycan; and 2 to 200; and
n is a number 2 to 200;
wherein said spacer comprises —CO-alkylene-NH—, —CO-alkylene-CO— or a combination thereof and said spacer is linked to a hydroxyl or carboxylic acid of said glycosaminoglycan; and wherein if Y is nothing the phosphatidylethanolamine is directly linked to glycosaminoglycane via a carboxylic group.

2. The method according to claim 1, wherein said glycosaminoglycan is hyaluronic acid.

3. The method according to claim 1, wherein said glycosaminoglycan is heparin.

4. A method of treating a subject suffering from allergic rhinitis, comprising the step of administering to a compound represented by the structure of the general formula I:

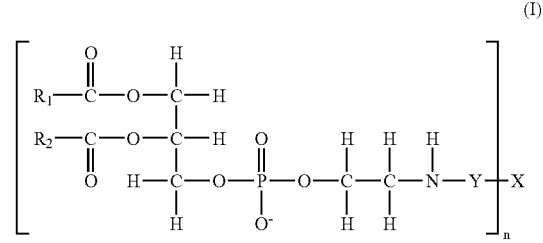

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is a glycosaminoglycan; and n is a number 2 to 200;

wherein said spacer comprises —CO-alkylene-NH—, —CO-alkylene-CO— or a combination thereof and said spacer is linked to a hydroxyl or carboxylic acid of said glycosaminoglycan; and wherein if Y is nothing the phosphatidylethanolamine is directly linked to glycosaminoglycane via a carboxylic group.

5. The method according to claim 4, wherein said glycosaminoglycan is hyaluronic acid.

6. The method according to claim 4, wherein said glycosaminoglycan is heparin.

7. A method of decreasing the number or frequency of relapse episodes or reducing the incidence of disease-related symptoms of allergic rhinitis in a subject, comprising the step of administering to a subject a compound of formula I:

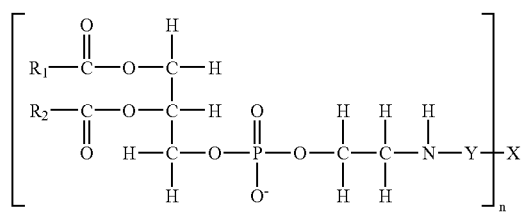

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is a glycosaminoglycan; and n is a number 2 to 200;

wherein said spacer comprises —CO-alkylene-NH—, —CO-alkylene-CO— or a combination thereof and said spacer is linked to a hydroxyl or carboxylic acid of said glycosaminoglycan; and wherein if Y is nothing the phosphatidylethanolamine is directly linked to glycosaminoglycane via a carboxylic group.

8. The method according to claim 7, wherein said glycosaminoglycan is hyaluronic acid.

9. The method according to claim 7, wherein said glycosaminoglycan is heparin.

10. A method of treating a subject suffering from chronic obstructive pulmonary disease, comprising the step of administering to a subject a compound of formula I:

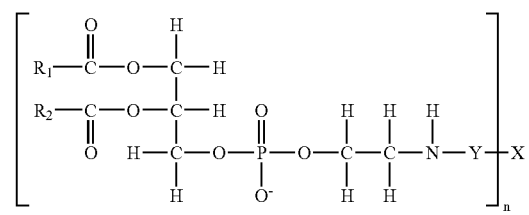

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is a glycosaminoglycan; and n is a number 2 to 200;

wherein said spacer comprises —CO-alkylene-NH—, —CO-alkylene-CO— or a combination thereof and said spacer is linked to a hydroxyl or carboxylic acid of said glycosaminoglycan; and wherein if Y is nothing the phosphatidylethanolamine is directly linked to glycosaminoglycane via a carboxylic group.

11. The method according to claim 10, wherein said glycosaminoglycan is hyaluronic acid.

12. The method according to claim 10, wherein said glycosaminoglycan is heparin.

13. A method of decreasing the number or frequency or reducing the incidence of disease-related symptoms of chronic obstructive pulmonary disease in a subject, comprising the step of administering to a subject a compound represented by the structure of the general formula I:

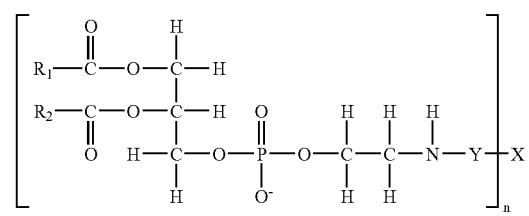

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is a glycosaminoglycan; and n is a number 2 to 200;

wherein said spacer comprises —CO-alkylene-NH—, —CO-alkylene-CO— or a combination thereof and said spacer is linked to a hydroxyl or carboxylic acid of said glycosaminoglycan; and wherein if Y is nothing the phosphatidylethanolamine is directly linked to glycosaminoglycane via a carboxylic group.

14. The method according to claim 13, wherein said glycosaminoglycan is hyaluronic acid.

15. The method according to claim 13, wherein said glycosaminoglycan is heparin.

16. The method according to claim 1, wherein said glycosaminoglycan is chondroitin sulfate.

17. The method according to claim 16, wherein said chondroitin sulfate is chondroitin-6-sulfate or chondroitin-4-sulfate.

18. The method according to claim 1, wherein said phosphatidylethanolamine is dimyrisotyl phosphatidylethanolamine or dipalmitoyl phosphatidylethanolamine.

19. The method according to claim 4, wherein said glycosaminoglycan is chondroitin sulfate.

20. The method according to claim 19, wherein said chondroitin sulfate is chondroitin-6-sulfate or chondroitin-4-sulfate.

21. The method according to claim 4, wherein said phosphatidylethanolamine is dimyrisotyl phosphatidylethanolamine or dipalmitoyl phosphatidylethanolamine.

22. The method according to claim 7, wherein said glycosaminoglycan is chondroitin sulfate.

23. The method according to claim 22, wherein said chondroitin sulfate is chondroitin-6-sulfate or chondroitin-4-sulfate.

24. The method according to claim 7, wherein said phosphatidylethanolamine is dimyrisotyl phosphatidylethanolamine or dipalmitoyl phosphatidylethanolamine.

25. The method according to claim 10, wherein said glycosaminoglycan is chondroitin sulfate.

26. The method according to claim 25, wherein said chondroitin sulfate is chondroitin-6-sulfate or chondroitin-4-sulfate.

27. The method according to claim 10, wherein said phosphatidylethanolamine is dimyrisotyl phosphatidylethanolamine or dipalmitoyl phosphatidylethanolamine.

28. The method according to claim 13, wherein said glycosaminoglycan is chondroitin sulfate.

29. The method according to claim 28, wherein said chondroitin sulfate is chondroitin-6-sulfate or chondroitin-4-sulfate.

30. The method according to claim 13, wherein said phosphatidylethanolamine is dimyrisotyl phosphatidylethanolamine or dipalmitoyl phosphatidylethanolamine.

31. A method of delaying the onset of symptoms of asthma in a subject, comprising the step of administering to a subject a compound represented by the structure of the general formula I:

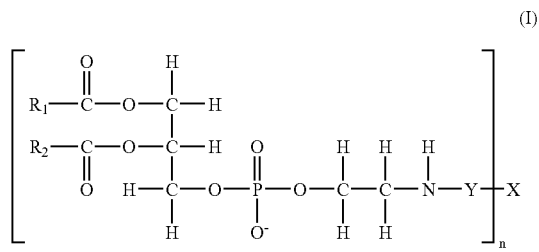

wherein
$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is a glycosaminoglycan; and n is a number 2 to 200;

wherein said spacer comprises —CO-alkylene-NH—, —CO-alkylene-CO— or a combination thereof and said spacer is linked to a hydroxyl or carboxylic acid of said glycosaminoglycan; and wherein if Y is nothing the phosphatidylethanolamine is directly linked to glycosaminoglycane via a carboxylic group.

32. The method according to claim 31, wherein said glycosaminoglycan is hyaluronic acid.

33. The method according to claim 31, wherein said glycosaminoglycan is heparin.

34. A method of delaying the onset of symptoms of allergic rhinitis in a subject, comprising the step of administering to a subject a compound represented by the structure of the general formula I:

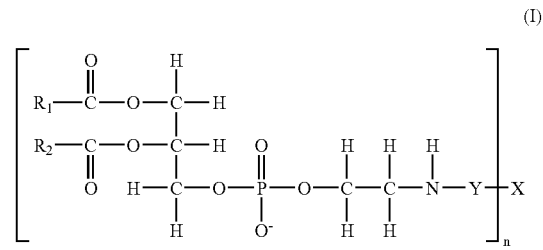

wherein
$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is a glycosaminoglycan; and n is a number 2 to 200;

wherein said spacer comprises —CO-alkylene-NH—, —CO-alkylene-CO— or a combination thereof and said spacer is linked to a hydroxyl or carboxylic acid of said glycosaminoglycan; and wherein if Y is nothing the phosphatidylethanolamine is directly linked to glycosaminoglycane via a carboxylic group.

35. The method according to claim 34, wherein said glycosaminoglycan is hyaluronic acid.

36. The method according to claim 34, wherein said glycosaminoglycan is heparin.

37. A method of delaying the onset of symptoms of chronic obstructive pulmonary disease in a subject, comprising the step of administering to a subject a compound represented by the structure of the general formula I:

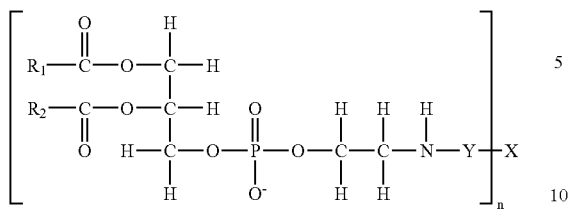

(I)

wherein
R₁ is a linear, saturated, mono-unsaturated, or poly-unsaturated, alkyl chain ranging in length from 2 to 30 carbon atoms;
R₂ is a linear, saturated, mono-unsaturated, or poly-unsaturated, alkyl chain ranging in length from 2 to 30 carbon atoms;
Y is either nothing or a spacer group ranging in length from 2 to 30 atoms; and
X is a glycosaminoglycan; and
n is a number 2 to 200;
wherein said spacer comprises —CO-alkylene-NH—, —CO-alkylene-CO— or a combination thereof and said spacer is linked to a hydroxyl or carboxylic acid of said glycosaminoglycan; and wherein if Y is nothing the phosphatidylethanolamine is directly linked to glycosaminoglycane via a carboxylic group.

38. The method according to claim 37, wherein said glycosaminoglycan is hyaluronic acid.

39. The method according to claim 37, wherein said glycosaminoglycan is heparin.

40. The method according to claim 31, wherein said glycosaminoglycan is chondroitin sulfate.

41. The method according to claim 40, wherein said chondroitin sulfate is chondroitin-6-sulfate or chondroitin-4-sulfate.

42. The method according to claim 31, wherein said phosphatidylethanolamine is dimyrisotyl phosphatidylethanolamine or dipalmitoyl phosphatidylethanolamine.

43. The method according to claim 34, wherein said glycosaminoglycan is chondroitin sulfate.

44. The method according to claim 43, wherein said chondroitin sulfate is chondroitin-6-sulfate or chondroitin-4-sulfate.

45. The method according to claim 34, wherein said phosphatidylethanolamine is dimyrisotyl phosphatidylethanolamine or dipalmitoyl phosphatidylethanolamine.

46. The method according to claim 37, wherein said glycosaminoglycan is chondroitin sulfate.

47. The method according to claim 46, wherein said chondroitin sulfate is chondroitin-6-sulfate or chondroitin-4-sulfate.

48. The method according to claim 37, wherein said phosphatidylethanolamine is dimyrisotyl phosphatidylethanolamine or dipalmitoyl phosphatidylethanolamine.

49. A method of treating a subject suffering from asthma, comprising the step of administering to a subject a compound of formula I:

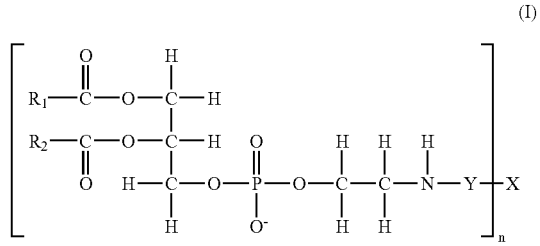

(I)

wherein
R₁ is a linear, saturated, mono-unsaturated, or poly-unsaturated, alkyl chain ranging in length from 2 to 30 carbon atoms;
R₂ is a linear, saturated, mono-unsaturated, or poly-unsaturated, alkyl chain ranging in length from 2 to 30 carbon atoms;
Y is either nothing or a spacer group ranging in length from 2 to 30 atoms; and
X is a glycosaminoglycan; and
n is a number 2 to 200;
wherein said spacer comprises —CO-alkylene-NH—, —CO-alkylene-CO— or a combination thereof and said spacer is linked to a hydroxyl or carboxylic acid of said glycosaminoglycan; and wherein if Y is nothing the phosphatidylethanolamine is directly linked to glycosaminoglycane via a carboxylic group.

50. The method according to claim 49, wherein said glycosaminoglycan is hyaluronic acid.

51. The method according to claim 49, wherein said glycosaminoglycan is heparin.

52. The method according to claim 49, wherein said glycosaminoglycan is chondroitin sulfate.

53. The method according to claim 46, wherein said chondroitin sulfate is chondroitin-6-sulfate or chondroitin-4-sulfate.

54. The method according to claim 49, wherein said phosphatidylethanolamine is dimyrisotyl phosphatidylethanolamine or dipalmitoyl phosphatidylethanolamine.

* * * * *